(12) United States Patent
Condeelis

(10) Patent No.: US 8,298,756 B2
(45) Date of Patent: Oct. 30, 2012

(54) ISOLATION, GENE EXPRESSION, AND CHEMOTHERAPEUTIC RESISTANCE OF MOTILE CANCER CELLS

(75) Inventor: John S. Condeelis, City Island, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 318 days.

(21) Appl. No.: 11/659,514

(22) PCT Filed: Aug. 4, 2005

(86) PCT No.: PCT/US2005/027680
§ 371 (c)(1),
(2), (4) Date: Sep. 26, 2007

(87) PCT Pub. No.: WO2006/017635
PCT Pub. Date: Feb. 16, 2006

(65) Prior Publication Data
US 2008/0138805 A1 Jun. 12, 2008

Related U.S. Application Data

(60) Provisional application No. 60/600,697, filed on Aug. 11, 2004.

(51) Int. Cl.
*C12Q 1/68* (2006.01)
*G01N 33/574* (2006.01)
(52) U.S. Cl. ......... 435/4; 435/6.14; 435/6.17; 435/7.23; 435/7.24
(58) Field of Classification Search .................. None
See application file for complete search history.

(56) References Cited

U.S. PATENT DOCUMENTS

2005/0014208 A1* 1/2005 Krehan et al. ............... 435/7.23

FOREIGN PATENT DOCUMENTS

| WO | WO03/023060 | * | 3/2003 |
| WO | WO2004/015396 | * | 2/2004 |

OTHER PUBLICATIONS

Dong et al (Cancer Research, 2001, vol. 61, pp. 4797-4808).*
Jang et al (Clinical and Experimental Metastasis, 1997, vol. 15, pp. 469-483).*
Wyckoff J B et al., entitled "The Collection of the Motile Population of Cells from a Living Tumor," Cancer Research 60:5401-5404, Oct. 2000.
Wang W et al., Gene expression analysis on small numbers of invasive cells collected by chemotaxis from primary mammary tumors of the mouse, BMC Biotechnology 3:13, Aug. 2003, 12 pages.
Wang W et al., entitled "Single cell behavior in metastatic primary mammary tumors correlated with gene expression patterns revealed by molecular profiling," Cancer Research 62: 6278-6288, Nov. 2002.
Santala M et al., entitled "Synthesis and breakdown of fibrillar collagens: concomitant phenomena in ovarian cancer," British Journal of Cancer 77(11):1825-1831, 1998, Abstract Only.
Li T et al., entitled "Inhibiting Ras signaling in the therapy of breast cancer," Cinical Breast Cancer 3(6):405-416, 2003, Abstract Only.
Thigpen J T, entitled "Chemotherapy for advanced ovarian cancer: overview of randomized trails," Semin. Oncol. 27(3 Suppl7):11-16, 2000, Abstract Only.
Supplementary European Search Report dated Jun. 2, 2008 for Application No. EP 05807467.5, 2 pages.
Goswami S. et al., entitled "Breast Cancer Cells Isolated by Chemotaxis from Primary Tumors Show Increased Survival and Resistance to Chemotherapy," Cancer Research, Nov. 1, 2004, vol. 64, pp. 7664-7667.
Santala M et al., entitled "Synthesis and breakdown of fibrillar collagens: concomitant phenomena in ovarian cancer," British Journal of Cancer (1998) 77(11), 1825-1831.
Thigpen J T, entitled "Chemotherapy for Advanced Ovarian Cancer: Overview of Randomized Trials," Seminars in Oncology, vol. 27, No. 3, Suppl 7 Jun. 2000, 11-16.
Li T et al., entitled "Inhibiting Ras Signaling in the Therapy of Breast Cancer," Clinical Breast Cancer, Feb. 2003, 405-416.

* cited by examiner

*Primary Examiner* — Karen Canella
(74) *Attorney, Agent, or Firm* — Amster, Rothstein & Ebenstein LLP

(57) ABSTRACT

Methods of isolating motile cells of interest from an animal tissue is provided. Also provided are methods of determining mRNA or protein expression of a gene in motile cells of interest from an animal tissue. Additionally, methods of determining whether a cancer in a tissue of a mammal is likely to metastasize are provided. Methods are also provided for inhibiting metastasis of a cancer in a tissue of a mammal. Further provided are methods of determining resistance of a motile cancer cell population in an animal tissue to a chemotherapeutic agent.

14 Claims, 11 Drawing Sheets

| Anti-apoptotic genes | | |
|---|---|---|
| Gene | Description | N/F |
| Ier3 | immediate early response 3 | 4.9 |
| Ubl1a2 | ubiquitin-like 1 (sentrin) activating enzyme subunit 2 | 4.7 |
| Txn | thioredoxin | 3.7 |
| Hsp105 | heat shock protein, 105 kDa | 3.5 |
| Odc | ornithine decarboxylase, structural | 3.0 |
| Dad1 | Defender against cell death 1 | 2.7 |
| Trp53 | transformation related protein 53 | 2.5 |
| Hsp60 | heat shock protein, 60 kDa | 2.4 |
| Api4 | apoptosis inhibitor 4 | 2.3 |
| Cldn3 | claudin 3 | 2.3 |
| Api5 | apoptosis inhibitor 5 | 2.3 |
| Hsp86-1 | heat shock protein, 86 kDa 1 | 2.1 |
| Api1 | apoptosis inhibitor 1 | 2.0 |
| Adam17 | a disintegrin and metalloproteinase domain 17 | 2.0 |
| Pro-apoptotic genes | | |
| Gene | Description | N/F |
| Pdcd4 | programmed cell death 4 | 0.1 |
| Fem1b | feminization 1 b homolog (C. elegans) | 0.4 |
| Apaf1 | apoptotic protease activating factor 1 | 0.6 |
| Pdcd8 | programmed cell death 8 (apoptosis inducing factor) | 0.8 |
|  | Cellular apoptosis susceptibility protein | 1.1 |
|  | ESTs. Highly similar to apoptosis specific protein | 1.1 |
|  | Apoptosis-associated spec-like protein containing CARD | 1.2 |
| AIF | Apoptosis-inducing factor AIF | 1.3 |

B

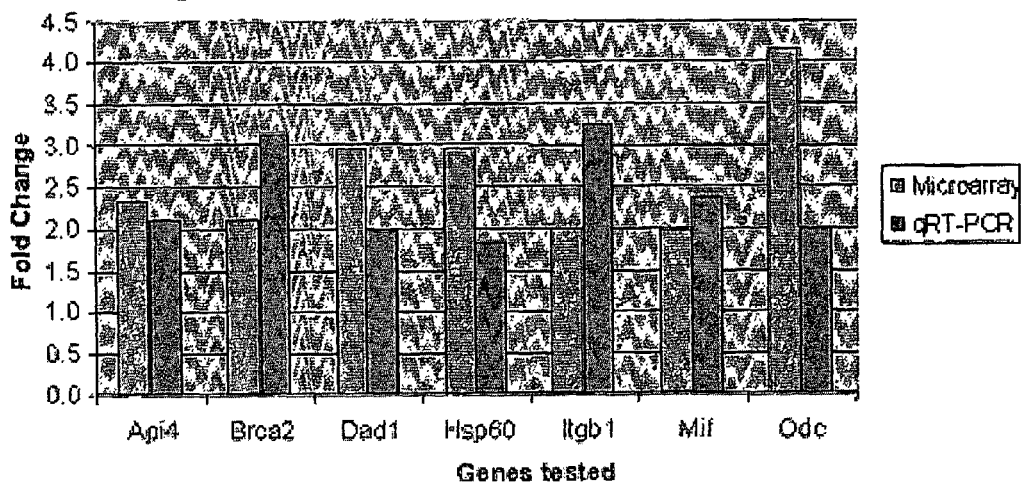

Comparison between Microarray and Realtime RT-PCR

FIG. 5
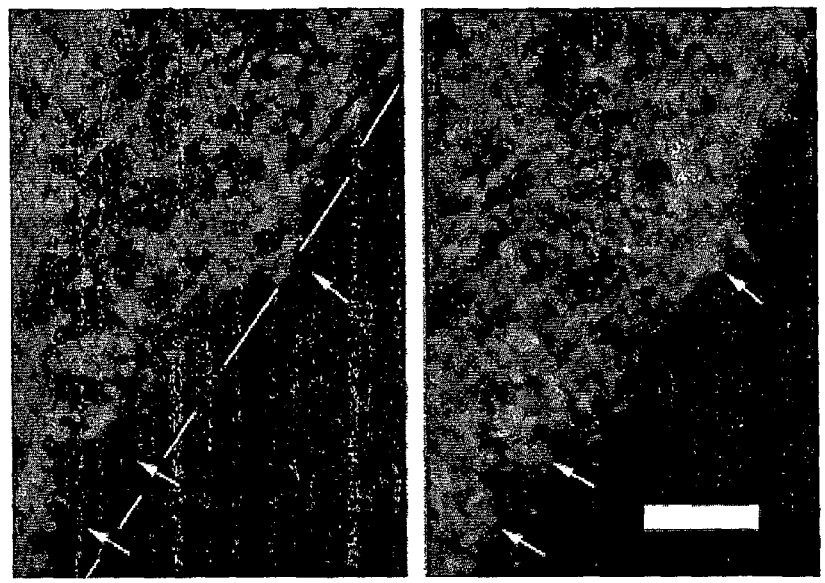
A
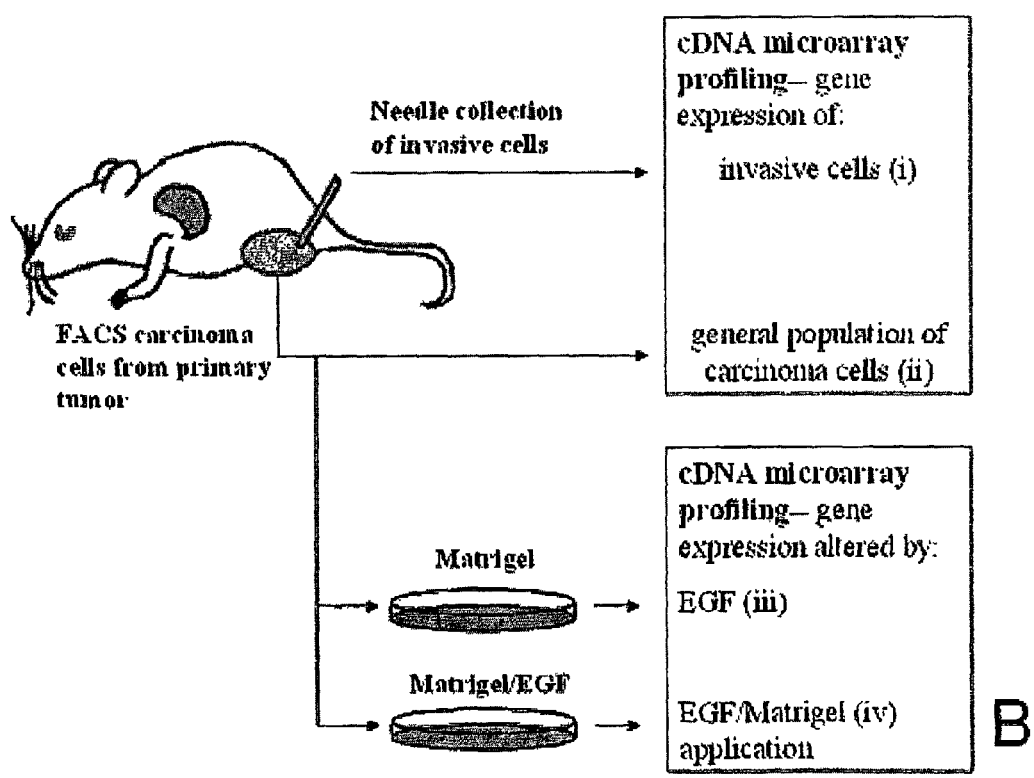
B

FIG. 9
A.
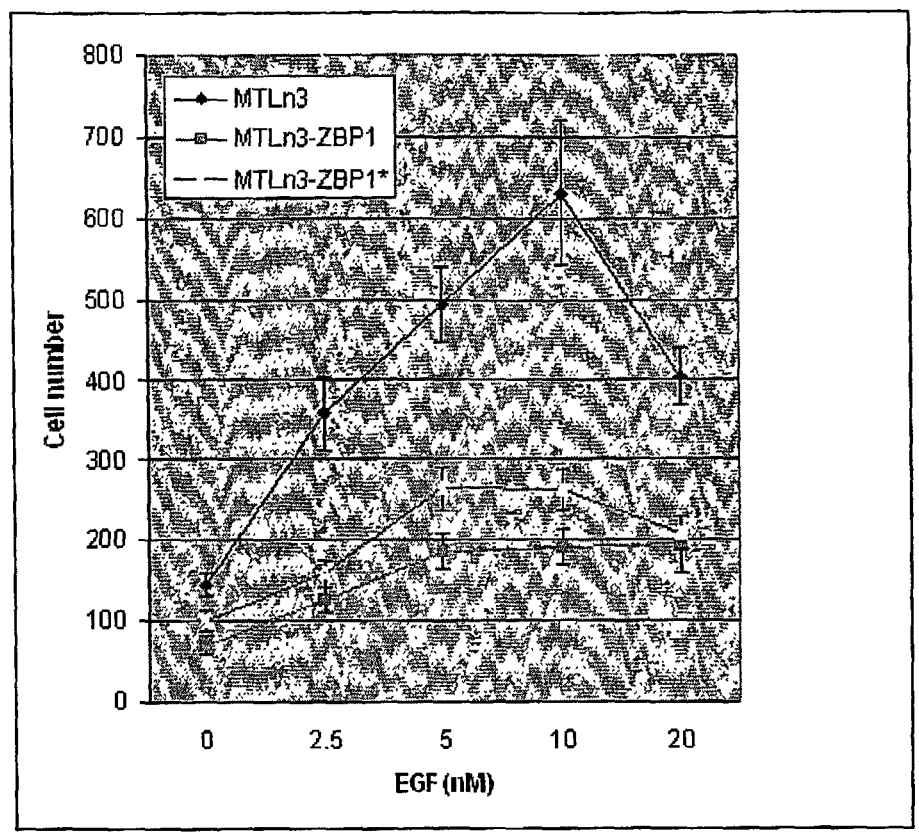
B.
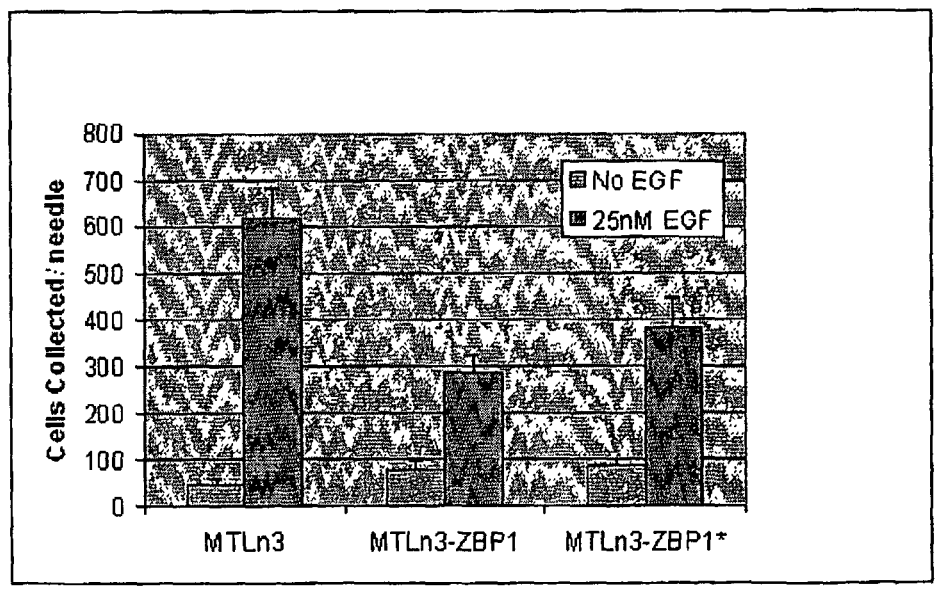

FIG. 10
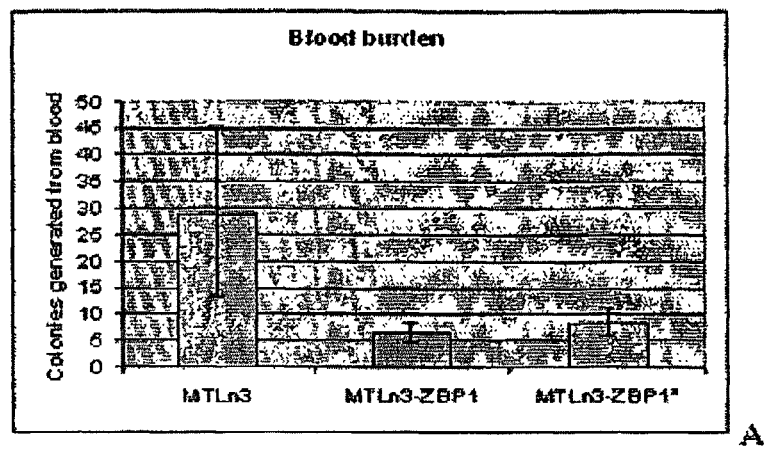
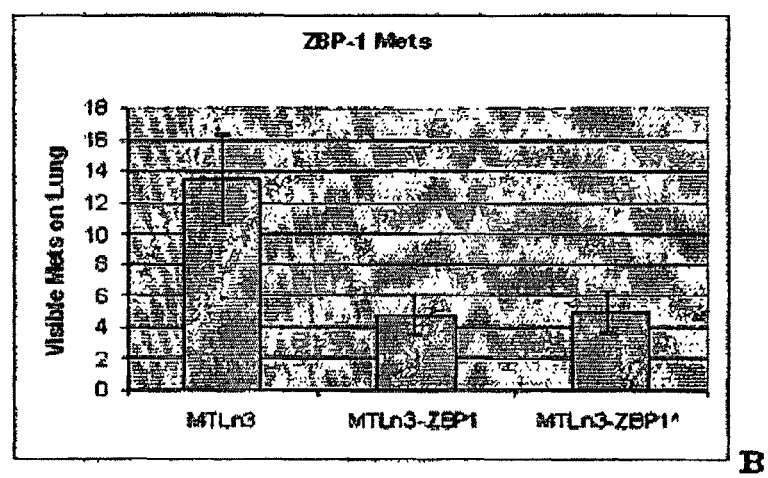
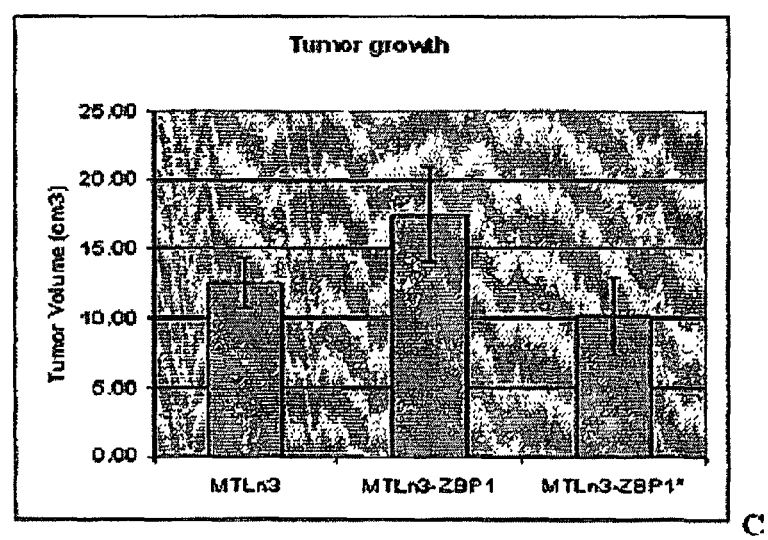

ISOLATION, GENE EXPRESSION, AND CHEMOTHERAPEUTIC RESISTANCE OF MOTILE CANCER CELLS

CROSS-REFERENCE TO RELATED APPLICATION

This is a U.S. national phase of PCT Application No. PCT/US2005/027680 filed Aug. 4, 2005, which claims the benefit of U.S. Provisional Application No. 60/600,697, filed Aug. 11, 2004.

STATEMENT OF GOVERNMENT SUPPORT

This invention was made with government support under grant numbers CA089829 and CA 100324 awarded by the National Institutes of Health. The government has certain rights in the invention.

BACKGROUND (1) Field of the Invention

The present invention generally relates to the characterization of motile cells and invasive cells of tumors. More specifically, the invention is directed to methods of isolating motile cells, in particular invasive cells, and the characterization of gene expression in those cells.

(2) Description of the Related Art

References Cited

Awada, A., Cardoso, F., Atalay, G., Giuliani, R., Mano, M., and Piccart, M. J. The pipeline of new anticancer agents for breast cancer treatment in 2003. Crit Rev Oncol Hematol, 48: 45-63, 2003.

Bailly, M. and Condeelis, J. Cell motility: insights from the backstage. Nat Cell Biol, 4: E292-294, 2002.

Bailly, M., Ichetovkin, I., Grant, W., Zebda, N., Machesky, L. M., Segall, J. E., and Condeelis, J. The F-actin side binding activity of the Arp2/3 complex is essential for actin nucleation and lamellipod extension. Curr Biol, 11: 620-625, 2001.

Bear, J. E., Svitkina, T. M., Krause, M., Schafer, D. A., Loureiro, J. J., Strasser, G. A., Maly, I. V., Chaga, O. Y., Cooper, J. A., Borisy, G. G., and Gertler, F. B. Antagonism between Ena/VASP proteins and actin filament capping regulates fibroblast motility. Cell, 109: 509-521, 2002.

Bonner, R. F., Emmert-Buck, M., Cole, K., Pohida, T., Chuaqui, R., Goldstein, S., and Liotta, L. A. Laser capture microdissection: molecular analysis of tissue. Science, 278: 1481, 1483, 1997.

Brakebusch, C., Wennerberg, K., Krell, H. W., Weidle, U. H., Sallmyr, A., Johansson, S., and Fassler, R. Beta1 integrin promotes but is not essential for metastasis of ras-myc transformed fibroblasts. Oncogene, 18: 3852-3861, 1999.

Bravo, S. B., Pampin, S., Cameselle-Teijeiro, J., Carneiro, C., Dominguez, F., Barreiro, F., and Alvarez, C. V. TGF-beta-induced apoptosis in human thyrocytes is mediated by p27kip1 reduction and is overridden in neoplastic thyrocytes by NF-kappaB activation. Oncogene, 22: 7819-7830, 2003.

Chambers, A. F., Groom, A. C., and MacDonald, I. C. Dissemination and growth of cancer cells in metastatic sites. Nat Rev Cancer, 2: 563-572, 2002.

Chan, A. Y., Bailly, M., Zebda, N., Segall, J. E., and Condeelis, J. S. Role of cofilin in epidermal growth factor-stimulated actin polymerization and lamellipod protrusion. J Cell Biol, 148: 531-542, 2000.

Clark, E. A., Golub, T. R., Lander, E. S., and Hynes, R. O. Genomic analysis of metastasis reveals an essential role for RhoC. Nature, 406: 532-535, 2000.

Condeelis, J. and Segall, J. E. Intravital imaging of cell movement in tumours. Nat Rev Cancer, 3: 921-930, 2003.

Condeelis, J., Song, X., Backer, J., Wyckoff, J., and Segall, J. Chemotaxis of cancer cells during invasion and metastasis. In: 5th Abercrombie Symposium on Cell Behaviour, St. Catherine's College, Oxford, UK, 2003.

Cooper, J. A. and Schafer, D. A. Control of actin assembly and disassembly at filament ends. Curr Opin Cell Biol, 12: 97-103, 2000.

Coulombe, P. A. and Omary, M. B. 'Hard' and 'soft' principles defining the structure, function and regulation of keratin intermediate filaments. Curr Opin Cell Biol, 14: 110-122, 2002.

Dal Canto, R. A., Shaw, M. K., Nolan, G. P., Steinman, L., and Fathman, C. G. Local delivery of TNF by retrovirus-transduced T lymphocytes exacerbates experimental autoimmune encephalomyelitis. Clin Immunol, 90: 10-14, 1999.

Davila, M., Frost, A. R., Grizzle, W. E., and Chakrabarti, R. LIM Kinase 1 Is Essential for the Invasive Growth of Prostate Epithelial Cells: IMPLICATIONS IN PROSTATE CANCER. J Biol Chem, 278: 36868-36875, 2003.

Edwards, D. C., Sanders, L. C., Bokoch, G. M., and Gill, G. N. Activation of LIM-kinase by Pak1 couples Rac/Cdc42 GTPase signalling to actin cytoskeletal dynamics. Nat Cell Biol, 1: 253-259, 1999.

Evan, G. I. and Vousden, K. H. Proliferation, cell cycle and apoptosis in cancer. Nature, 411: 342-348, 2001.

Farina, A. R., Coppa, A., Tiberio, A., Tacconelli, A., Turco, A., Colletta, G., Gulino, A., and Mackay, A. R. Transforming growth factor-beta1 enhances the invasiveness of human MDA-MB-231 breast cancer cells by up-regulating urokinase activity. Int J Cancer, 75: 721-730, 1998a.

Farina, K. L., Wyckoff, J. B., Rivera, J., Lee, H., Segall, J. E., Condeelis, J. S., and Jones, J. G. Cell motility of tumor cells visualized in living intact primary tumors using green fluorescent protein. Cancer Res, 58: 2528-2532, 1998b.

Farina, K. L., Huttelmaier, S., Musunuru, K., Darnell, R., and Singer, R. H. Two ZBP1 KH domains facilitate beta-actin mRNA localization, granule formation, and cytoskeletal attachment. J Cell Biol, 160: 77-87, 2003.

Fidler, I. J. and Kripke, M. L. Metastasis results from preexisting variant cells within a malignant tumor. Science, 197: 893-895, 1977.

Hanahan, D. and Weinberg, R. A. The hallmarks of cancer. Cell, 100: 57-70, 2000.

Huigsloot, M., Tijdens, I. B., Mulder, G. J., and van de Water, B. Differential regulation of doxorubicin-induced mitochondrial dysfunction and apoptosis by Bcl-2 in mammary adenocarcinoma (MTLn3) cells. J Biol Chem, 277: 35869-35879, 2002.

Iijima, M., Huang, Y. E., and Devreotes, P. Temporal and spatial regulation of chemotaxis. Dev Cell, 3: 469-478, 2002, Jolly, C. and Morimoto, R. I. Role of the heat shock response and molecular chaperones in oncogenesis and cell death. J Natl Cancer Inst, 92: 1564-1572, 2000.

Kang, Y., Siegel, P. M., Shu, W., Drobnjak, M., Kakonen, S. M., Cordon-Cardo, C., Guise, T. A., and Massague, J. A multigenic program mediating breast cancer metastasis to bone. Cancer Cell, 3: 537-549, 2003.

Larsen, M., Tremblay, M. L., and Yamada, K. M. Phosphatases in cell-matrix adhesion and migration. Nat Rev Mol Cell Biol, 4: 700-711, 2003.

LeBedis, C., Chen, K., Fallavollita, L., Boutros, T., and Brodt, P. Peripheral lymph node stromal cells can promote growth and tumorigenicity of breast carcinoma cells through the release of IGF-I and EGF. Int J Cancer, 100: 2-8, 2002.

Lin, M. and Van Golen, K. L. Rho-regulatory proteins in breast cancer cell motility and invasion. Breast Cancer Res Treat, 84: 49-60, 2004.

Lin, E. Y., Nguyen, A. V., Russell, R. G., and Pollard, J. W. Colony-stimulating factor 1 promotes progression of mammary tumors to malignancy. J Exp Med, 193: 727-740, 2001.

Lin, E. Y., Gouon-Evans, V., Nguyen, A. V., and Pollard, J. W. The macrophage growth factor CSF-1 in mammary gland development and tumor progression. J Mammary Gland Biol Neoplasia, 7: 147-162, 2002.

Liotta, L. A. and Kohn, E. C. The microenvironment of the tumour-host interface. Nature, 411: 375-379, 2001.

Loisel, T. P., Boujemaa, R., Pantaloni, D., and Carlier, M. F. Reconstitution of actin-based motility of Listeria and Shigella using pure proteins. Nature, 401: 613-616, 1999.

Mariadason, J. M., Arango, D., Corner, G. A., Aranes, M. J., Hotchkiss, K. A., Yang, W., and Augenlicht, L. H. A gene expression profile that defines colon cell maturation in vitro. Cancer Res, 62: 4791-4804, 2002.

Mogilner, A. and Edelstein-Keshet, L. Regulation of actin dynamics in rapidly moving cells: a quantitative analysis. Biophys J, 83: 1237-1258, 2002.

Nicholson, R. I., Gee, J. M., and Harper, M. E. EGFR and cancer prognosis. Eur J Cancer, 37 Suppl 4: S9-15, 2001.

Nishitani, H. and Lygerou, Z. Control of DNA replication licensing in a cell cycle. Genes Cells, 7: 523-534, 2002.

Ohashi, K., Nagata, K., Maekawa, M., Ishizaki, T., Naruamiya, S., and Mizuno, K. Rho-associated kinase ROCK activates LIM-kinase 1 by phosphorylation at threonine 508 within the activation loop. J Biol Chem, 275: 3577-3582, 2000.

O'Sullivan, C., Lewis, C. E., Harris, A. L., and McGee, J. O. Secretion of epidermal growth factor by macrophages associated with breast carcinoma. Lancet, 342: 148-149, 1993.

Parent, C. A. and Devreotes, P. N. A cell's sense of direction. Science, 284: 765-770, 1999.

Ramaswamy, S., Ross, K. N., Lander, E. S., and Golub, T. R. A molecular signature of metastasis in primary solid tumors. Nat Genet, 33: 49-54, 2003.

Real, P. J., Sierra, A., De Juan, A., Segovia, J. C., Lopez-Vega, J. M., and Fernandez-Luna, J. L. Resistance to chemotherapy via Stat3-dependent overexpression of Bcl-2 in metastatic breast cancer cells. Oncogene, 21: 7611-7618, 2002.

Reed, J. C. Apoptosis-targeted therapies for cancer. Cancer Cell, 3: 17-22, 2003.

Ree, A. H., Engebraaten, O., Hovig, E., and Fodstad, O. Differential display analysis of breast carcinoma cells enriched by immunomagnetic target cell selection: gene expression profiles in bone marrow target cells. Int J Cancer, 97: 28-33, 2002.

Sahai, E. and Marshall, C. J. Differing modes of tumour cell invasion have distinct requirements for Rho/ROCK signalling and extracellular proteolysis. Nat Cell Biol, 5: 711-719, 2003.

Sahai, E., Olson, M. F., and Marshall, C. J. Cross-talk between Ras and Rho signalling pathways in transformation favours proliferation and increased motility. EMBO J, 20: 755-766, 2001.

Segall, J. E., Tyerech, S., Boselli, L., Masseling, S., Helft, J., Chan, A., Jones, J., and Condeelis, J. EGF stimulates lamellipod extension in metastatic mammary adenocarcinoma cells by an actin-dependent mechanism. Clin Exp Metastasis, 14: 61-72, 1996.

Shestakova, E. A., Wyckoff, J., Jones, J., Singer, R. H., and Condeelis, J. Correlation of beta-actin messenger RNA localization with metastatic potential in rat adenocarcinoma cell lines. Cancer Res, 59: 1202-1205, 1999.

Shestakova, E. A., Singer, R. H., and Condeelis, J. The physiological significance of beta-actin mRNA localization in determining cell polarity and directional motility. Proc Natl Acad Sci USA, 98: 7045-7050, 2001.

Tomasovic, S. P., Rosenblatt, P. L., Johnston, D. A., Tang, K., and Lee, P. S. Heterogeneity in induced heat resistance and its relation to synthesis of stress proteins in rat tumor cell clones. Cancer Res, 44: 5850-5856, 1984.

Tusher, V. G., Tibshirani, R., and Chu, G. Significance analysis of microarrays applied to the ionizing radiation response. Proc Natl Acad Sci USA, 98: 5116-5121, 2001.

Van Waes, C., Surh, D. M., Chen, Z., Kirby, M., Rhim, J. S., Brager, R., Sessions, R. B., Poore, J., Wolf, G. T., and Carey, T. E. Increase in suprabasilar integrin adhesion molecule expression in human epidermal neoplasms accompanies increased proliferation occurring with immortalization and tumor progression. Cancer Res, 55: 5434-5444, 1995.

Wang, W., Wyckoff, J. B., Frohlich, V. C., Oleynikov, Y., Huttelmaier, S., Zavadil, J., Cennak, L., Bottinger, E. P., Singer, R. H., White, J. G., Segall, J. E., and Condeelis, J. S. Single Cell Behavior in Metastatic Primary Mammary Tumors Correlated with Gene Expression Patterns Revealed by Molecular Profiling Cancer Res, 62: 6278-6288, 2002.

Wang, W., Wyckoff, J. B., Wang, Y., Bottinger, E. P., Segall, J. E., and Condeelis, J. S. Gene expression analysis on small numbers of invasive cells collected by chemotaxis from primary mammary tumors of the mouse. BMC Biotechnol, 3: 13, 2003.

Wyckoff, J. B., Jones, J. G., Condeelis, J. S., and Segall, J. E. A critical step in metastasis: in vivo analysis of intravasation at the primary tumor. Cancer Res, 60: 2504-2511, 2000a.

Wyckoff, J. B., Segall, J. E., and Condeelis, J. S. The collection of the motile population of cells from a living tumor. Cancer Res, 60: 5401-5404, 2000b.

Yoshioka, K., Foletta, V., Bernard, O., and Itoh, K. A role for LIM kinase in cancer invasion. Proc Natl Acad Sci USA, 100: 7247-7252, 2003.

Zebda, N., Bernard, O., Bailly, M., Welti, S., Lawrence, D. S., and Condeelis, J. S. Phosphorylation of ADF/cofilin abolishes EGF-induced actin nucleation at the leading edge and subsequent lamellipod extension. J Cell Biol, 151: 1119-1128, 2000.

Zhao, H., Hastie, T., Whitfield, M. L., Borresen-Dale, A. L., and Jeffrey, S. S. Optimization and evaluation of T7 based RNA linear amplification protocols for cDNA microarray analysis. BMC Genomics, 3: 31, 2002.

Zhu, Y. Y., Machleder, E. M., Chenchik, A., Li, R., and Siebert, P. D. Reverse transcriptase template switching: a SMART approach for full-length cDNA library construction. Biotechniques, 30: 892-897, 2001.

Zigeuner, R., Ratschek, M., Rehak, P., Schips, L., and Langner, C. Value of p53 as a prognostic marker in histologic subtypes of renal cell carcinoma: a systematic analysis of primary and metastatic tumor tissue. Urology, 63: 651-655, 2004.

Understanding how cancer cells spread from the primary tumor is important for improving diagnostic, prognostic and therapeutic approaches that allow control of cancer metastasis. Alterations in gene expression along with protein activation by cancer cells leads to transformation, proliferation, invasion, intravasation, dissemination in blood or lymphatic vessels and eventually growth of distant metastases. In order for a tumor cell to become metastatic, it must be able to survive in the circulation and respond appropriately to new environments. This includes being able to migrate both within and beyond the primary tumor, in and out of blood and lymph vessels, and to utilize growth factors available at the site of metastasis for attachment and growth (Lin and Van Golen, 2004).

We have studied the motility-associated behavior of metastatic and non-metastatic mammary tumor cell lines by intravital imaging within primary tumors (Farina et al., 1998a; Wang et al., 2002; Wyckoff et al., 2000a). These studies have shown that the metastatic cells migrate to blood vessels and intravasate in a series of steps that involve active cell motility and may involve chemotaxis (Wang et al., 2002; Wyckoff et al., 2000a; Condeelis and Segall, 2003).

Many of the formative steps that determine the invasive and metastatic potential of carcinoma cells occur within the primary tumor. Much evidence suggests that the progress of cells from normal to invasive and then to metastatic involves progressive transformation through multiple genetic alterations selected by the tumor microenvironment (Hanahan and Weinberg, 2000). To identify the steps in progression and the genes involved in metastasis, recent emphasis has been on the use of molecular arrays to identify expression signatures in whole tumors with differing metastatic potential (Liotta and Kohn, 2001). A well recognized problem here is that primary tumors show extensive variation in properties with different regions of the tumor having different growth, histology, and metastatic potential and where only a small subset of cells within the parental tumor population may be capable of metastasizing (Fidler and Kripke, 1977). The array data derived from whole tumors results inevitably in averaging of the expression of different cell types from all of these diverse regions. The expression signature of invasive tumor cells, arguably the population essential for metastasis, may be masked or even lost because of the contribution of surrounding cells which represent the bulk of the tumor mass. Even so, recent studies of expression profiling of primary tumors suggest that the metastatic potential of tumors is encoded in the bulk of a primary tumor, thus challenging the notion that metastases arise from rare cells within a primary tumor acquired late during tumor progression (Ramaswamy et al., 2003).

This leaves us with a conundrum concerning the contribution of rare cells to the metastatic phenotype. The relative contribution of subpopulations of cells to the invasive and metastatic phenotype of primary tumors has not been assessed due to the difficulty in isolating phenotypically distinct cell populations from whole tumors. In addition, the metastatic cascade has been studied most heavily at the level of extravasation and beyond using experimental metastasis models removing the primary tumor from scrutiny. Thus, the microenvironment of the primary tumor that contributes to invasion and intravasation, and the process of selection of metastatic cells, has not been studied directly (Chambers et al., 2002).

In this context it has become important to develop technologies to separate pure populations of invasive cancer cells for gene expression studies. To this end, the development of Laser Capture Microdissection (LCM) has been an important advance (Bonner et al., 1997). However, the identification of cells within the tumor relies on morphology within fixed tissue making uncertain the identity of the collected cells and their behavior within the tumor before fixation. Alternative approaches involve the collection of cells from metastatic tumors and their expansion in culture (Clark et al., 2000; Kang et al., 2003; Ree et al., 2002). The pitfall of these approaches is that during culturing, the gene expression patterns may change to represent the in vitro culture conditions which are likely to be irrelevant to invasion in vivo.

SUMMARY OF THE INVENTION

Accordingly, the inventor has developed methods of isolating motile cells from animal tissues, and the use of those methods to isolate metastatic cells from cancerous tissue and quantify expression of various genes in those cells.

Thus, in some embodiments, the invention is directed to methods of isolating motile cells of interest from an animal tissue, where the animal tissue comprises the motile cells of interest and other motile cells. The methods comprise obtaining a microneedle or capillary filled with a porous matrix comprising a chemotactic factor; inserting the microneedle or capillary into the tissue for a time sufficient for the motile cells of interest to migrate into the porous matrix; expelling the porous matrix with motile cells from the microneedle or capillary; combining the porous matrix with microbeads, where the microbeads comprise a binding partner to a surface marker present on the other motile cells but not the motile cells of interest; and removing the microbeads.

In other embodiments, the invention is directed to methods of determining mRNA or protein expression of a gene in motile cells of interest from an animal tissue. The methods comprise isolating the motile cells of interest by the method described above, then extracting the mRNA or protein from the cells of interest, then determining mRNA or protein expression in the extraction of the cells of interest.

The invention is also directed to methods of determining whether a cancer in a tissue of a mammal is likely to metastasize. The methods comprise obtaining a microneedle or capillary filled with a porous matrix comprising a chemotactic factor; inserting the microneedle into the cancer for a time sufficient for motile cells to migrate into the porous matrix; expelling the porous matrix with motile cells from the microneedle; combining the porous matrix with microbeads, where the microbeads comprise a binding partner to a surface marker present on macrophages from the tissue; removing the microbeads; and quantifying the motile cells, where the presence of more motile cells than from the tissue when noncancerous or when comprising a non-metastatic cancer indicates that the cancer in the tissue of the mammal is likely to metastasize.

In further embodiments, the invention is directed to methods of inhibiting metastasis of a cancer in a tissue of a mammal. The methods comprise enhancing ZBP-1 activity in the tissue.

The invention is additionally directed to methods of inhibiting metastasis of a cancer in a tissue of a mammal. The methods comprise reducing the presence or activity of a protein in the tissue, where the protein is selected from the group consisting of Arp2/3 p16 subunit, Arp2/3 p21 subunit, alpha subunit of capping protein, beta subunit of capping protein, cofilin, WAVE3, ROCK1, ROCK2, LIMK 1, PKCζ, LIM-kinase, PAK, type II alpha isoform of PI4, 5 kinase, mena, tropomyosin, calpain, gelsolin-like protein (CAPG), zyxin, vinculin, and integrin 1.

The invention is further directed to methods of determining resistance of a motile cancer cell population in an animal tissue to a chemotherapeutic agent. The methods comprise obtaining the motile cancer cell population by the method described above; contacting the motile cancer cell population with the chemotherapeutic agent at a concentration and for a time sufficient to cause apoptosis in cancer cells susceptible to the chemotherapeutic agent; and determining apoptosis in the motile cancer cell population. In these embodiments, less apoptosis in the motile cancer cell population indicates that the motile cancer cell population is resistant to the chemotherapeutic agent.

BRIEF DESCRIPTION OF THE DRAWINGS

FIG. 2, Panel A is a chart indicating the relative overexpression and underexpression of pro-apoptotic and anti-apoptotic genes respectively. N/F shows the relative ratios of the gene expression of invasive cells over the general population. Panel B is a graph showing validation of microarray results for selected genes by quantitative real time PCR (QRT-PCR). Real time PCR was performed by using the ABI 7700 and SYBR Green PCR Core Reagents system (Applied Biosystems Foster City, Calif.) along with sequence-specific primer pairs for all genes tested. Results were evaluated with the ABI Prism SDS 2.0 software. Comparison of expression analyses in needle collected invasive tumor cells gives similar results for cDNA microarrays and QRT-PCR.

FIG. 5 is micrographs and a diagram showing in vivo selection and gene expression analysis of the highly invasive subpopulation of breast cancer cells collected by chemotaxis. Panel A shows multi-photon images of a live cell collection from an MTLn3 derived tumor. GFP-expressing carcinoma cells are seen moving toward the bevel (dashed line delineates edge) of a microneedle filled with matrigel and 25 nM EGF. Arrows indicate the final location of invading cells in both frames over the time lapse interval. Scale bar=25 µm. Panel B shows a schematic representation of the chemotaxis based selection process. MTLn3-derived mammary tumors in rats and the microneedle collection method were used to study the gene expression pattern of invasive subpopulation of carcinoma cells within live primary tumors. FACS sorting based on GFP expression in tumor cells was performed to isolate the general population of carcinoma cells from primary tumor, RNA extraction, probe labeling and microarray analysis were carried out. Carcinoma cells from primary tumor were FACS sorted as described above. The resulting cells were split and plated on Mettek dish covered with matrigel (1:5) in the presence (iv) or absence of 1 nM EGF (iii) for 4 hr at 37° C. The cells were then lysed directly on the dish for total RNA extraction, probe labeling and microarray analysis. Genes that were up- or downregulated on control experiments (comparison: iii vs. ii and iv vs. ii) were removed from the list of differentially expressed genes obtained when comparing i and ii. The resulting final list of 1366 genes is shown in Supplementary Table 4.

FIG. 9 is graphs showing the effect of ZBP-1 overexpression. Panel A shows that ZBP-1 over expression inhibits cell motility. Chemotaxis was measured in a Boyden chamber. ZBP-1 over expressing cells migrated through the filter in response to EGF poorly compared to the parental MTLn3 cells. Panel B shows that ZBP-1 over expression inhibits invasion as confirmed by the needle collection assay. The ability of carcinoma cells to invade microneedles placed into primary tumors derived from MTLn3 cells over expressing ZBP-1 was greatly reduced in ZBP-1 over expressing cells.

FIG. 10 is graphs showing ZBP-1 over expression inhibits tumor invasion and metastasis. ZBP-1 over expressing cells show lower metastatic potential. The number of tumor cells present in circulating blood (Panel A), and the number of lung metastatic tumors (Panel B) were greatly reduced in animals with tumors prepared with cells over expressing ZBP-1 ($p<0.05$, by Mann-Whitney Test). However, as shown in Panel C, tumor growth was not affected by increasing the expression of ZBP-1.

DETAILED DESCRIPTION OF THE INVENTION

Figure 1:
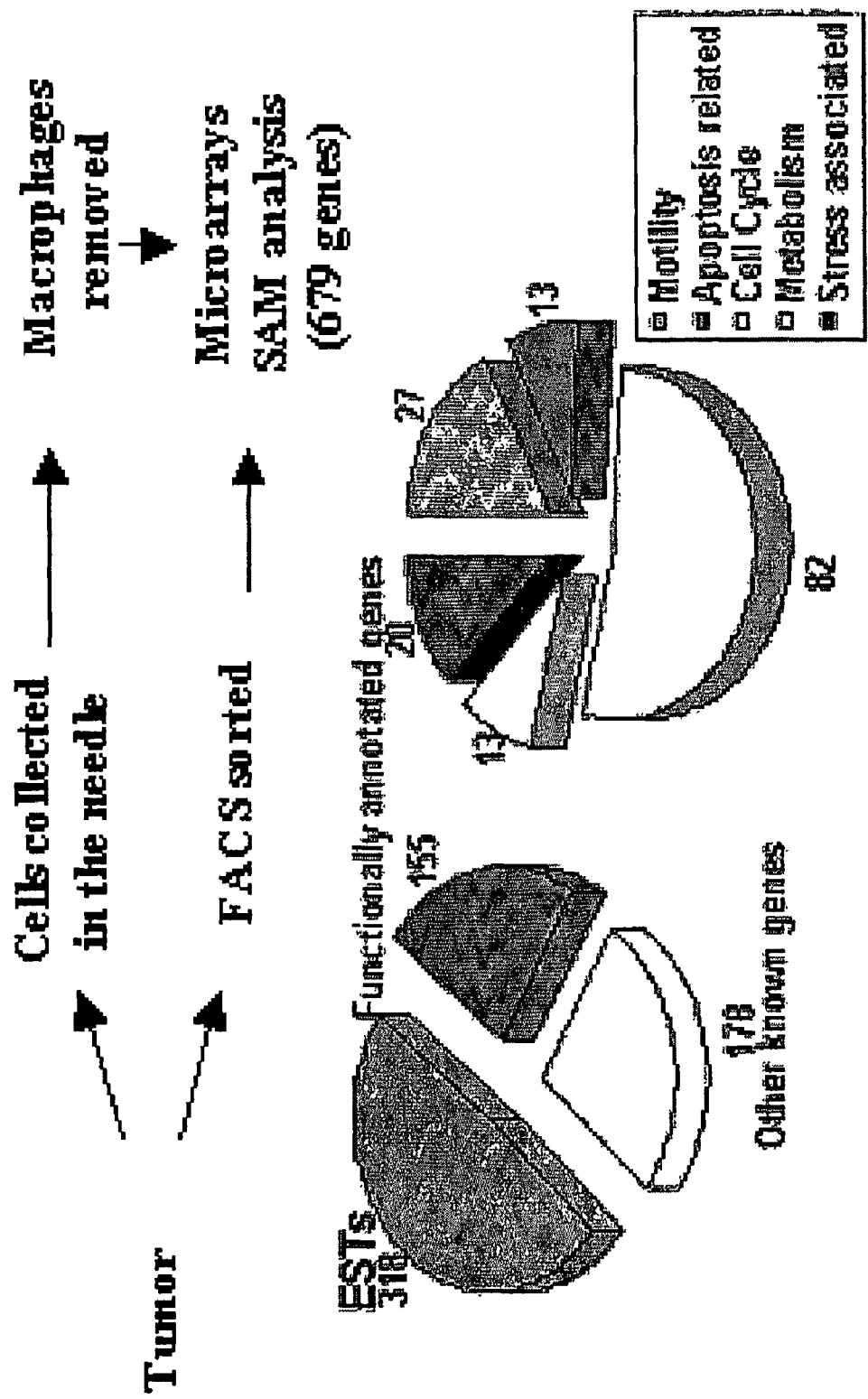
FIG. 1, top, is an illustration of a strategy for identification of gene expression patterns in invasive cells and their functional categories. MTLn3-derived mammary tumors in rats and the microneedle collection method were used to study the gene expression pattern of invasive subpopulation of carcinoma cells within live primary tumors. FACS sorting based on GFP expression in tumor cells was performed to isolate the general population of carcinoma cells from primary tumor, RNA extraction, probe labeling and microarray analysis were carried out as described in the Example 1 Materials and Methods. The resulting genelist from the SAM analysis is presented in Supplementary Table 1. The diagram at the bottom is a summary showing functional categories of the genes regulated in the invasive cells. The pie charts represent the relative proportion of genes (selected by SAM) in 6 categories based on their function using Gene-ontology Consortium classification.

The present invention is based on the development of methods of isolating motile cells, especially motile (metastatic) cancer cells from animal tissues, and the use of those methods to quantify expression of various genes in those motile cells.

Thus, in some embodiments, the invention is directed to methods of isolating motile cells of interest from an animal tissue, where the animal tissue comprises the motile cells of interest and other motile cells. The methods comprise obtaining a microneedle or capillary filled with a porous matrix comprising a chemotactic factor; inserting the microneedle or capillary into the tissue for a time sufficient for the motile cells of interest to migrate into the porous matrix; expelling the porous matrix with motile cells from the microneedle or capillary; combining the porous matrix with microbeads, where the microbeads comprise a binding partner to a surface marker present on the other motile cells but not the motile cells of interest; and removing the microbeads. Some preferred embodiments of these methods are described in Wang et al., 2003.

These methods can be used with tissue from any animal. Preferably, the animal is a vertebrate, more preferably a mammal, for example a rodent or a human.

Any tissue in the animal can be utilized in these methods, where the tissue has motile cells that are directed toward a chemotactic factor. Preferably, the issue is cancerous, since the isolation of motile cells from cancerous tissue is particularly useful, e.g., for determining the metastatic potential of the cancer. A non-limiting example of a tissue useful for these methods is mammary tissue. See examples.

The methods can be used with tissue in culture, tissue taken from a biopsy, or directly on tissue in a living mammal.

These methods are not narrowly limited to the use of any particular porous matrix. The matrix must only allow motile cells in the tissue to move through the matrix in response to the chemotactic factor. In preferred embodiments, the matrix is matrigel, since that matrix is similar chemically to vertebrate extracellular matrix.

The methods are also not limited to any particular microneedle or capillary; the microneedle or capillary must only be of sufficient bore to be capable of being filled with the porous matrix and to allow the motile cells to move into the matrix in response to the chemotactic factor. In some preferred embodiments, a microneedle is used; a preferred bore is 33-gauge.

Any binding partner capable of binding to the other motile cells but not the motile cells of interest, and capable of being bound (either covalently or noncovalently) to a microbead can be used. Nonlimiting examples include aptamers or, preferably, antibodies or antibody fragments, where the binding site is preferably specific for a cell surface marker present on the surface of the other motile cells but not the motile cells of interest. For example, where the motile cells of interest are carcinoma cells and the other motile cells are macrophages, a preferred microbead has antibodies specific for CD11b, which is present on the surface of macrophages but not carcinoma cells. See Wang et al., 2003. The skilled artisan could formulate a binding partner for any particular motile cell of interest/other motile cell combination without undue experimentation.

As used herein, "antibody" includes the well-known naturally occurring immunoglobulin molecules as well as fragments thereof that comprise a typical immunoglobulin antigen binding site (e.g., Fab or Fab2). The antibodies can be from a polyclonal, monoclonal, or recombinant source, and can be of any vertebrate (e.g., mouse, chicken, rabbit, goat or human), or of a mixture of vertebrates (e.g., humanized mouse).

These methods are also not narrowly limited to any particular microbeads for binding the other motile cells. For example, the microbeads can be heavy particles that are pelleted under centrifugal conditions that do not pellet the motile cells of interest. Alternatively, the microbeads can be buoyant particles that are not pelleted under centrifugal conditions that pellet the motile cells of interest. In preferred embodiments, the microbeads are colloidal super-paramagnetic beads as described in Wang et al., 2003.

The chemotactic factor can be any factor capable of attracting the motile cells of interest. Where the motile cells of interest are cancer cells, a preferred chemotactic factor is an epidermal growth factor.

Although the other motile cells in the examples herein and in Wang et al., 2003 are substantially macrophages, it is anticipated that other normal stromal cells such as fibroblasts or eosinophils may be predominant in other applications, e.g., where the cancer is in tissues other than mammary tissue. It is believed that the skilled artisan could easily identify binding partners that are effective for removal of any other motile cells without undue experimentation.

The motile cells of interest for these methods are not limited to cancer cells, and can be normal stromal cells such as macrophages. Additionally, the other motile cells (such as macrophages where the motile cells of interest are cancer cells) can be retained and further analyzed, since they are generally isolated in essentially pure form on the microbeads. The further analysis can include, e.g., quantitation of the cells, or analysis of mRNA or protein expression.

These methods are generally useful for isolating live motile cells of interest in highly enriched form, such that culture of the cells, and/or further analysis, can be performed. For example, the cells can be quantified, in order to approximate the number of motile cells of interest present in a given amount of tissue, or to compare the amount of motile cells of interest to the amount of the other motile cells.

In some preferred embodiments, mRNA or protein expression of at least one gene is determined in the motile cells of interest. See Example 2, where mRNA expression of various genes is quantified in the motile cells of interest (carcinoma cells) and compared with expression of the same genes in other carcinoma cells in the same tissue.

As shown in Example 2, motile breast carcinoma cells have significantly higher mRNA expression of Arp2/3 p16 subunit, Arp2/3 p21 subunit, alpha subunit of capping protein, beta subunit of capping protein, cofilin, WAVE3, ROCK1, ROCK2, LIMK 1, PKCζ, LIM-kinase, PAK, type II alpha isoform of PI4, 5 kinase, mena, tropomyosin, calpain, gelsolin-like protein (CAPG), zyxin, vinculin, integrin β1, tight junction protein 2, member Ras oncogene family, and epidermal growth factor receptor than nonmotile carcinoma cells from the same tissue, indicating involvement of these genes in the metastatic phenotype. Additionally, mRNA expression of ZBP-1, collagen type III α1, G-protein coupled receptor 26, and fibroblast growth factor receptor 1 is significantly reduced in motile breast carcinoma cells when compared to the nonmotile carcinoma cells, indicating a role of these proteins in regulation of metastasis. Additionally, when ZBP-1 is overexpressed in a carcinoma cell line, motility of the cells is greatly reduced (Example 2), further establishing the role of ZBP-1 in metastasis regulation. Thus, determination of protein, or, preferably, mRNA expression of any of those genes, especially ZBP-1 is particularly desirable.

As shown in Table 2 and the accompanying discussion in Example 2, motile cancer cells have a characteristic pattern of downregulation of collagen type III α1, G-protein coupled receptor 26, ZBP-1, and fibroblast growth factor receptor 1, and upregulation of Arp2/3 p16 subunit, tight junction protein 2, member Ras oncogene family, and epidermal growth factor receptor. Thus, it is also preferred that protein or, especially, mRNA expression is determined in at least two, and preferably all, of those genes.

When analysis of mRNA or protein expression of more than one gene is desired, microarray technology can be employed. This well-established technology can analyze mRNA or protein expression of many thousands of genes at once, allowing comparison of expression of, e.g., an entire genome between motile and non-motile cells.

These methods are capable of isolating a few hundred motile cells from a tissue. This typically provides 20-50 ng of total RNA, which is insufficient for array analysis. Therefore, the mRNA from these cells is preferably amplified prior to the determination of expression of the genes. Preferably, the amplification is by reverse transcription and cDNA amplification. A preferred method is the SMART PCR cDNA amplification method (ClonTech Laboratories). See Wang et al., 2003.

The motile cells of interest can also be tested for resistance to chemotherapeutic agents. See Example 1.

In other embodiments, the invention is directed to methods of determining mRNA or protein expression of a gene in motile cells of interest from an animal tissue. The methods comprise isolating the motile cells of interest by the method described above, then extracting the mRNA or protein from the cells of interest, then determining mRNA or protein expression in the extraction of the cells of interest. Preferably, mRNA or protein expression of more than one gene is determined, for example using a microarray by known methods.

When mRNA expression is determined using these methods, the mRNA is preferably extracted and amplified in the motile cells of interest, then mRNA expression of the gene(s) are determined from the amplified mRNA. As described above, the mRNA in these methods is preferably amplified by reverse transcription and cDNA amplification.

In these methods, the animal is preferably a vertebrate; more preferably the animal is a mammal, such as a rodent or a human.

These methods are particularly useful for analysis of motile cells of interest in cancerous tissue, for example carcinoma tissue, such as breast cancer in mammary tissue. See Example 2. As with the methods described above, these methods can be used with tissue in culture, tissue taken from a biopsy, or directly on tissue in a living mammal.

As discussed above, preferred genes for determination of protein or mRNA expression are Arp2/3 p16 subunit, Arp2/3 p21 subunit, alpha subunit of capping protein, beta subunit of capping protein, cofilin, WAVE3, ROCK1, ROCK2, LIMK 1, PKCζ, LIM-kinase PAK, type II alpha isoform of PI4, 5 kinase, mena, tropomyosin, calpain, gelsolin-like protein (CAPG), zyxin, vinculin, integrin β1, collagen type III α1, G-protein coupled receptor 26, ZBP-1, fibroblast growth factor receptor 1, tight junction protein 2, member Ras oncogene family, and epidermal growth factor receptor. In particular, mRNA expression of the group collagen type III α1, G-protein coupled receptor 26, ZBP-1, fibroblast growth factor receptor 1, Arp2/3 p16 subunit, tight junction protein 2, member Ras oncogene family, and epidermal growth factor receptor is desirable to identify a characteristic signature of metastasis.

The present invention is also directed to methods of determining whether a cancer in a tissue of a mammal is likely to metastasize. The method comprises obtaining a microneedle or capillary filled with a porous matrix comprising a chemotactic factor; inserting the microneedle into the cancer for a time sufficient for motile cells to migrate into the porous matrix; expelling the porous matrix with motile cells from the microneedle or capillary; combining the porous matrix with microbeads, where the microbeads comprise a binding partner to a surface marker present on macrophages from the tissue; removing the microbeads; and quantifying the motile cells, where the presence of more motile cells than from the tissue when noncancerous or when comprising a non-metastatic cancer indicates that the cancer in the tissue of the mammal is likely to metastasize. Since the motile cell isolation method isolates metastatic cells from cancerous tissue, the presence of more motile cells from a cancerous tissue than from a normal tissue establishes that the cancerous tissue as metastatic potential. These methods are useful for analyzing potentially metastatic cancer in any tissue. In some preferred embodiments, the tissue is mammary tissue, since breast carcinoma is often metastatic.

These methods can be used with any animal. Preferably, the animal is a mammal, such as a rodent or a human.

As established in Wang et al., 2003, and Example 2, where the cancer is a carcinoma, and in particular a breast cancer, common other motile cells in these methods are macrophages. In those cases, a preferred binding partner is an antibody is specific for CD11b. Additionally, where the cancer is a carcinoma, a preferred chemotactic factor is an epidermal growth factor.

The motile cells resulting from these methods can be quantified by any known method. Preferred methods include the use of a fluorescence-activated cell sorter, after labeling the cells with a fluorescent marker by known methods. Alternatively, the motile cells may be quantified by simple microscopic observation, e.g., with a hemocytometer.

As described above, the microneedle or capillary is a preferably a microneedle, and the porous matrix preferably comprises matrigel.

As established in Example 2, enhancing ZBP-1 activity in a cancerous tissue decreases the metastatic potential in that tissue. Also, since collagen type III α1, G-protein coupled receptor 26, and fibroblast growth factor receptor 1 are characteristically decreased in metastatic cells, decreasing the expression or activity of those proteins would also be expected to decrease the metastatic potential of cancer cells. Thus, the present invention is further directed to methods of inhibiting metastasis of a cancer in a tissue of a mammal. The methods comprise enhancing collagen type III α1, G-protein coupled receptor 26, fibroblast growth factor receptor 1, or especially ZBP-1 activity in the tissue. It is anticipated that these methods are particularly useful for treatment of breast cancer.

In some embodiments of these methods, the collagen type III α1, G-protein coupled receptor 26, ZBP-1, or fibroblast growth factor receptor 1 activity is enhanced by transfecting the tissue with a vector comprising a collagen type III α1, G-protein coupled receptor 26, ZBP-1, or fibroblast growth factor receptor 1 transgene, where the collagen type III α1, G-protein coupled receptor 26, ZBP-1, or fibroblast growth factor receptor 1 transgene is translated from the vector in the tissue. Such methods, and vectors for executing those methods, are well known in the art, and can be established by a skilled artisan without undue experimentation.

In other embodiments, the collagen type III α1, G-protein coupled receptor 26, ZBP-1, or fibroblast growth factor receptor 1 activity is enhanced by adding a pharmaceutical composition of collagen type III α1, G-protein coupled receptor 26, ZBP-1, or fibroblast growth factor receptor 1 protein to the tissue. Preferably, the pharmaceutical composition comprises an agent to enhance penetration of the collagen type III α1, G-protein coupled receptor 26, ZBP-1, or fibroblast growth factor receptor 1 protein into the cell, such as liposomes, etc., the use of which are well known in the art.

Example 2 also establishes that several genes are upregulated in metastatic tissue. It is therefore anticipated that metastasis can be inhibited by reducing the activity of these genes in a cancer having metastatic potential. Thus, the invention is additionally directed to methods of inhibiting metastasis of a cancer in a tissue of a mammal. The methods comprise reducing the presence or activity of a protein in the tissue, where the protein is a protein whose expression is upregulated in metastatic cells. Examples of such proteins are Arp2/3 p16 subunit, Arp2/3 p21 subunit, alpha subunit of capping protein, beta subunit of capping protein, cofilin, WAVE3, ROCK1, ROCK2, LIMK 1, PKCζ, LIM-kinase, PAK, type II alpha isoform of PI4, 5 kinase, mena, tropomyosin, calpain, gelsolin-like protein (CAPG), zyxin, vinculin, integrin β1, tight junction protein 2, member Ras oncogene family, and epidermal growth factor receptor.

The presence of any of these proteins can be reduced without undue experimentation by addition of an antisense molecule, a ribozyme, or an RNAi molecule to the tissue, where the antisense molecule, ribozyme or RNAi molecule specifically inhibits expression of the protein. In these embodiments, the antisense molecule, ribozyme, or RNAi molecule can be comprised of nucleic acid (e.g., DNA or RNA) or nucleic acid mimetics (e.g., phosphorothionate mimetics) as are known in the art. Methods for treating tissue with these compositions are also known in the art. In some embodiments, the antisense molecule, ribozyme or RNAi molecule can be added directly to the cancerous tissue in a pharmaceutical composition that preferably comprises an excipient that enhances penetration of the antisense molecule, ribozyme or RNAi molecule into the cells of the tissue. In other embodiments, the antisense molecule, ribozyme or RNAi is expressed from a vector that is transfected into the cancerous tissue. Such vectors are known in the art, and these embodiments can be developed for any of the subject proteins without undue experimentation.

In other embodiments, the presence or activity of the protein is reduced by addition of an antibody or aptamer to the tissue, wherein the antibody or aptamer specifically binds and reduces the activity of the protein in the tissue. The antibody or aptamer can be added directly to the tissue, preferably in a pharmaceutical composition comprising an agent that enhances penetration of the antibody or aptamer into the tissue. Alternatively, the antibody or aptamer can be encoded on a vector that is used to transfect the cancerous tissue.

Aptamers are single stranded oligonucleotides or oligonucleotide analogs that bind to a particular target molecule, such as a protein or a small molecule (e.g., a steroid or a drug, etc.). Thus, aptamers are the oligonucleotide analogy to antibodies. However, aptamers are smaller than antibodies, generally in the range of 50-100 nt. Their binding is highly dependent on the secondary structure formed by the aptamer oligonucleotide. Both RNA and single stranded DNA (or analog), aptamers are known.

Aptamers that bind to virtually any particular target can be selected by using an iterative process called SELEX, which stands for Systematic Evolution of Ligands by EXponential enrichment. Several variations of SELEX have been developed which improve the process and allow its use under particular circumstances. See the references cited in PCT/US04/15752, all of which are incorporated by reference.

The invention is further directed to methods of determining resistance of a motile cancer cell population in an animal tissue to a chemotherapeutic agent. The methods comprise obtaining the motile cancer cell population by the methods described above; contacting the motile cancer cell population with the chemotherapeutic agent at a concentration and for a time sufficient to cause apoptosis in cancer cells susceptible to the chemotherapeutic agent; and determining apoptosis in the motile cancer cell population. In these embodiments, less apoptosis in the motile cancer cell population indicates that the motile cancer cell population is resistant to the chemotherapeutic agent. See Example 1 for some preferred embodiments of these methods.

Examples of chemotherapeutic agents that can be utilized in these embodiments are doxorubicin, cisplatin, or etoposide.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Breast Cancer Cells Isolated by Chemotaxis from Primary Tumors Show Increased Survival and Resistance to Chemotherapy Example Summary A novel observation resulting from intravital imaging of these tumors is the dramatic fragmentation of carcinoma cells when in contact with blood vessels in non-metastatic tumors (Wyckoff et al., 2000a) compared with the ability of carcinoma cells in metastatic tumors to enter blood vessels as intact whole cells. This suggests a survival advantage for metastatic cells during migration and intravasation.

In the current study we have collected a migratory population of carcinoma cells by chemotaxis to EGF containing microneedles held in the primary tumor. The collected cells were subjected to microarray analysis for differential gene expression. The results show that anti-apoptotic genes are up regulated and pro-apoptotic genes are down regulated coordinately in the migratory subpopulation. Induction of apoptosis by doxorubicin, cisplatin and etoposide in these cells demonstrates that they exhibit a lower drug induced apoptotic index and lower cell death as compared to carcinoma cells of the whole tumor. Our study indicates, for the first time, the capability of using a rat allograft model for evaluating the apoptotic status of a migratory subpopulation of tumor cells and the ability to study their resistance to chemotherapeutic agents directly. In addition, these results indicate that tumor cells that are chemotactic and migratory in response to EGF in the primary tumor have a survival advantage over stationary tumor cells.

Introduction

Recently we have shown that microarray based gene expression studies can be successfully performed on cells collected by chemotaxis into microneedles held in the primary tumor (Wang et al., 2003). In the current example we have combined this method with the analysis of pro- and anti-apoptosis gene expression to determine if migratory cells in the primary tumor have a survival advantage over that of sedentary carcinoma cells within the same tumor. In addition, anticancer drugs designed against the proliferative property of cancer cells were used to investigate if the migratory cells respond equally to the antiproliferative drugs compared to their non-migratory counterparts.

Materials and Methods

Needle collection and FACS sorting of primary tumor cells. We used MTLn3-derived mammary tumors in rats (Farina et al., 1998a), and the microneedle collection method described previously (Wyckoff et al., 2000b; Wang et al., 2003), to study the gene expression pattern of invasive subpopulation of carcinoma cells within live primary tumors. Briefly, the invasive cells were collected from MTLn3 tumor using microneedles containing EGF. Macrophages were removed from this population by using MACS CD11b Microbeads (Miltenyi Biotec) as described before (Wang et al., 2003). The residual carcinoma cells were lysed for RNA extraction. To isolate the general population of carcinoma cells from primary tumor, a small piece tumor was minced, and filtered twice through a nylon-filter to obtain a single cell suspension. FACS sorting was performed on the resulting single cell suspensions based on their GFP expression in tumor cells using a Becton Dickinson (San Jose, Calif.) FACSVantage cell sorter. GFP-positive tumor cells were collected and lysed directly for RNA extraction. All the procedures were done on ice or 4° C.

RNA extraction and amplification. RNA extraction was performed using the RNeasy kit (QIAGEN), as per manufacturer's protocol and eluted with 30 µl RNase-free water. The total RNA was reverse-transcribed and amplified directly using the SMART PCR cDNA synthesis kit (Clontech, Palo Alto, Calif.) as described previously (Wang et al., 2003).

Use of pooled reference RNA as control. An equal quantity of reference RNA (pooled RNA from rat liver, spleen, brain and kidney, 4:2:1:1, Ambion Tex.) was used as a control in all our microarray experiments, which allowed us to use one of the channels as a hybridization control for all the spots on the microarray. The use of pooled reference RNA from the same species as the MTLn3 cells allowed the same interspecies cross hybridization as the background, allowing us to use Mouse cDNA microarrays for our experiments. The pooled reference RNA covers a very broad range of gene expression and is routinely used as controls in cDNA microarray studies (Zhao et al., 2002).

Probe labeling and microarray hybridization. After amplification, cDNAs were purified using the QIAquick PCR Purification Kit (Qiagen) and eluted with TE buffer. Labeling was performed using Label IT® (Mirus) following the manufacturer's instructions. Briefly, labeling reactions were prepared by mixing 10× Mirus Labeling Buffer A, purified cDNA and Cy5 (or Cy3) dye. After incubating the reaction mix at 37° C. for 1 hour, the two resulting probes were purified by passing through gel filteration columns. The purified probes were then combined and concentrated using Microcon columns. The concentrated cDNA probes were denatured at 94° C., and hybridized to an arrayed slide overnight at 50° C. Details of slide washing and image collection were described in previous studies (Wang et al., 2002; Wang et al., 2003).

Quality control and data analysis for microarrays. The scanned images were analyzed using the software Genepix (Axon Instruments, Inc. CA) and an absolute intensity value was obtained for both the channels. The entire raw data set was filtered to accommodate a requirement of at least 2 good quality measurements for each triplicate experiment. Values from only the good quality measurements (where the signal strength was more than twice the standard deviation of the background plus the background) were considered for further analysis. Two types of normalization were performed routinely in tandem on all the experiments using the GeneSpring software package (Silicon Genetics, Redwood City, Calif.). First, intensity-based-normalization was performed to take into consideration the overall signal strength of both channels and normalize the signal strength between all the different chips, reducing the chance of chip-to-chip variability. Second, a reference channel-based normalization was performed which takes into consideration the reference channel (which in this case is pooled reference RNA) and normalizes the values in all the spots. This reduces the chance of spot to spot variability. The final data was a result of both these types of normalization.

Significance analysis of microarrays. In order to determine the significance of up-regulated and down-regulated genes, we performed significance analysis using the software Significance Analysis of Microarrays (SAM) (8). Briefly after normalizing the data as mentioned above the data was log transformed to Log 2 and subjected to SAM analysis. The algorithm performs a significance analysis by comparing the relative variance of the replicates between the samples. The result were determined at 5% False Discovery Rate (FDR).

Real time PCR confirmation. To verify the data obtained from microarrays, QRT-PCR analysis of selected over expressed and under expressed genes was performed by using the ABI 7900 (Applied Biosystems, Foster City, Calif.) with sequence-specific primer pairs for all genes tested (see Supplement Table 2 for primer sequences, amplicon size and annealing temperature) as described previously (Wang et al., 2002). SYBR Green was used for real-time monitoring of amplification. Results were evaluated with the ABI Prism SDS 2.0 software. All the genes tested for regulation were compared to at least two housekeeping genes (Beta actin and GAPDH).

Cell culture and apoptosis assay. The cells extruded from the needles and tumor cells FACS sorted were cultured in DMEM 20% FCS along with streptomycin and penicillin, for 16 hrs. Subsequently, the cells were challenged with either doxorobucin (17 µM) or cisplatin (50 µM) or etoposide (50 µM) for 1 hr, washed and allowed to recover for 24 hrs. The cells were then subjected to an apoptosis assay kit containing Annexin V Cy5 for staining the apoptotic cells and Propedium Iodide (PI) for staining the dead cells (BD Biosciences San Jose, Calif.). After staining the cells using the manufacturer's protocol, the cells were observed under a fluorescent microscope in the green, red and high red channel for GFP, PI and Cy5 respectively. The total number of GFP cells counted was compared to the number of PI positive and Annexin V-Cy5 positive cells.

Results and Discussion

GFP-labeled tumor cells were injected into rat mammary fat pads, and primary tumors were allowed to grow for 2-2.5 weeks. To provide insight into the pattern of gene expression associated with chemotactic and migratory carcinoma cells in vivo, we compared the gene expression profile of a subpopulation of tumor cells collected from the primary tumor by chemotaxis into a microneedle, called the invasive cells, with that of the general population of GFP-expressing tumor cells sorted from the whole primary tumor by FACS sorting (FIG. 1). Differential gene expression analysis comparing the invasive and general populations of tumor cells was performed using SAM analysis at 5% FDR level revealing 679 genes that were differentially expressed significantly relative to all genes on the array (Supplementary Table 1). The genes that are previously known to be associated with the EGF response (28 genes) were removed from this population. As shown in FIG. 1, genes with known functions whose regulation was changed in the chemotactic and migratory population of cells in the primary tumor were divided into six different functional categories based on the definitions provided by the gene-ontology consortium (http://www.geneontology.org/). It was evident that amongst the functional categories mentioned here the largest change in the number of regulated genes was observed in the genes associated with the cell cycle indicating a large change in the cell proliferation pattern of migratory cells. A detailed scrutiny of these cells showed that the genes associated with increasing cell proliferation were down regulated and those genes associated with a reduction in cell proliferation were upregulated.

Another category of genes found to be significantly regulated in the chemotactic and migratory population of cells in the primary tumor is that of cell motility. These genes have been explained in detail in an accompanying paper. Since there are 5 steps of the motility cycle which are coordinated to assure efficient cell motility, the up regulation of genes for major effectors in the pathways of each step predicts that the invasive cells will have a heightened migratory activity compared to carcinoma cells of the general tumor population and this is consistent with the high velocities of migration seen in tumors (Condeelis and Segall, 2003).

Regulation of pro and anti-apoptotic genes along with mechanical stability genes. Of particular relevance to survival, stress and apoptosis associated genes showed large changes in regulation (FIG. 2). The up regulation of the heat shock proteins indicates a survival phenotype (Jolly and Morimoto, 2000). This is particularly interesting here as the MTLn3 cells used to generate the primary tumors in this study have been shown to over express heat shock proteins as compared to non-metastatic cell lines (MTC) derived from the same tumor (10). This indicates that in the chemotactic and migratory population of cells in the primary tumor there is a further up regulation of the heat shock gene expression over that in the MTLn3 cells used to generate the primary tumor.

A potential explanation for mechanical stability and survival advantage observed in invasive cells (Jolly and Morimoto, 2000; Condeelis et al., 2003) is the large relative over expression of cytokeratins by carcinoma cells and the suppression of apoptosis gene expression in metastatic tumors and cell lines (Wang et al., 2002). Keratins form the largest subfamily of intermediate filament proteins that play critical roles in the mechanical stability of epithelial cells subjected to shear forces (Coulombe and Omary, 2002). In addition, it was found that carcinoma cells in metastatic tumors and in culture express laminins and cadherins and apoptosis suppressor genes at high levels, all of which might contribute to survival during intravasation and in the circulation (Wang et al., 2002). In contrast, carcinoma cells in non-metastatic tumors and in culture express genes involved in programmed cell death at higher levels. The combination of these factors may contribute to the increased numbers of viable carcinoma cells in the circulation of metastatic tumors and to fragmentation during intravasation and cell death seen in non metastatic tumors (Wyckoff et al., 2000a; Condeelis et al., 2003).

In addition, the anti-apoptotic and pro-apoptotic genes are inversely regulated in the chemotactic and migratory population of cells in the primary tumor (FIG. 2A). The ratio of expression of each gene in the invasive cells, when compared to the general population indicates that a significant number of the anti-apoptotic genes were up regulated while the pro-apoptotic genes were unregulated or down regulated. This is consistent with a previous study where the apoptosis suppressor genes were up regulated in a cell line (MTLn3), which causes metastasis in vivo when compared to another cell line from the same lineage (MTC), which does not (Wang et al., 2002). In the current study we show a similar difference between the invasive and general populations of the primary tumor even though the tumor is derived from the same parental cells (MTLn3). This is important because it means that the microenvironment that induces the chemotactic and migratory behavior of tumor cells induces the survival expression pattern in cells with a previously identical genetic background. We verified the array results using real time PCR for selected genes belonging to the functional category of apoptosis. As shown in FIG. 2B, the same pattern of expression was observed in the invasive cells with both microarray and real time PCR analysis using gene specific primers (see Supplementary Table 2).

Figure 3:
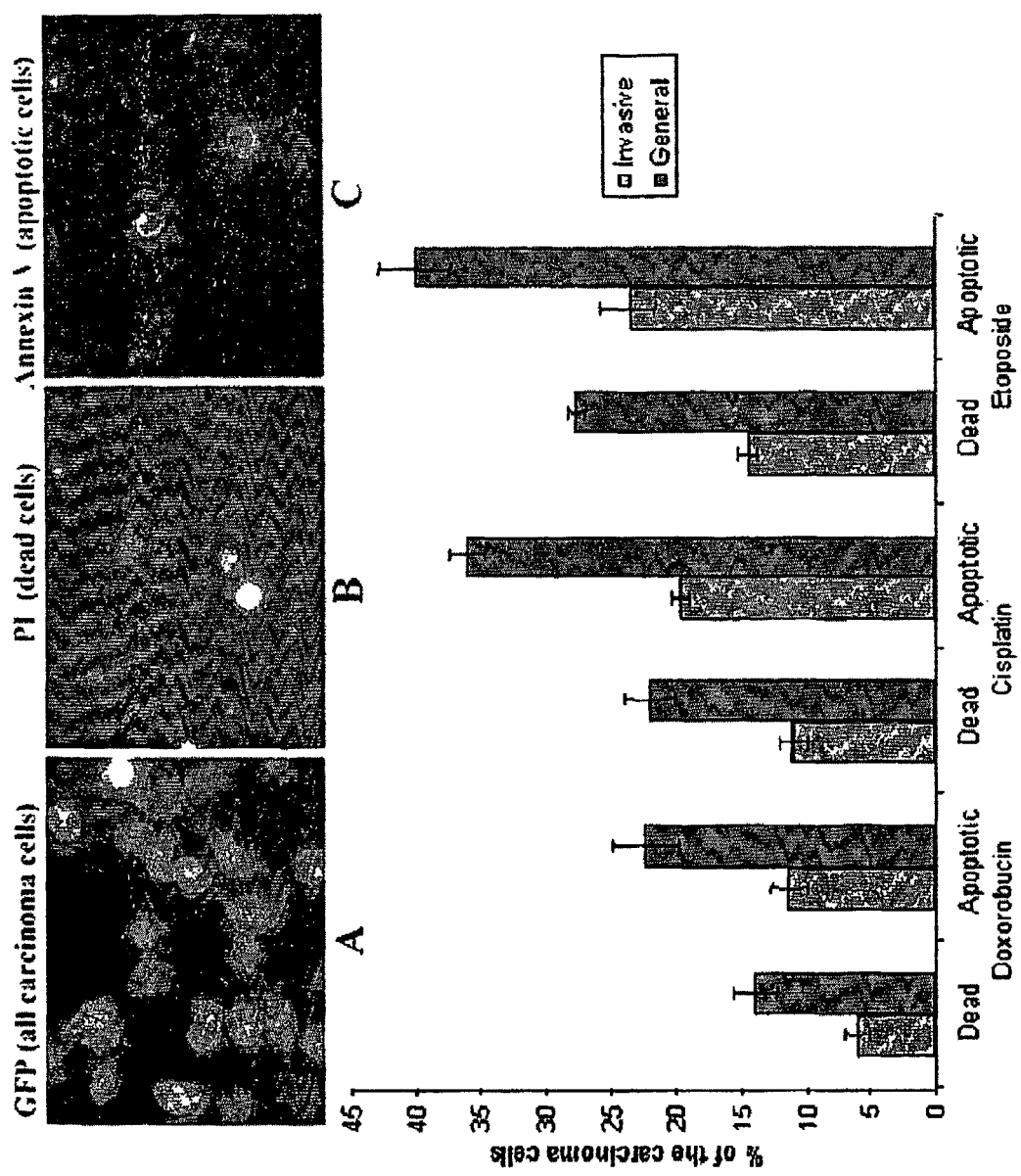
FIG. 3 is micrographs and a graph showing drug resistance in invasive cells compared to the general population of the primary tumor measured by an apoptosis assay. The cells collected by the needle collection procedure were subjected to drug challenge using doxorobucin (17 µM), cisplatin (50 µM) or etoposide (50 µM). The apoptotic status and viability of these cells was assessed by staining with propedium iodide (PI) and Annexin V-Cy5. Micrograph A shows the GFP channel with all the carcinoma cells. Micrograph B shows the dead cells with PI staining, and micrograph C is the Cy5 channel showing the apoptotic cells. The graph represents viability status and apoptotic index of the cells after being challenged by the anticancer drugs.

Drug resistance in invasive cells measured by apoptosis assay. The finding that the anti-apoptotic genes are up regulated in the invasive cells prompted us to study the functional importance of this finding and whether these cells indeed have a survival advantage over the resident population. We challenged the invasive cells with three most commonly used anticancer drugs, doxorobucin, cisplatin and etoposide. Previous studies have shown that these drugs to induce apoptosis in the MTLn3 cells (Huigsloot et al., 2002). We performed these studies on the invasive and general populations of cells from MTLn3-derived tumors. After treatment with the drugs the cells were allowed to recover for 24 hr. Subsequently, the apoptotic index and cell viability was measured as described in the Methods section. The results, shown in FIG. 3, demonstrate that as a percentage of all the carcinoma cells the invasive cells are able to tolerate all three drugs better than the general population of tumor cells. The process of FACS sorting by itself did not cause any change in the apoptotic index of the tumor cells (data not shown).

Most of the anticancer drugs like doxorobucin, cisplatin and etoposide are designed against the proliferative cells (Awada et al., 2003) making them cytotoxic. Recently, there is an increasing effort to make cytostatic drugs, which prevent the proliferation and invasion as opposed to killing the cells. There has been a demand in the field to have a method to isolate these invasive cells and look for the effect of cytostatic drugs specifically on invasive cells. We believe that in our studies we have demonstrated a method that makes possible this analysis on migratory cells of the primary tumor.

Figure 4:
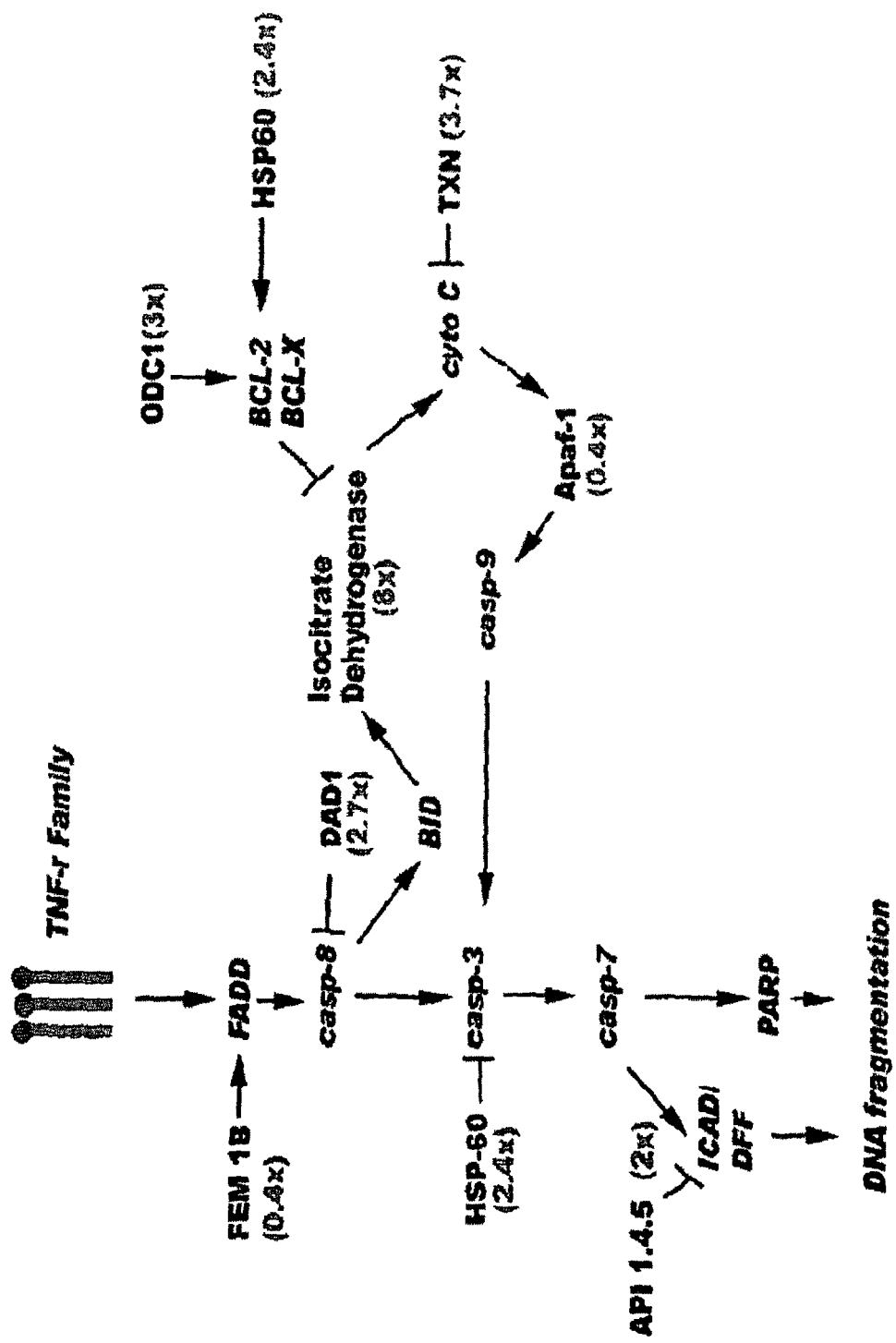
FIG. 4 is a schematic diagram of an apoptotic pathway indicating the pathways in which the anti- and pro-apoptotic genes are co-coordinately up- or downregulated respectively. The numbers in parenthesis indicate fold change in gene expression in the invasive cells compared to the general population.

Coordinate regulation of survival genes in the invasive cells. Previous studies have shown that the anti-apoptotic pathways are overexpressed in the metastatic cell lines (Real et al., 2002), and these cells have a survival advantage via Stat3 dependent over expression of BCL-2. In our study we find that a number of anti-apoptotic genes are upregulated. These genes belong to all three pathways, rendering a survival advantage to the cells. On one hand upregulation of the defender against death 1 (DAD1) gene indicates that the extrinsic pathway is blocked in these invasive cells. On the other hand there are signs of down regulation of the intrinsic pathway as well by the over expression of ornithine decarboxylase 1 (ODC1). Upregulation of the expression of apoptosis inhibitor 1, 4 and 5 (Api1, Api4 and Api5) genes indicate an involvement of the convergence pathway as well. Finally there is the robust over expression of the genes like immediate early response gene 3 (IER3) which is a multi-pathway regulator involving the NFκB family of transcription factors (Reed, 2003). Simultaneously a number of the pro-apoptotic were down regulated, significantly a key regulator of the intrinsic pathway APAF-1 was down-regulated in the invasive cells. FIG. 4 summarizes these findings and indicates the extent of change that occurs in the transcriptome of invasive cells.

In the current study we have attempted to investigate the pathways leading to metastasis, which provides this survival advantage to these cells. In previous studies, authors have used cell lines derived from an established secondary tumor (Real et al., 2002). We on the other hand have performed a dynamic assessment of the process of metastasis and have captured the cells prior to the entry into the blood.

In our studies we have identified pathways, which get regulated in the invasive cells, which are not proliferative (FIG. 1). The majority of the genes indicated in the functional category of "cell cycle" are genes that cause a reduction in cell proliferation and prevent the progression of the cell cycle. Recent studies have shown that the overexpression of Bcl2 in MTLn3 cells causes the cells to become resistant to dox-orobucin (Huigsloot et al., 2002) as observed by a reduction in drug-induced DNA fragmentation. Previous studies using cell lines derived from metastatic and resident cells from human breast adenocarcinoma have shown that the metastatic cell line was more resistant to anti-cancer drug treatment than the cell line from the primary tumor. However, it remains unknown at which stage of cancer progression (i.e. transformation, proliferation, invasion, intravasation, dissemination of metastases) the selection of the cells that have a survival advantage occurs. In this paper we show for the first time that this selection of cells with a survival advantage probably takes place at the very initial stage of invasion, as evident by the overexpression of anti-apoptotic genes and resistance to anticancer drugs by the invasive cells. The gene expression pattern observed here is associated with an invasive signature unique to these cells. Hence we have identified an expression pattern of survival genes that offer a survival advantage to non-proliferating invasive cells.

Example 2

Identification and Testing of a Gene Expression Signature of Invasive Carcinoma Cells Within Primary Mammary Tumors Example Summary We combined chemotaxis-based cell collection and cDNA microarray technology to identify the gene expression profile of invasive carcinoma cells from primary mammary tumors in experimental animals. Expression of genes involved in cell division and survival, metabolism, signal transduction at the membrane, and cell motility were most dramatically increased in invasive cells, indicating a population that is not dividing but intensely metabolically active and motile. In particular, the genes coding for the minimum motility machine that regulates β-actin polymerization, and therefore the motility of carcinoma cells, were dramatically up regulated, while ZBP-1, which regulates the localization of β-actin, was downregulated. This pattern of expression suggested ZBP-1 is a suppressor of invasion. Overexpression of ZBP-1 suppressed chemotaxis and invasion in primary tumors and inhibited metastasis from tumors generated using intensely metastatic cell lines. We identified genes important for the invasion of tumor cells in this study. We demonstrate that the identification of these genes provides new insight for the invasion process and the regulation of invasion and demonstrate the importance of these pathways in invasion and metastasis by altering the expression of a master gene, ZBP-1.

Introduction

A potential approach to determine the cellular mechanisms that contribute to invasion is to collect live cells from the primary tumor based on their ability to invade, and profile their gene expression patterns. One of the properties correlated with metastasis is chemotaxis to blood vessels (Wyckoff et al., 2000a). This cell behavior allows cells to orient and move toward blood vessels facilitating their intravasation. Based on these observations, we have developed a complementary approach to directly select for live, invasive cells from live primary tumors in intact rats using a microneedle containing a chemoattractant to mimic chemotactic signals from blood vessels and/or surrounding tissue (Wyckoff et al., 2000b). Overexpression of the EGF receptor and other family members has been correlated with poor prognosis (Nicholson et al., 2001), and therefore we have developed methods for collecting invasive tumor cells that use gradients of EGF to direct tumor cell invasion into microneedles. Gradients of EGF receptor ligands can be generated by diffusion from the blood as well as stromal cells in the tumor microenvironment (O'Sullivan et al., 1993; LeBedis et al., 2002). Thus we are using a physiologically relevant stimulus to mimic tumor cell invasion induced at the borders of tumors near blood vessels and other elements of connective tissue. We have used this method to test the hypothesis that chemotaxis to blood vessels is an important form of egress of carcinoma cells from the primary tumor. Cells have been collected from live rats with tumors that have been generated by the injection of carcinoma cells with different metastatic potential (Wyckoff et al., 2000b), and from live mice with mammary tumors derived from the expression of the PyMT oncogene (Lin et al., 2002; Lin et al., 2001; Wang et al., 2003).

In order to perform gene expression profiling using high density arrays on the few hundred cells commonly collected in microneedles, it is necessary to amplify mRNA by about 1000 fold to the amounts required for arrays. It is also necessary to have a pure cell population. Both of these conditions have been met using recently developed methods (Wang et al., 2003). RNA obtained from as few as 400 cells collected in a single microneedle from the primary tumor, when amplified as cDNA using the PCR based cDNA amplification technique (18), can be used for microarray expression analysis. We have validated this amplification method and demonstrated that it retains the original mRNA's copy abundance and complexity in the amplified product (Wang et al., 2003).

In the current study, the collection of invasive cells from the primary tumor using chemotaxis is combined with gene expression profiling using the above-described PCR based cDNA amplification techniques. This technology has allowed the characterization of gene expression patterns of invasive carcinoma cells from the primary tumor without potential artifacts that arise from the culturing of small populations of cells. We identified a group of genes that define motility pathways that are coordinately up regulated in invasive cells. These pathways may account for the enhanced migratory behavior of the collected cells. Furthermore, we tested the contribution of these pathways to invasion and metastasis by altering the expression of a master gene that regulates the expression of the common molecule on which these pathways converge.

Materials and Methods

Needle collection and FACS sorting of primary tumor cells. We used MTLn3-derived mammary tumors in rats (Farina et al., 1998b), and the microneedle collection method described previously (Wyckoff et al., 2000b; Wang et al., 2003), to study the gene expression pattern of invasive subpopulation of carcinoma cells within live primary tumors. Briefly, the invasive cells were collected from MTLn3 tumor using microneedles containing EGF. Cell collection was imaged using a multi-photon microscope as described previously (Wang et al., 2002) by inserting the bevel of a matrigel and EGF containing needle into the field of view. A 50 mm z-series consisting of 5 mm steps allows for the imaging of a large number of cells around the needle. $\frac{1}{10}$th of the volume from each needle was used to determine the number of cells collected. From the remaining $\frac{9}{10}$ volume from the microneedle, macrophages were removed by magnetic separation, and RNA extraction was done as previously described (Wang et al., 2003).

To isolate the general population of carcinoma cells from primary tumor, a small piece tumor was separated from the whole tumor, minced, and filtered twice through a nylon-filter to obtain a single cell suspension. FACS sorting was performed on the resulting single cell suspensions based on their GFP expression in tumor cells. GFP-positive tumor cells were collected into a tube and lysed directly for RNA extraction. All the procedures were done on ice or 4° C.

Because EGF and Matrigel are present in the needle, as a control experiment, we identified genes whose expression is altered by EGF or Matrigel application. Carcinoma cells from the primary tumor were FACS-sorted as described above. The resulting cells were split and plated on Mettek dishes covered with Matrigel (1:5) in the presence or absence of EGF (1 nM) for 4 hr at 37° C. The cells were then lysed directly on the dish for total RNA extraction.

An equal quantity of reference RNA (pooled RNA from rat liver, spleen, brain and kidney, 4:2:1:1, Ambion Tex.) was used to generate probes as a control in all our microarray experiments, which allowed us to use one of the channels as a hybridization control for all the spots on the microarray. The use of pooled reference RNA from the same species as the MTLn3 cells allowed the same interspecies cross hybridization as the background, allowing us to use mouse cDNA microarrays for our experiments. The pooled reference RNA covers a very broad range of gene expression and is routinely used as controls in cDNA microarray studies (Zhao et al., 2002).

RNA amplification, probe labeling and microarray hybridization. The RNA was then concentrated by ethanol precipitation and re-dissolved in 3.5 µl DEPC water. The total RNA was reverse-transcribed directly using the SMART PCR cDNA synthesis kit (Clontech, Palo Alto, Calif.) according to the manufacturer's protocol. After amplification, cDNAs were purified using the QIAquick PCR Purification Kit (Qiagen) and eluted with TE buffer. Labeling was performed using Label IT® (Mirus) following the manufacturer's instructions. Briefly, labeling reactions were prepared by mixing 10× Mirus Labeling Buffer A (10 µL), purified cDNA (3.5 µg), Cy5 (or Cy3) dye (5 µL) in a total volume of 100 µL. After incubating the reaction mix at 37° C. for 1 hr, the two resulting probes were purified by passing through SigmaSpin columns followed by Qiaquick columns. The purified Cy-3 and Cy-5 DNA probes were then combined and concentrated using micron YM 50 columns. Microarray analysis was performed by using cDNA microarrays made at AECOM. About 27,000 mouse genes (Incyte Genomics) were precisely spotted onto a single glass slide. Detailed descriptions of microarray hardware and procedures are available from http://129.98.70.229/. Microarray analysis was performed in three independent repeats. Details of slide hybridization, washing and image collection were described in previous studies (Wang et al., 2003; Wang et al., 2002).

Quality control and data analysis for microarrays. The scanned images were analyzed using the software Genepix (Axon Instruments, Inc. CA) and an absolute intensity value was obtained for each of the channels for the reference RNA and the RNA derived from the cells. The entire raw data set was filtered to accommodate a requirement of at least two good quality measurements for each triplicate experiment. Values from only the good quality measurements (where the signal strength was more than twice the standard deviation of the background plus the background) were considered for further analysis. Two types of normalization were performed routinely in tandem on all the experiments using the GeneSpring software package (Silicon Genetics, Redwood City, Calif.). First, intensity-based-normalization was performed which takes into consideration the overall signal strength of both channels and normalizes the signal strength between all the different chips, reducing the chance of chip-to-chip variability due to the experiment being performed on different days. Second, a reference-channel-based normalization was performed which takes into consideration the reference channel (which in this case is pooled reference RNA) and normalizes the values in all the spots. This reduces the chance of spot to spot variability. The final data was a result of both these types of normalization.

In order to determine the significance of upregulated and downregulated genes, we calculated the standard deviation of the reference channel in all of the chips and found it to be 0.18 and used 5× standard deviation as the cutoff, indicating a high level of fidelity in our data above 2-fold. Genes that were up- or down-regulated in the arrays performed on control samples (FACS sorted cells which were treated with Matrigel and EGF) were removed from the final list of genes specific to the invasive subpopulation of tumor cells.

Real time PCR confirmation. To verify the data obtained from microarrays, QRT-PCR analysis of selected overexpressed and underexpressed genes was performed by using the iCycler Apparatus (Bio-Rad) with sequence-specific primer pairs for all genes tested (see Supplementary Table 3 for primer sequences, amplicon size and Tm) as described previously (Wang et al., 2002). The SYBR Green PCR Core Reagents system (Perkin-Elmer Applied Biosystems) was used for real-time monitoring of amplification.

Plasmid construction, cell culture transfection, infection and generation of ZBP-1 stable expression cell lines. FLAG-ZBP-1 (Farina et al., 2003) was digested with BamHI/XbaI and inserted into the BamHI/XbaI sites of EGFP-C1 (Clontech). The EGFP-FLAG-ZBP-1, which encodes a fusion protein, was then isolated as Eco47III/XbaI restriction fragment, blunt ended and inserted into a filled XhoI site of pMCSVneo (Clontech). This vector contains a viral packaging signal, neomycin resistance gene, and the 5' and 3' long terminal repeats from the murine PCMV virus. As a result, the LTR drives high-level constitutive expression of the EGFP-FLAG-ZBP-1 gene. PHOENIX cells were cultured under standard conditions (Dal Canto et al., 1999) and were transfected with EGFP-FLAG-ZBP-1 using FUGENE (Roche). Retroviral supernatant was harvested and used to infect MTLn3 cells as previously described (Dal Canto et al., 1999). Stable MTLn3 cells were selected in the presence of neomycin.

Microchemotaxis chamber assay. A 48-well microchemotaxis chamber (Neuroprobe) was used to study the chemotactic response to EGF, following the manufacturer's instructions and as described previously (SEGALL ET AL., 1996).

Blood burden, single cells in the lung, and metastases. MTLn3-ZBP-1 or MTLn3-GFP cells were injected into the mammary fat pads of female Fischer 344 rats. Tumor cell blood burden was determined as described previously (Wyckoff et al., 2000a). After blood removal and euthanization of the rat, the lungs were removed and the visible metastatic tumors near the surface of the lungs were counted. For measurement of metastases, excised lungs were placed in 3.7% formaldehyde, mounted in paraffin, sectioned, and stained with H&E. Slices were viewed using a 20× objective, and all metastases in a section containing more than five cells were counted (Wyckoff et al., 2000a).

Results

Gene expression patterns unique to invasive tumor cells. GFP-labeled tumor cells were injected into rat mammary fat pads, and primary tumors were allowed to grow for 2-2.5 weeks. To provide insight into the pattern of gene expression associated with chemotactic and invasive carcinoma cells in vivo, we compared the gene expression profile of the subpopulation of invasive tumor cells collected from the primary tumor by chemotaxis into a microneedle with that of the general population of GFP-expressing tumor cells sorted from the whole primary tumor by FACS (FIG. 5B). Hereafter, the former population of cells will be called the invasive cells, and the latter the general population, respectively. The invasive subpopulation of tumor cells was collected into microneedles filled with EGF and Matrigel that were held in the primary tumor for up to 4 hours as described previously (Wyckoff et al., 2000b; Wang et al., 2003). The collection of the invasive cells was monitored by imaging the GFP-expressing cells with a multiphoton microscope as they migrated to the EGF containing microneedles (FIG. 5A). This allowed direct confirmation that collection was due to cell migration and not a passive process.

The collected cells were a mixture of carcinoma cells (75%) and macrophages (25%) as shown previously (Wang et al., 2003). Macrophages were removed by binding to magnetic beads conjugated with anti-MAC-1, giving a greater than 96% pure population of carcinoma cells for analysis (Wang et al., 2003). The general population of primary tumor cells was collected by FACS sorting and plated either on matrigel or matrigel and EGF for 4 hours, the interval of time required for microneedle collection, to mimic the collection conditions prior to purification of the RNA. These controls were done to subtract patterns of gene expression resulting from stimulating cells with matrigel and EGF, and allowed identification of the gene expression signature of the invasive cells (FIG. 5B).

Figure 6:
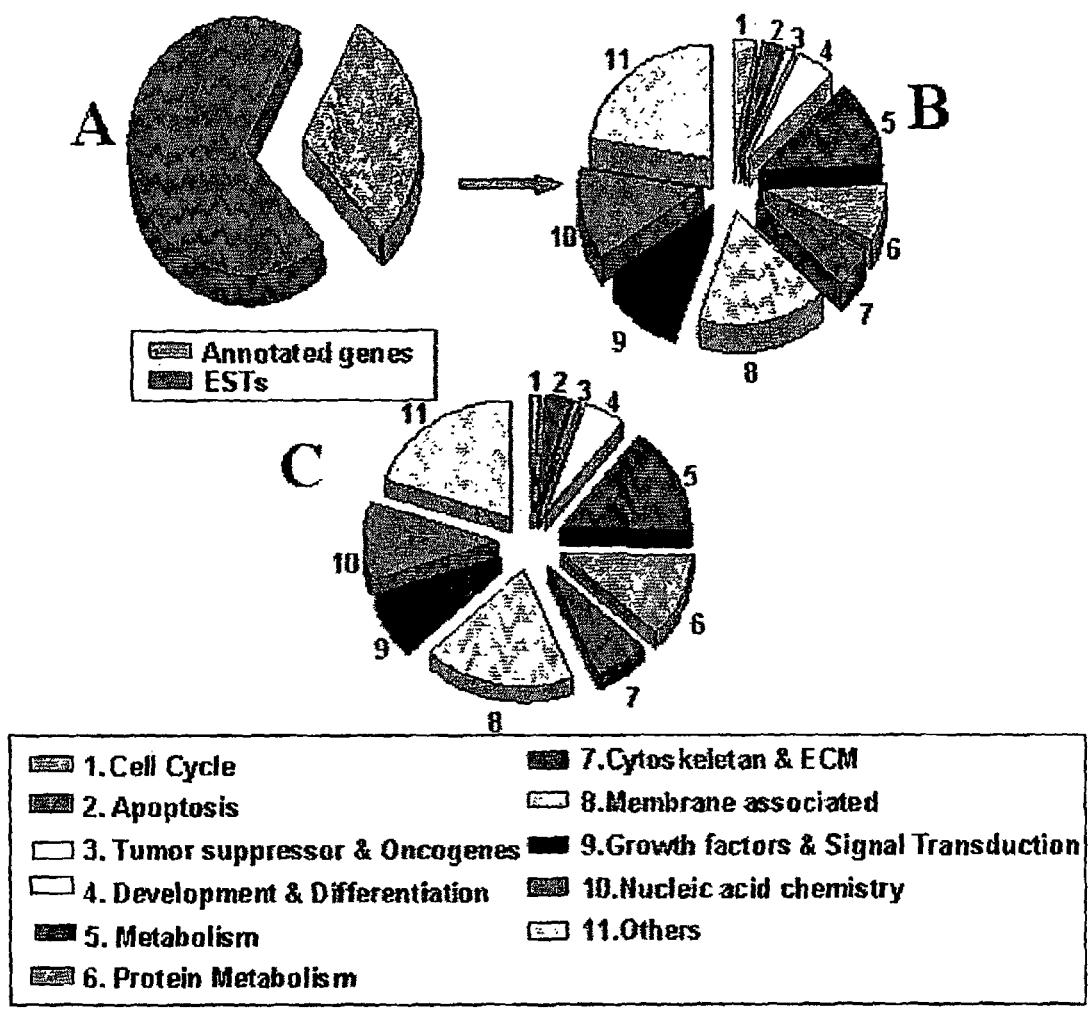
FIG. 6 is summary diagrams showing functional categories of the genes regulated in the invasive cells. The pie charts represent the relative proportion of genes in 11 categories based on their function using Gene-ontology Consortium classification. Chart A represents the relative proportion of annotated spots compared to ESTs on the array. Chart B shows the proportional representation of the functional groups into which the genes annotated in A fall. Panel C shows the proportional representation of the functional groups into which the genes regulated in the invasive cells fall.

Differential gene expression analysis comparing the invasive and general populations of tumor cells revealed 1366 genes that were differentially expressed (Supplementary Table 4). As shown in FIG. 6, genes with known functions were divided into eleven different functional categories based on definitions provided by the gene-ontology consortium (Mariadason et al., 2002), (http://www.geneontology.org).

In order to determine the significance of changes in gene expression in each of the functional categories of the genes represented in our arrays, Chi-square or SAM analysis were performed. The functional categories of Cell Cycle, Apoptosis, Metabolism, Protein Metabolism, Cytoskeleton & ECM, Growth Factor & Signal Transduction and Nucleic Acid Chemistry were found to be statistically significant in the invasive cells by Chi-square (Zigeuner et al., 2004) or SAM analysis (Tusher et al., 2001). Random sets of equal numbers of genes did not generate the same pattern of up and down regulation indicating that the pattern was not observed by chance ($P<0.05$). Similarly, clustering the results from all genes of the general population in the same space of all genes on the microarray did not yield an outcome similar to the invasion signature ($P>0.05$). A detailed table indicating each of the functional categories and the significant analysis is given as a supplementary table (Supplementary Table 5) indicating the number of genes printed on the microarray and the number regulated in invasive cells.

It is interesting to note that the number of genes whose expression is regulated up or down in the functional category called cell cycle (FIG. 6, #1) is reduced in the invasive cells compared to the general population. In addition, there is a reduction in the number of regulated genes of the Nucleic Acid Chemistry category (FIG. 6, #10), which includes genes necessary for DNA synthesis. These may indicate that the cell proliferation activity of invasive cells is repressed (Bravo et al., 2003) and the cell cycle is arrested (Nishitani and Lygerou, 2002). The increase in the number of genes regulated in both the General Metabolism and the protein metabolism categories (FIG. 6, #5 and 6, respectively) may indicate that invasive cells are very active metabolically, probably utilizing more energy and having a fast turnover of proteins (Larsen et al., 2003). The number of genes regulated in the Apoptosis category (FIG. 6, #2) is significantly higher in the invasive cells. A closer inspection of the genes involved shows that the pro-apoptotic genes are downregulated and the anti-apoptotic genes are upregulated. This may indicates that these cells have a survival advantage over the general population. Conversely, the genes involved in the Growth Factors and Signal Transduction group (FIG. 6, #9) is markedly reduced. These, taken together with the Cell Cycle genes (FIG. 6, #1), jointly indicate a significant reduction in the proliferative nature of these cells (Supplementary Table 5).

Finally, there is an increase in the number of regulated genes in the Cytoskeleton and Extracellular Matrix category (FIG. 6, #7). This is of particular relevance to the migratory behavior of the tumor cells that is important in their invasion (discussed next).

Genes involved in invasion. In order to be collected by the microneedle, the carcinoma cells must be capable of moving toward and crawling into the extracellular matrix of the microneedle within the 4 hr. collection interval. If a cell moves 2 cell diameters during this interval to gain entry to the microneedle it would have a minimum speed of 0.2 μm/min, similar to the velocity of carcinoma cells in vitro. However, carcinoma cells move in the primary tumor at speeds up to 10× this minimum value (Condeelis and Segall, 2003) indicating that cells from hundreds of microns away from the microneedle can be recruited for collection and that the cells may penetrate the extracellular matrix in the collecting microneedle. Consistent with this prediction is the observation that carcinoma cells are found within the matrix of the collecting microneedle, indicating that cells have traveled hundreds of microns during the collection interval. This indicates speeds much greater than 0.2 μm/min in vivo.

Figure 7A:
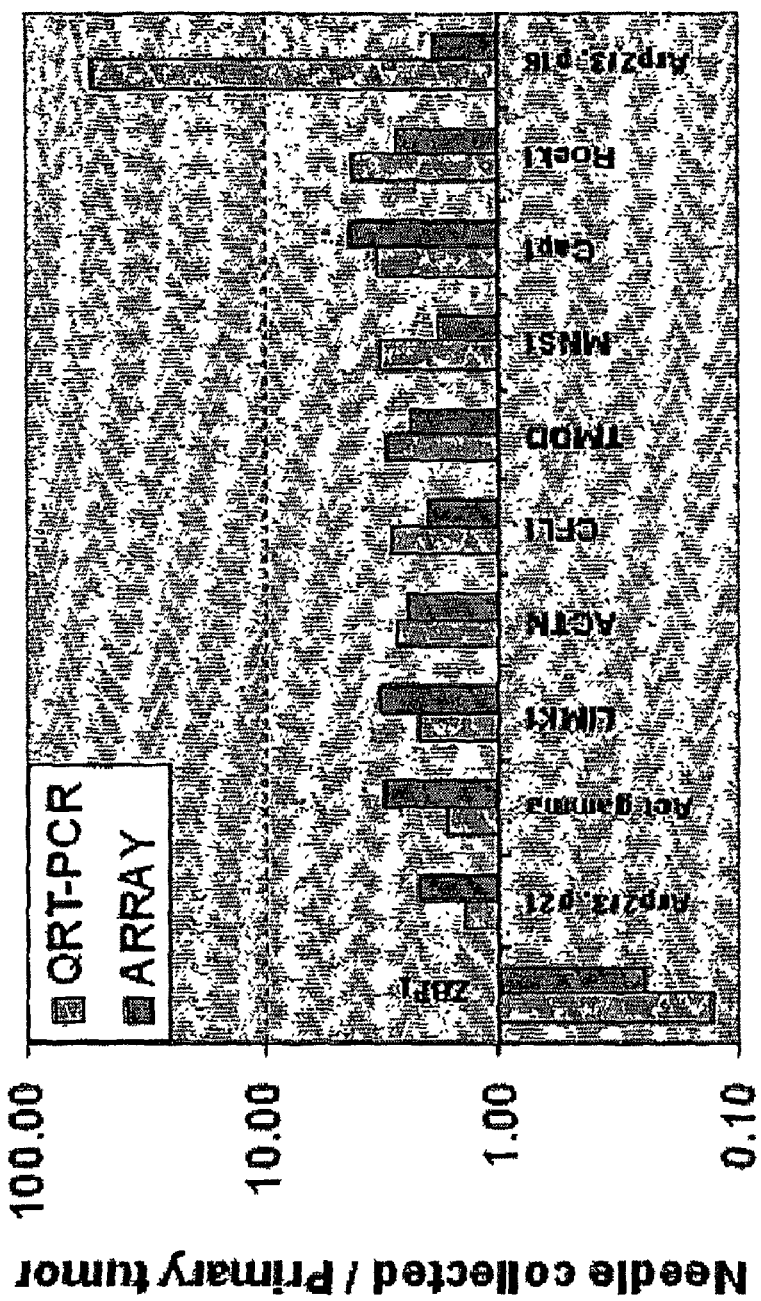
FIG. 7, Panel A is a graph showing validation of microarray results for selected genes by quantitative real time PCR (QRT-PCR). Comparison of expression analyses in needle collected tumor cells gives similar results for cDNA microarrays and QRT-PCR. Panel B is a diagram summarizing results showing that the minimum motility machine pathways in the invasive cells are upregulated. Genes involved in these pathways are upregulated in the invasive cells as shown by microarray and QRT-PCR. The extent of upregulated expression is indicated next to each component of the pathway as Nx.

The motility cycle of chemotactic crawling cells is composed of 5 steps; signal sensing, protrusion toward the signal source, adhesion, contraction and tail retraction (Bailly and Condeelis, 2002). As shown in Table 1 and FIG. 7, based on the microarray analysis, many genes associated with motility are upregulated in the invasive cells compared to the general population of cells. We verified the array results using real time PCR for selected genes representing the 5 steps of the motility cycle. As shown in FIG. 7A, the same pattern of expression was observed in the invasive cells with both microarray and real time PCR analysis.

List of motility related genes differentially expressed in the invasive sub-population of tumor cells. Genes associated with motility are displayed in this table and the ratios on the right indicated the level of expression in the invasive compared to the general population of cells of the primary tumor.

TABLE 1

| Gene Description | Needle/FACS |
|---|---|
| Capping protein alpha 1 | 4.34 |
| Cell division cycle 42 | 3.96 |
| Capping Protein alpha 2 | 3.89 |
| Moesin | 3.67 |
| Rho interactin protein 3 | 3.33 |
| LIM-kinase 1 | 3.24 |
| Palladin | 3.12 |
| Zyxin | 2.93 |
| Tropomyosin alpha chain | 2.86 |
| Rho-associated coiled-coil forming kinase 1 | 2.71 |
| Testis expressed gene 9 | 2.67 |
| Phosphatidylinositol-4-phosphate 5-kinase type II alpha | 2.60 |
| Epidermal growth factor receptor | 2.59 |
| Capping protein (actin filament), gelsolin-like | 2.53 |
| Annexin A5 | 2.47 |
| CRIPT protein | 2.32 |
| Protein kinase C, zeta | 2.30 |
| Arp 2/3 complex subunit p21 | 2.22 |
| RAB25, member RAS oncogene family | 2.19 |
| Vinculin | 2.16 |
| Kinesin family member 5B | 2.13 |
| Catenin beta | 2.08 |
| Chaperonin subunit 4 (delta) | 2.06 |
| Chaperonin subunit 3 (gamma) | 2.06 |
| Tubulin Alpha-4 chain | 2.05 |
| Integrin beta 1 (fibronectin receptor beta) | 2.00 |
| Cofilin 1, non-muscle | 1.98 |
| Arp 2/3 complex subunit p16 | 1.93 |
| Kinectin 1 | 1.91 |
| Downstream of Tyrosine Kinase 1 | 1.91 |
| Burkitt lymphoma receptor 1 | 1.90 |
| Wave 3 | 1.89 |
| Rho-associated coiled-coil forming kinase 2 | 1.63 |
| Cadherin 1 | 1.51 |
| Fibroblast growth factor receptor 1 | 0.54 |
| Zip code binding protein 1 | 0.25 |
| Alpha-Actinin, smooth muscle isoform | 0.21 |

Figure 7B:
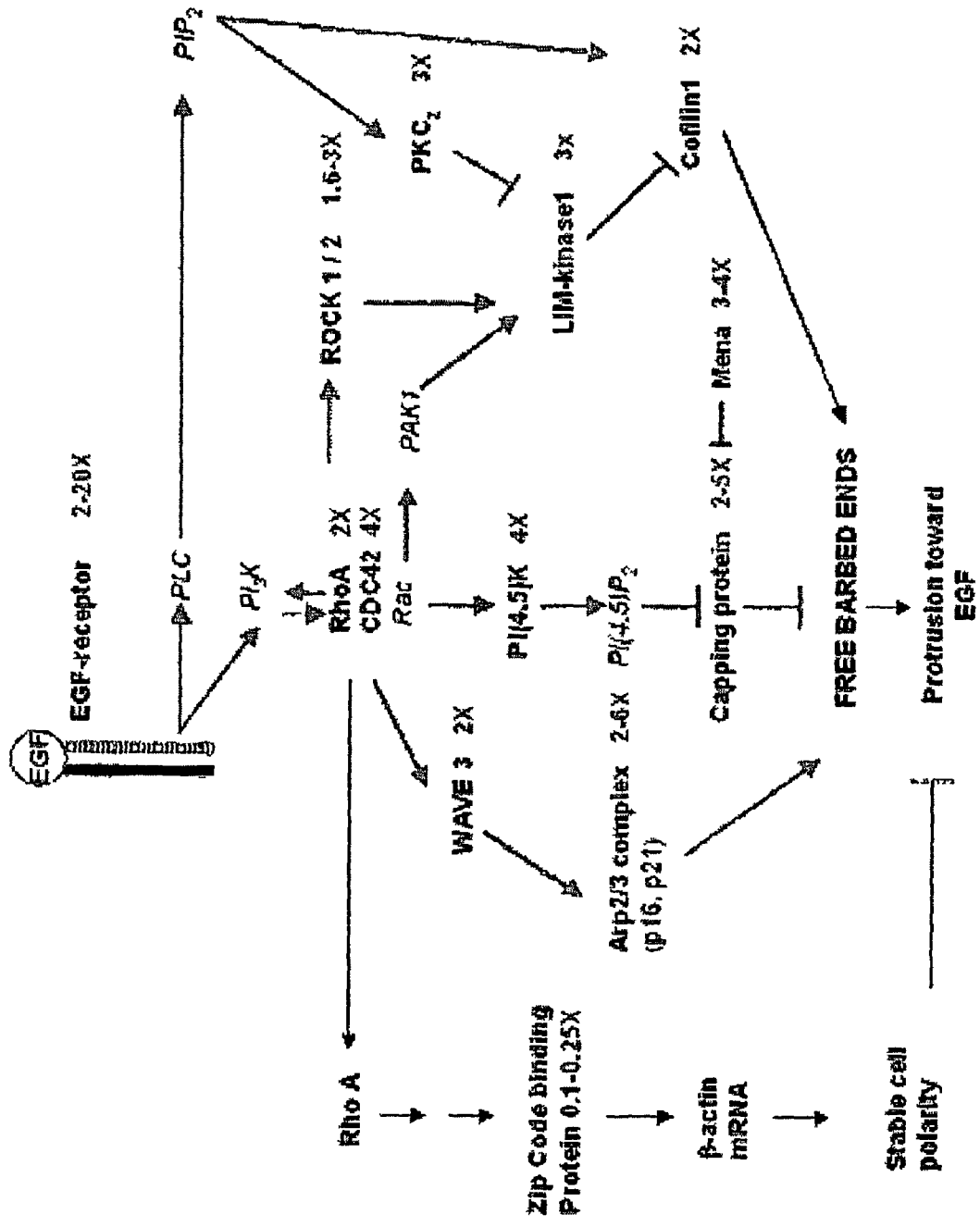

The protrusion of a pseudopod toward the chemotactic signal initiating the motility cycle is the key step in defining the leading edge of the cell and therefore its direction during migration (Bailly and Condeelis). Protrusion is driven by actin polymerization-based pushing against the cell membrane and this requires the minimum motility machine composed of cofilin, Arp2/3 complex and capping protein acting on their common downstream effector, β-actin (Mogilner and Edelstein-Keshet, 2002). The elevated expression of any one of these three effectors is expected to significantly enhance the speed of migration of cells since doubling the amount of either Arp2/3 complex, capping protein or cofilin in the reconstituted minimum motility machine can increase protrusion rate by 10× (Loisel et al., 1999). Therefore, it is significant, as shown in FIG. 7B, that the genes coding for all three end-stage effectors, the Arp2/3 complex (the p16 and p21 subunits), capping protein and cofilin, are up regulated by at least two-fold each. Furthermore, the genes coding for the pathways regulating the activities of Arp2/3 complex (WAVE3), capping protein and cofilin are coordinately upregulated in the invasive cell population. In the cofilin pathway, genes for ROCK1 and ROCK2, LIMK 1 and PKCζ are upregulated along with cofilin. LIM-kinase is activated either by PAK which is regulated by Cdc42-GTP and Rac-GTP or by ROCK which is regulated by Rho-GTP. Either PAK (Edwards et al., 1999) or ROCK (Ohashi et al., 2000) can phosphorylate LIM-kinase thereby activating it to increase cofilin phosphorylation. Inhibition of LIM-kinase activity is PKC dependent and this involves one of the unconventional PKC isoforms (Edwards et al., 1999). As shown in FIG. 7B, PKCζ gene expression, the inhibitory branch of the LIM-kinase inhibitory pathway, is elevated along with that of the activating branch of the pathway involving ROCK and PAK.

Similar increases in both the stimulatory and inhibitory parts of the capping protein pathway are upregulated in invasive carcinoma cells (FIG. 7B). The expression of both the alpha and beta subunits of capping protein is increased. In addition, genes that antagonize capping protein function such as the type II alpha isoform of PI4, 5 kinase and Mena are upregulated (Cooper and Schafer, 2000; Bear et al., 2002).

Genes coding for proteins involved in myosin mediated contraction and tail retraction (tropomyosin, ROCK1, and calpain), gelsolin-like protein (CAPG) and adhesion molecules (zyxin, vinculin, and integrin β1) are up regulated, as well (Table 1). ROCK plays a crucial role in cell adhesion and motility and is linked to pathogenesis and progression of several human tumors (Sahai and Marshall, 2003). Integrin β1 has previously been implicated in the ability of an experimentally transformed fibroblast cell line to metastasize (Brakebusch et al., 1999), and its expression is increased in upper aerodigestive tract and cervical squamous cell carcinomas (Van Waes et al., 1995).

ZBP-1 as a master gene regulating cell polarity. A gene that is strongly downregulated in invasive cells is Zip-code binding protein (ZBP-1) (Table 1 and FIG. 7). ZBP-1 is a 68 kD RNA-binding protein that binds to the mRNA zipcode of β-actin mRNA and functions to localize the mRNA to the leading edge of crawling cells. β-actin is the preferred isoform of actin for the polymerization of filaments at the leading edge of cells and, therefore, is acted on by the cofilin, capping protein and Arp2/3 pathways (Shestakova et al., 2001). β-actin mRNA localization is required for the generation of intrinsic cell polarity that is characteristic of normal fibroblasts and epithelial cells. Disruption of ZBP-1-mediated p-actin mRNA targeting leads to cells without stable cell polarity (Shestakova et al., 2001), and loss of β-actin mRNA targeting is correlated with the polarity of carcinoma cell lines in vitro and in vivo (Shestakova et al., 1999; 2001). Therefore, ZBP-1 is a candidate invasion suppressor gene required for normal cell polarity by determining the sites in cells where the Arp2/3 complex, capping protein and cofilin pathways converge by controlling the sites of targeting of β-actin mRNA and the location of β-actin protein that is the common downstream effector of these pathways (FIG. 7B).

Figure 8:
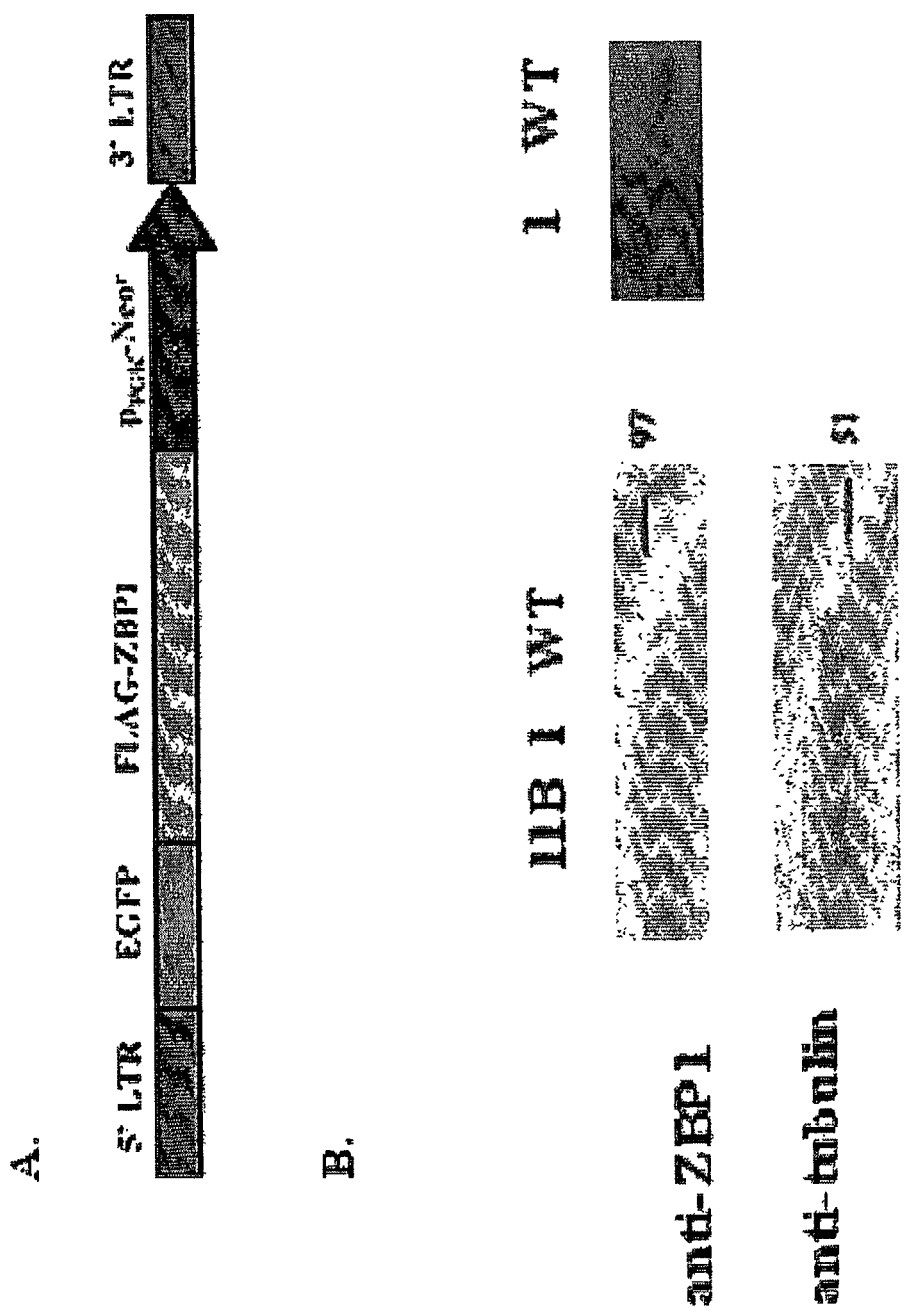
FIG. 8 is a diagram and photographs of ZBP-1 construct and overexpression in MTLn3. Panel A is a diagram of the full length ZBP-1 gene was subcloned in a pMCSVneo vector and transfected into parental MTLn3 cells. The control plasmid used in the experiments was the pGreenLantern-1. Panel B is western blots showing stable MTLn3-ZBP-1 clones 1 and 11B selected in the presence of neomycin. The western blots on the left show the increased ZBP-1 protein expression in these 2 separate clones. The western blot on the right shows a longer exposure time so that the endogenous ZBP-1 expression in wild type MTLn3 cells can be seen relative to the overexpression.

To test the hypothesis that ZBP-1 expression can suppress invasion, the full length ZBP-1 gene was subcloned in a pMCSVneo vector (FIG. 8A) and transfected into the parental MTLn3 cells. Data from Western blot analysis (FIG. 8B) confirmed that stable clones transfected with pEGFP-FLAG-ZBP-1 expressed higher levels of ZBP-1 compared to untransfected cells. To account for any effects that might arise from the introduction of EGFP into cells, MTLn3 cells transfected with pGreenLantern-1 vector (Life Technologies, Inc.) were used as control.

To investigate the chemotactic properties of the ZBP-1 overexpressing cells, two independent clones of ZBP-1 overexpressing cell lines were characterized. Chemotaxis was measured in a Boyden chamber. ZBP-1 overexpressing cells migrated through the filter in response to EGF poorly compared to the parental MTLn3 cells (FIG. 9A), indicating that chemotaxis was inhibited. This was true for both ZBP-1 clones and is consistent with previous data showing the enhanced intrinsic cell polarity of ZBP-1 expressing cells (Shestakova et al., 1999; 2001). Furthermore, the ability of carcinoma cells to invade microneedles placed into primary tumors derived from MTLn3 cells over expressing ZBP-1 was greatly reduced (FIG. 9B) further indicating a reduction in chemotaxis.

Injection of the ZBP-1 over expressing cells into the mammary fat pads of rats resulted in tumors that were less metastatic. The metastatic potential of these tumors was characterized as the number of tumor cells present in circulating blood (FIG. 10A), and the number of lung metastatic tumors (FIG. 10B). However, as shown in FIG. 10C, tumor growth was not affected by increasing the expression of ZBP-1. In addition, primary tumors derived from control and ZBP-1 overexpressing cell lines were indistinguishable as judged by their histology upon multiphoton imaging of GFP-expressing tumor cells (data not shown).

Discussion

Signature of invasive carcinoma cells. By comparing gene expression patterns of invasive cells to those of the general population of carcinoma cells in the same primary tumor, we were able to find patterns in the regulation of gene expression population of the same tumor defined here, we have found that a subset of genes (Table 2), maintain the same patterns of regulation in both studies. This suggests that the invasive subpopulation of cells collected from primary tumors with microneedles has enhanced an expression pattern of a subset of genes that is characteristic of the differences between metastatic and non-metastatic cell lines and tumors. This is emphasized by the fact that the invasive subpopulation of cells collected by chemotaxis into microneedles is from tumors derived from a single cell line, the MTLn3 cell line. This indicates that as the tumor progresses, highly invasive cells are selected in which a pattern of gene expression present in metastatic cells and tumors is enhanced over the pattern of expression of the cells that remain behind in the primary tumor.

Differentially expressed genes common to invasive cells identified in this study and to metastatic tumors and cell lines identified in a previous study. Common genes regulated in a similar way in all the three samples are displayed here. Dark shading indicates overexpression and light shading represents repression. Taken together these genes outline a signature of invasion and indicate that a number of interacting pathways are involved in invasion.

TABLE 2

| Gene name | Met/non met, Cell line* | Met/non met, Tumor** | Needle/ FACS*** | Gene function |
|---|---|---|---|---|
| Collagen, type III, alpha 1 | 0.01 | 0.15 | 0.19 | ECM Composition |
| G-protein coupled receptor 26 | 0.14 | 0.2 | 0.46 | Signal transduction |
| Zip code binding protein 1 | 0.08 | 0.03 | 0.25 | Cell polarity |
| Fibroblast growth factor receptor 1 | 0.32 | 0.35 | 0.53 | Signal transduction |
| ARP 2/3 COMPLEX 16 KD SUBUNIT. | 6.31 | 5.45 | 1.93 | Minimum motility machine |
| Tight junction protein 2 | 2.96 | 2.16 | 3.4 | Adhesion Molecules |
| Member Ras oncogene family | 7.99 | 6.38 | 2.18 | Signal transduction |
| Epidermal growth factor receptor | 20.12 | 2.0 | 2.6 | Signal transduction |

*Metastatic cell line = MTLn3, non-metastatic cell line = MTC;
**Tumor derived from injection of MTLn3 or MTC;
***Needle = cells collected into needle by chemotaxis = invasive; FACS = cells obtained from whole tumor by FACS = general population.

unique to the invasive subpopulation of cells. Our results indicate that the regulation of genes involved in cell division, metabolism, signal transduction at the membrane, cell survival and cell motility was most dramatically changed in invasive cells predicting a population that is neither proliferating nor apoptotic but intensely metabolically active and motile. While increased cell proliferation during tumor development has been associated with poor prognosis in patients (Evan and Vousden, 2001), the results reported both here and in previous studies (Wyckoff et al., 2000a) indicate that tumor size is neither correlated with invasion nor the ability of cells to metastasize to distant organs. In addition, invasive cells show down regulation of genes associated with apoptosis and up regulation of genes for cell survival. This is consistent with previous work where it was shown that cell survival genes were up regulated in metastatic tumors as compared to non-metastatic tumors (Wang et al., 2002) and suggests that the invasive subpopulation may contribute disproportionally to this expression profile in whole metastatic tumors.

In a previous study, the genes differentially expressed between metastatic and non-metastatic cells in culture and the tumors derived from them by orthotopic injection of the cells into the mammary gland were compared. We found that those coding for molecules involved in cell adhesion, motility, cell polarity, and signal transduction were most different. Comparing the gene expression patterns in non-metastatic tumors to metastatic tumors from the previous study (20), with the differences between the invasive cell population and general Cell motility genes and their roles in cancer invasion. Chemotaxis to EGF is required for collection of cells into the microneedle because significant numbers of cells are not collected in the absence of EGF (Wyckoff et al., 2000b), and EGF-R activity is required for the collection of carcinoma cells. Therefore, the motility related genes that are differentially expressed in the invasive population may also contribute to EGF-dependent chemotaxis and enhanced migration in the primary tumor. A major result of this study is the finding that genes from the pathways associated with the minimum motility machine are greatly up regulated, predicting that protrusion velocity will be increased. Since protrusion sets cell direction and, therefore, defines chemotaxis, this step in the motility cycle may be key in determining invasive potential. Furthermore, as seen in FIG. 7B, genes coding for key components of the pathways regulating the end stage effectors of the minimum motility machine are up regulated together, from the receptor through the key kinases and finally the end stage effectors themselves. By upregulating these entire pathways, receptor-ligand stimulated motility would be greatly enhanced leading to increased invasiveness. These results are consistent with the 10-fold higher velocity of cell migration toward blood vessels and EGF filled microneedles, both sources of chemoattractant, observed in primary tumors of un-dissected live rats and mice compared to their cultured cell counterparts (Wyckoff et al., 2000a; 2000b; Farina et al., 1998b; Wang et al., 2002; Condeelis and Segall, 2003). Consistent with these results are the finding that inhibition of the nucleation activity of Arp2/3 complex in carcinoma cells in culture inhibits chemotaxis to EGF (Bailly et al., 2001) and that cofilin activity is required for cell motility in carcinoma cells (Chan et al., 2000).

Our results show that cofilin, LIM-kinase 1, ROCK 1, 2 and PKCζ are all over expressed in highly invasive carcinoma cells. In previous studies, LIM-kinase 1 was shown to be over expressed in metastatic breast and prostate tumors (Davila et al., 2003; Yoshioka et al., 2003). Over expression of LIM Kinase 1 in tumor cell lines increased their motility and invasiveness in vitro (Davila et al., 2003) and in vivo (Yoshioka et al., 2003). Reduction in the expression of LIM-kinase 1 in metastatic prostate cell lines deceased invasiveness in matrigel invasion assays (Davila et al., 2003). These results are consistent with ours shown here that LIM-kinase 1 is more highly expressed in the invasive cell population.

In contrast, it has been reported that increased expression of LIM-kinase 1 in carcinoma cells significantly reduces their cell motility as the phosphorylation of cofilin by LIM-kinase 1 abolishes EGF induced actin nucleation and polymerization (Zebda et al., 2000). Our study may resolve this paradox by demonstrating that in invasive cells collected from primary tumors both the stimulatory and inhibitory pathways to LIM-kinase 1 and cofilin are over expressed together thereby increasing the steady state rate of cofilin activation in invasive carcinoma cells resulting in enhanced cell motility as predicted previously (Davila et al., 2003; Yoshioka et al., 2003; Zebda et al., 2000; Sahai et al., 2001).

ZBP-1 in metastasis. In general, cells that lack a fixed intrinsic polarity are more chemotactic to exogenous gradients presumably because there is no intrinsic polarity to be overcome by the exogenous chemotactic signal and the cell can turn in any direction to respond to a gradient (Parent and Devreotes, 1999; Iijima et al., 2002). The presence of intrinsic polarity in carcinoma cells in tumors is correlated with the stable polarization of actin polymerization at one end of the cell only, resulting in polarized locomotion. In contrast, carcinoma cells in metastatic MTLn3 tumors are unpolarized except when they are near blood vessels where they become polarized toward the blood space (Shestakova et al 1999; Wyckoff et al., 2000a). These results suggest that cells that have proceeded through the epithelial mesenchymal transition (EMT) to the point where all remnants of the intrinsic cell polarity of the original epithelium are lost, such as MTLn3 cells, are more efficient at responding to external chemotactic signals and more attracted to blood vessels in the primary tumor.

A key difference between metastatic and non-metastatic cells that may explain the inverse correlation between intrinsic cell polarity and metastasis is loss of the ability by metastatic cells to localize mRNA and proteins that define cell polarity (Shestakova et al., 1999). The mechanism relating β-actin mRNA targeting to the leading edge and intrinsic cell polarity involves the localization of β-actin nucleation to the leading edge during motility. Disruption of mRNA targeting to the leading edge using oligonucleotides that disrupt the interaction between ZBP-1 and the targeting sequence in the mRNA, the zip-code, results in delocalization of mRNA and β-actin nucleation sites, and the disruption of cell polarity (Shestakova et al., 2001). Highly metastatic cells have lost the ability to target mRNA for β-actin, which may be required to maintain a localized supply of β-actin protein to support a stable leading edge in response to the activity of the minimum motility machine. Without a stable leading edge, the intrinsic polarity of the metastatic cell is lost and cell direction is determined by signals from blood vessels, resulting in chemotaxis toward blood vessels and intravasation (Wyckoff et al., 2000a; Condeelis and Segall, 2003). Molecular profiling of MTLn3 and MTC cells and tumors using both cDNA arrays and QRT-PCR demonstrates that non-metastatic MTC cells and tumors express much higher levels of ZBP-1 than the metastatic MTLn3 cells and tumors (Wang et al., 2002). Furthermore, in the present study, invasive tumor cells isolated from primary mammary tumors using chemotaxis express much lower levels of ZBP-1 than cells that remain behind in the primary tumor even though both cell populations were derived from the same progenitor MTLn3 cells (Table 2). Furthermore, as shown in the current study, invasive carcinoma cells expressing experimentally increased levels of ZBP-1 after transfection with ZBP-1 expression vectors exhibit decreased chemotaxis, and invasion into microneedles, and the tumors made from cell grafts of these ZBP-1 expressing cells are much less metastatic by several criteria.

The results reported here indicate that ZBP-1 is a 'metastasis repressor' and, together with mRNA targeting status and analysis of tumor cell polarity around blood vessels discussed above, might be used in prognosis and therapy.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

SUPPLEMENTAL TABLE 1

| ID | Acc No | Gene | Description | N/F ratio |
| --- | --- | --- | --- | --- |
| 1, 13, 7 | AW554270 | Hnrpu | heterogeneous nuclear ribonucleoprotein U | 6.962446985 |
| 1, 15, 6 | AW557056 | | ESTs | 9.827643601 |
| 1, 20, 17 | AW536795 | Clk | CDC-like kinase | 2.522978124 |
| 1, 8, 19 | AA404094 | C11orf17 | C11orf17 | 2.898634353 |
| 10, 10, 16 | AW537281 | | ESTs | 2.050253842 |
| 10, 11, 8 | AW550681 | | ESTs | 1.671987076 |
| 10, 12, 23 | AA060863 | | *Mus musculus* TSC22-related inducible leucine zipper 1b (Tilz1b) mRNA, complete cds | 2.567506201 |
| 10, 14, 14 | C87169 | | | 1.742126569 |
| 10, 14, 9 | AW546455 | | ESTs, Moderately similar to nuclear factor of activated T-cells, cytoplasmic 3 [*H. sapiens*] | 3.70859768 |
| 10, 18, 7 | AW553938 | | ESTs | 1.784945891 |
| 10, 19, 13 | AU023882 | Brca2 | breast cancer 2 | 2.117866055 |

SUPPLEMENTAL TABLE 1-continued

| ID | Acc No | Gene | Description | N/F ratio |
|---|---|---|---|---|
| 10, 19, 8 | AW551966 | | ESTs | 1.693995246 |
| 10, 2, 11 | AU015358 | Ubl1a2-pending | ubiquitin-like 1 (sentrin) activating enzyme subunit 2 | 5.365114455 |
| 10, 2, 7 | AW552108 | | ESTs, Highly Similar to SUCCINATE DEHYDROGENASE CYTOCHROME B560 SUBUNIT PRECURSOR [Bos taurus] | 2.657065897 |
| 10, 2, 9 | AU042207 | | ESTs, Weakly similar to N-methyl-D-aspartate receptor glutamate-binding chain [R. norvegicus] | 3.272488788 |
| 10, 21, 7 | AW554737 | | ESTs, Weakly similar to KIAA0512 protein [H. sapiens] | 2.514867936 |
| 10, 22, 9 | AW547900 | | ESTs | 1.702197367 |
| 10, 23, 9 | AW547928 | | ESTs | 4.426096507 |
| 10, 3, 10 | AU040764 | | ESTs | 2.305827433 |
| 10, 3, 17 | AW543960 | | EST | 1.98385959 |
| 10, 3, 6 | AW554947 | | ESTs, Highly similar to translation initiation factor IF2 [H. sapiens] | 3.625644265 |
| 10, 6, 10 | AU040830 | | ESTs, Weakly similar to 60S RIBOSOMAL PROTEIN L30A [Saccharomyces cerevisiae] | 4.091843934 |
| 10, 6, 16 | AW537188 | | | 2.913554588 |
| 10, 6, 8 | AW549332 | | ESTs | 2.023735431 |
| 10, 8, 16 | AW537237 | Arl6ip | ADP-ribosylation-like factor 6 interacting protein | 3.427115027 |
| 10, 8, 21 | AA240506 | | | 1.723892614 |
| 10, 8, 26 | AA386680 | Kif5b | kinesin family member 5B | 2.130805311 |
| 10, 9, 18 | AW538432 | Rhoip3-pending | Rho interacting protein 3 | 3.330216015 |
| 11, 14, 15 | C80446 | | ESTs | 6.597732193 |
| 11, 15, 8 | AW551715 | | | 2.618954202 |
| 11, 17, 9 | AW547189 | | ESTs, Weakly similar to membrane glycoprotein [M. musculus] | 1.872805389 |
| 11, 22, 18 | AW543115 | | ESTs | 3.005219811 |
| 11, 22, 7 | AW555297 | | ESTs | 2.16749597 |
| 11, 3, 7 | AW552496 | | | 2.877924191 |
| 11, 3, 9 | AU042851 | | | 2.235921475 |
| 11, 4, 12 | AU018955 | | ESTs | 2.195691464 |
| 11, 6, 22 | AA138394 | | ESTs | 2.169177669 |
| 11, 8, 10 | AU043242 | | ESTs, Weakly similar to ORF YKR081c [S. cerevisiae] | 2.340501043 |
| 12, 10, 18 | AW538403 | | Mus musculus formin binding protein 11 (FBP11) mRNA, complete cds | 3.04888214 |
| 12, 11, 10 | AU043911 | | ESTs, Weakly similar to UBIQUITIN-CONJUGATING ENZYME E2-17 KD 2 [Mus musculus] | 2.769540325 |
| 12, 11, 6 | AW555759 | Phb | prohibitin | 2.761699761 |
| 12, 13, 18 | AW538517 | | ESTs | 4.507048384 |
| 12, 14, 3 | AI448261 | | Mus musculus serine-threonine kinase receptor-associated protein mRNA, complete cds | 1.962139554 |
| 12, 15, 13 | AU023751 | | ESTs, Highly similar to HPBRII-7 protein [H. sapiens] | 5.426224824 |
| 12, 16, 17 | AW545323 | | | 5.843973021 |
| 12, 16, 9 | AW546487 | Mns1 | meiosis-specific nuclear structural protein 1 | 1.788191829 |
| 12, 18, 6 | AW556673 | Anxa7 | annexin A7 | 2.036952459 |
| 12, 18, 9 | AW547603 | | ESTs | 3.808619679 |
| 12, 19, 6 | AW556706 | | ESTs | 3.094896437 |
| 12, 2, 11 | AU015298 | | ESTs, Moderately similar to dJ30M3.3 [H. sapiens] | 1.998244621 |
| 12, 20, 9 | AW547693 | | ESTs | 3.55440963 |
| 12, 21, 18 | AW539791 | | ESTs, Weakly similar to coded for by C. elegans cDNAs GenBank: [C. elegans] | 6.21796016 |
| 12, 21, 7 | AW554706 | | ESTs, Highly similar to hypothetical protein [H. sapiens] | 2.357478513 |
| 12, 22, 18 | AW539811 | Cdc10 | cell division cycle 10 homolog (S. cerevisiae) | 3.902125311 |
| 12, 22, 7 | AW554761 | | ESTs | 2.541961009 |
| 12, 23, 7 | AW554784 | | ESTs, Weakly similar to Cxorf5 [H. sapiens] | 2.147980173 |
| 12, 3, 12 | AU024765 | | | 4.02111663 |
| 12, 3, 18 | AA529949 | | ESTs | 2.027161144 |
| 12, 4, 10 | AU040750 | | ESTs, Highly similar to VACUOLAR ASSEMBLY PROTEIN VPS41 HOMOLOG [H. sapiens] | 1.766860604 |
| 12, 4, 3 | AI427886 | | ESTs, Highly similar to RAS-RELATED PROTEIN RAB-28 [R. norvegicus] | 2.694100196 |
| 12, 5, 16 | AW537132 | Gdap2 | ganglioside-induced differentiation-associated-protein 2 | 3.002468515 |
| 12, 8, 19 | AA285584 | | Mus musculus strain Swiss Webster/NIH actin-associated protein palladin mRNA, partial cds | 3.124624175 |
| 13, 15, 7 | AW554567 | Fkbp1a | FK506 binding protein 1a (12 kDa) | 2.653957746 |
| 13, 17, 7 | AW554607 | Ptk9r-pending | related protein | 2.088525057 |
| 13, 18, 12 | AU015048 | | ESTs | 3.334654393 |
| 13, 2, 10 | AU043380 | | ESTs, Highly similar to RER1 PROTEIN [Saccharomyces cerevisiae] | 1.922629478 |
| 13, 2, 14 | C85794 | | ESTs, Weakly similar to myelin transcription factor 1-like [M. musculus] | 2.142786048 |
| 13, 2, 16 | AW537070 | | ESTs | 1.932096917 |
| 13, 20, 9 | AW548914 | | Mus musculus receptor activity modifying protein 2 mRNA, complete cds | 3.229667371 |
| 13, 21, 8 | AW552636 | | | 1.651243516 |
| 13, 22, 16 | C78511 | Biklk | Bcl2-interacting killer-like | 2.2503145 |
| 13, 23, 8 | AW552679 | | ESTs | 2.162111394 |
| 13, 3, 10 | AU043443 | | ESTs, Highly similar to TRAM PROTEIN [Canis familiaris] | 4.011298228 |
| 13, 4, 7 | AW553519 | | ESTs, Highly similar to DNA-DIRECTED RNA POLYMERASE II 19 KD POLYPEPTIDE [Glycine max] | 1.727583809 |
| 13, 5, 11 | AU016361 | | EST | 2.107962946 |
| 14, 1, 3 | AI429145 | | ESTs | 4.812765403 |
| 14, 11, 12 | AU020132 | Odc | ornithine decarboxylase, structural | 2.890092488 |

SUPPLEMENTAL TABLE 1-continued

| ID | Acc No | Gene | Description | N/F ratio |
|---|---|---|---|---|
| 14, 11, 18 | AW538715 | Ass1 | arginosuccinate synthetase 1 | 4.609205297 |
| 14, 13, 12 | AU020218 | Zrf2 | zuotin related factor 2 | 2.627413283 |
| 14, 14, 11 | AU017036 | | ESTs, Highly similar to UBIQUITIN-CONJUGATING ENZYME E2-17 KD 3 [*Homo sapiens: Rattus norvegicus*] | 2.0788242 |
| 14, 14, 16 | C76660 | | ESTs, Moderately similar to KIAA0663 protein [*H. sapiens*] | 2.172287352 |
| 14, 15, 14 | C87551 | Eif4e-ps | eukaryotic translation initiation factor 4E | 1.966834915 |
| 14, 15, 24 | AA030786 | | ESTs | 2.240373072 |
| 14, 18, 18 | AW541471 | Tfg | Trk-fused gene | 1.678687844 |
| 14, 20, 10 | AU046294 | Magoh | mago-nashi homolog, proliferation-associated (*Drosophila*) | 2.353138844 |
| 14, 20, 9 | AW548203 | | ESTs | 3.090924081 |
| 14, 22, 13 | AU018430 | | ESTs | 3.818903275 |
| 14, 7, 20 | AA220617 | Bak | Bcl2 homologous antagonist/killer | 2.461291028 |
| 14, 8, 16 | AW537454 | | ESTs | 2.21447486 |
| 14, 9, 17 | AW544435 | | | 2.000189626 |
| 15, 10, 13 | AU023604 | | ESTs, Weakly similar to SEX-LETHAL PROTEIN, FEMALE-SPECIFIC [*Drosophila melanogaster*] | 2.569110342 |
| 15, 12, 18 | AW539416 | | ESTs | 2.348876157 |
| 15, 13, 24 | AA031056 | Mcmd5 | mini chromosome maintenance deficient 5 (*S. cerevisiae*) | 2.391689429 |
| 15, 14, 5 | AI326287 | | ESTs, Highly similar to TUBULIN ALPHA-4 CHAIN [*Gallus gallus*] | 2.054481753 |
| 15, 15, 18 | AW539519 | | ESTs | 2.341527019 |
| 15, 16, 18 | AW539538 | | ESTs | 2.611916565 |
| 15, 22, 17 | AW536987 | Snta1 | syntrophin, acidic 1 | 2.464853599 |
| 15, 23, 14 | AU022589 | | ESTs | 1.824462022 |
| 15, 3, 12 | AU019284 | | ESTs | 2.059174381 |
| 15, 6, 15 | C79548 | | ESTs | 1.690129068 |
| 15, 6, 26 | AA415370 | | ESTs | 2.257900982 |
| 15, 9, 18 | AW539347 | | ESTs | 4.447072022 |
| 16, 10, 5 | AI323620 | Hkp1 | House-keeping protein 1 | 1.640331493 |
| 16, 10, 6 | AW555997 | | EST | 1.630674405 |
| 16, 12, 18 | AW538700 | | ESTs | 2.617538557 |
| 16, 12, 24 | AA027451 | | | 2.614310944 |
| 16, 13, 7 | AW553990 | | ESTs | 4.108364998 |
| 16, 14, 24 | AA030061 | | | 2.621208402 |
| 16, 15, 11 | AU017015 | | | 3.502797318 |
| 16, 15, 16 | C76678 | | *Mus musculus* mRNA for Sid6061p, complete cds | 3.720028548 |
| 16, 16, 14 | C87531 | | ESTs | 2.99145001 |
| 16, 17, 10 | AU046028 | | ESTs, Moderately similar to RNA polymerase II transcription factor SIII p18 subunit [*R. norvegicus*] | 2.467860062 |
| 16, 17, 15 | C80210 | | ESTs | 7.295687026 |
| 16, 17, 17 | AW545676 | | ESTs | 2.591383664 |
| 16, 18, 9 | AW548061 | | ESTs, Weakly similar to unknown [*C. elegans*] | 3.032513144 |
| 16, 19, 11 | AU018045 | | | 3.219857865 |
| 16, 2, 12 | AU018486 | Ssb | Sjogren syndrome antigen B | 3.979536441 |
| 16, 20, 18 | AW541494 | Surf4 | surfeit gene 4 | 3.591874393 |
| 16, 21, 10 | AU041374 | | | 1.784477197 |
| 16, 21, 17 | AW536576 | Tex9 | testis expressed gene 9 | 2.671550442 |
| 16, 23, 13 | AU018409 | ArhA | Rho family GTpase | 3.530268774 |
| 16, 3, 11 | AU015646 | Rex3 | reduced expression 3 | 2.071644406 |
| 16, 4, 9 | AU042578 | | | 2.015407334 |
| 16, 6, 14 | C86226 | | | 5.44261442 |
| 16, 8, 14 | C86301 | | ESTs | 2.179294751 |
| 16, 8, 15 | C79036 | | EST | 3.875693403 |
| 16, 9, 14 | C86367 | | ESTs, Weakly similar to BAT2 [*M. musculus*] | 2.375988234 |
| 17, 17, 6 | AW557130 | Xist | inactive X specific transcripts | 1.697891896 |
| 17, 18, 8 | AW551743 | | ESTs, Moderately similar to WD-REPEAT PROTEIN SAZD [*H. sapiens*] | 1.807778023 |
| 17, 20, 14 | C88038 | | | 1.808900725 |
| 17, 22, 6 | AW558021 | | ESTs | 2.219679067 |
| 17, 23, 18 | AW543447 | | | 3.028866015 |
| 17, 6, 11 | AU016133 | | ESTs, Weakly similar to MSSP [*M. musculus*] | 2.213009807 |
| 18, 22, 6 | AW557547 | | | 2.432430534 |
| 18, 7, 16 | AW537221 | Fgfrp | fibroblast growth factor regulated protein | 2.648558726 |
| 19, 1, 16 | AW536849 | Ccnb1-rs1 | cyclin B1, related sequence 1 | 3.255108538 |
| 19, 10, 12 | AU020382 | | | 6.589303975 |
| 19, 13, 12 | AU020575 | | ESTs, Moderately similar to HYPOTHETICAL 27.1 KD PROTEIN CCE1-CAP1 INTERGENIC REGION [*Saccharomyces cerevisiae*] | 2.037569931 |
| 19, 14, 17 | AW536101 | | *Mus musculus* mRNA for phosphorylated adaptor for RNA export (PHAX gene) | 3.313622909 |
| 19, 15, 24 | AA030810 | | ESTs, Highly similar to AF161432_1 HSPC314 [*H. sapiens*] | 2.043627079 |
| 19, 16, 17 | AW536142 | | ESTs, Weakly similar to unknown [*R. norvegicus*] | 1.981339461 |
| 19, 18, 6 | AW557108 | | ESTs | 1.981762536 |
| 19, 19, 18 | AW542930 | | ESTs | 1.953216474 |
| 19, 19, 8 | AW552398 | | ESTs, Moderately similar to TRANSCRIPTION INITIATION FACTOR TFIID 28 KD SUBUNIT [*H. sapiens*] | 4.263787523 |
| 19, 20, 19 | AA276043 | Fbp1 | fructose bisphosphatase 1 | 1.815207277 |
| 19, 22, 8 | AW552461 | | ESTs, Weakly similar to SKD1 PROTEIN [*Mus musculus*] | 1.629936776 |
| 19, 23, 15 | C85347 | | | 5.69154099 |
| 19, 23, 9 | AW548671 | | ESTs | 1.881136659 |
| 19, 3, 26 | AA388122 | Mem3 | Maternal embryonic message 3 | 2.374556107 |

SUPPLEMENTAL TABLE 1-continued

| ID | Acc No | Gene | Description | N/F ratio |
|---|---|---|---|---|
| 19, 5, 15 | C79184 | Kpna2 | karyopherin (importin) alpha 2 | 4.483193007 |
| 19, 5, 16 | AW537587 | | | 4.458135946 |
| 19, 5, 8 | AW549980 | | ESTs, Highly similar to UBIQUITIN-CONJUGATING ENZYME E2-17 KD [Drospohila melanogaster] | 3.304680342 |
| 19, 6, 25 | W82690 | | ESTs | 2.097848007 |
| 19, 7, 11 | AU016110 | | Mus musculus heat shock protein (HSPC030) mRNA, complete cds | 3.031383324 |
| 19, 7, 14 | C86564 | | | 1.733344896 |
| 19, 8, 7 | AW553398 | | EST | 4.024687885 |
| 2, 1, 11 | AU015271 | | ESTs | 2.714478478 |
| 2, 10, 16 | AW537279 | Macs | myristoylated alanine rich protein kinase C substrate | 5.47595949 |
| 2, 13, 11 | AU016670 | | ESTs | 2.480538118 |
| 2, 14, 9 | AW546453 | | ESTs | 2.732905185 |
| 2, 15, 7 | AW553809 | Rnasei | ribonuclease L (2',5'-oligoisoadenylate synthetase-dependent) inhibitor | 3.127019793 |
| 2, 16, 12 | AU021072 | | ESTs, Weakly similar to unknown [R. norvegicus] | 3.691199965 |
| 2, 16, 13 | AU023815 | | ESTs, Weakly similar to (defline not available 5901816) [D. melanogaster] | 2.318446678 |
| 2, 21, 15 | C81194 | Hsp105 | heat shock protein, 105 kDa | 2.79345821 |
| 2, 22, 11 | AU017931 | | ESTs, Highly similar to ALPHA-1,6-MANNOSYL-GLYCOPROTEIN BETA-1,2-N-ACETYLGLUCOSAMINYLTRANSFERASE [Rattus norvegicus] | 2.050617842 |
| 2, 22, 18 | AW540941 | | ESTs, Highly similar to CYTOCHROME C OXIDASE POLYPEPTIDE VIB [Homo sapiens] | 2.115484663 |
| 2, 22, 8 | AW552025 | | ESTs | 1.863596817 |
| 2, 23, 14 | AU021850 | Semcap2 | semaF cytoplasmic domain associated protein 2 | 1.835494893 |
| 2, 3, 23 | AA034561 | Fen1 | Flap structure specific endonuclease 1 | 2.587417174 |
| 2, 7, 11 | AU015537 | | ESTs, Highly similar to H<BETA>58 PROTEIN [Mus musculus] | 1.730063182 |
| 20, 1, 13 | AU021834 | | ESTs | 2.802694822 |
| 20, 10, 18 | AW538407 | Slc20a1 | solute carrier family 20, member 1 | 2.767681717 |
| 20, 13, 14 | C87110 | | ESTs | 3.327762139 |
| 20, 16, 14 | C87205 | | ESTs, Weakly similar to C44B9.1 [C. elegans] | 3.701990317 |
| 20, 17, 13 | AU023806 | Rock1 | Rho-associated coiled-coil forming kinase 1 | 2.714535436 |
| 20, 17, 17 | AW545339 | Ate1 | arginine-tRNA-protein transferase 1 | 2.016693199 |
| 20, 17, 25 | W87153 | | ESTs, Moderately similar to HYPOTHETICAL 21.5 KD PROTEIN C08B11.9 IN CHROMOSOME II [Caenorhabditis elegans] | 1.928120788 |
| 20, 18, 12 | AU021126 | | ESTs | 4.030388791 |
| 20, 18, 17 | AW536320 | Orc4 | origin recognition complex, subunit 4 | 2.55331517 |
| 20, 18, 8 | AW550920 | | ESTs | 3.16437003 |
| 20, 18, 9 | AW547604 | | ESTs, Weakly similar to ORF YOL071w [S. cerevisiae] | 2.704938801 |
| 20, 19, 19 | AA066250 | | ESTs, Weakly similar to BC-2 protein [H. sapiens] | 3.430116366 |
| 20, 19, 8 | AW551944 | | ESTs, Highly similar to Similar to D. melanogaster parallel sister chromatids protein [H. sapiens] | 2.767267283 |
| 20, 2, 26 | AA413090 | | ESTs, Moderately similar to unknown protein IT12 [H. sapiens] | 2.08408988 |
| 20, 20, 8 | AW551959 | Cul1 | cullin 1 | 3.040828115 |
| 20, 21, 19 | AA068436 | | ESTs, Highly similar to unknown [R. norvegicus] | 5.647684222 |
| 20, 22, 7 | AW554765 | | ESTs, Moderately similar to tpr protein [H. sapiens] | 2.231202975 |
| 20, 23, 14 | AU021819 | Top1 | topoisomerase (DNA) I | 3.548400292 |
| 20, 3, 3 | AI427786 | | EST | 2.055546444 |
| 20, 3, 5 | AW557661 | Taldo1 | transaldolase 1 | 3.573769539 |
| 20, 6, 22 | AA154465 | | ESTs, Highly similar to similar to human DNA-binding protein 5. [H. sapiens] | 3.125092795 |
| 20, 6, 8 | AW549269 | | ESTs | 2.555555862 |
| 20, 7, 13 | AU022791 | | | 3.776946978 |
| 20, 7, 15 | C78755 | | ESTs | 3.382550001 |
| 20, 7, 16 | AW537202 | Dhfr | dihydrofolate reductase | 2.653293004 |
| 20, 9, 11 | AU016480 | | ESTs, Highly similar to 40S RIBOSOMAL PROTEIN S25 [Homo sapiens] [Rattus norvegicus] | 2.434092714 |
| 20, 9, 17 | AW544140 | D10Wsu52e | DNA segment, Chr 10, Wayne State University 52, expressed | 4.683018189 |
| 20, 9, 9 | AU042440 | | ESTs, Weakly similar to BRAIN SPECIFIC POLYPEPTIDE PEP-19 [Rattus norvegicus: Mus musculus] | 3.114535048 |
| 21, 1, 9 | AU042135 | | ESTs, Moderately similar to protocadherin-3 [R. norvegicus] | 2.539044703 |
| 21, 16, 17 | AW536295 | | | 1.819211222 |
| 22, 1, 8 | AW548397 | | ESTs, Weakly similar to cDNA EST EMBL: T01421 comes from this gene [C. elegans] | 2.636437564 |
| 22, 12, 14 | C86478 | | | 7.930960547 |
| 22, 14, 9 | AW546813 | | EST | 1.540520248 |
| 22, 16, 23 | AA073695 | Mea1 | male enhanced antigen 1 | 3.681248673 |
| 22, 23, 18 | AW542425 | | ESTs | 3.112255862 |
| 22, 9, 17 | AW544437 | | ESTs | 2.28118451 |
| 23, 1, 6 | AW555565 | Zyx | zyxin | 2.929015914 |
| 23, 1, 7 | AW552671 | | ESTs | 1.800668505 |
| 23, 1, 8 | AW549119 | RIE2 | RIE2 protein | 2.108802 |
| 23, 11, 7 | AW553643 | | ESTs, Highly similar to LZIP-1 and LZIP-2 [M. musculus] | 1.727602528 |
| 23, 12, 10 | AU045213 | | ESTs | 1.57541576 |
| 23, 12, 15 | C80749 | | ESTs | 2.025627005 |
| 23, 12, 17 | AW536194 | | ESTs, Highly similar to CGI-35 protein [H. sapiens] | 5.045862039 |
| 23, 12, 6 | AW556475 | | ESTs | 2.718743502 |
| 23, 14, 13 | AU024490 | | ESTs, Highly similar to PROTEIN TRANSLATION FACTOR SUI1 HOMOLOG [Anonpheles gambiae] | 6.646581144 |
| 23, 14, 26 | AA052404 | CRIPT | CRIPT protein | 2.318310231 |
| 23, 16, 15 | C80954 | | | 2.051583281 |
| 23, 16, 25 | W97837 | D10Ertd322e | DNA segment, Chr 10, ERATO Doi 322, expressed | 2.494826439 |

SUPPLEMENTAL TABLE 1-continued

| ID | Acc No | Gene | Description | N/F ratio |
|---|---|---|---|---|
| 23, 18, 22 | AA183803 | | ESTs, Weakly similar to envelope polyprotein [*M. musculus*] | 1.732688267 |
| 23, 2, 12 | AU019219 | | EST | 2.108230415 |
| 23, 2, 16 | AW537048 | Ets2 | E26 avian leukemia oncogena 2,3' domain | 3.325078728 |
| 23, 2, 7 | AW552709 | | *Mus musculus* brain protein 44-like protein (Brp441) mRNA, complete cds | 2.521723313 |
| 23, 20, 14 | C88330 | | ESTs, Weakly similar to weak similarity to the yeast SSM4 protein [*C. elegans*] | 2.282437195 |
| 23, 20, 17 | AW536945 | | ESTs, Weakly similar to female sterile homeotic-related protein Frg-1 [*M. musculus*] | 3.37311499 |
| 23, 21, 10 | AU042018 | | ESTs | 3.02452904 |
| 23, 22, 16 | C78481 | Eif3 | eukaryotic translation initiation factor 3 | 5.424426041 |
| 23, 23, 17 | AW537006 | | ESTs | 1.696593042 |
| 23, 4, 6 | AW555631 | | ESTs, Highly similar to PUTATIVE RECEPTOR PROTEIN [*Homo sapiens*] | 2.488892742 |
| 23, 5, 15 | C79506 | | | 2.420211405 |
| 23, 5, 9 | AW545976 | Cops7a | COP9 (constitutive photomorphogenic), subunit 7a (*Arabidopsis*) | 2.297823068 |
| 23, 6, 16 | AW537694 | | ESTs, Highly similar to HYPOTHETICAL 109.5 KD PROTEIN IN PPA1-DAP2 INTERGENIC REGION [*Saccharomyces cerevisiae*] | 4.238918085 |
| 23, 7, 3 | AI426727 | | ESTs, Weakly similar to 5'-AMP-ACTIVATED PROTEIN KINASE, GAMMA-1 SUBUNIT [*M. musculus*] | 2.617120238 |
| 23, 7, 6 | AW556339 | | ESTs, Highly similar to RN protein [*R. norvegicus*] | 2.311016095 |
| 23, 8, 11 | AU017390 | | ESTs | 1.802786179 |
| 23, 8, 14 | C86919 | | | 4.016889422 |
| 23, 8, 24 | AA017991 | | ESTs | 2.483412396 |
| 24, 1, 14 | C85101 | | ESTs | 1.527940385 |
| 24, 1, 7 | AW552230 | | ESTs | 2.376848943 |
| 24, 12, 7 | AW553979 | | ESTs, Highly similar to TYROSINE-PROTEIN KINASE JAK1 [*Homo sapiens*] | 2.11242201 |
| 24, 14, 7 | AW554059 | | ESTs, Weakly similar to HYPOTHETICAL 15.9 KD PROTEIN IN GLNA-FDHE INTERGENIC REGION [*Escherichia coli*] | 2.945086458 |
| 24, 17, 11 | AU017987 | | ESTs, Weakly similar to NADH-CYTOCHROME B5 REDUCTASE [*R. norvegicus*] | 2.016928064 |
| 24, 18, 11 | AU018029 | | ESTs, Highly similar to cbp146 [*M. musculus*] | 3.428043044 |
| 24, 18, 19 | AA080156 | Kap | kidney androgen regulated protein | 3.158901378 |
| 24, 22, 25 | AA000038 | Usp23 | ubiquitin specific protease 23 | 3.137407556 |
| 24, 3, 13 | AU022218 | Ptp4a1 | protein tyrosine phosphatase 4a1 | 2.459877353 |
| 24, 5, 14 | C86208 | | ESTs | 4.60351847 |
| 24, 5, 16 | AW537358 | | ESTs, Weakly similar to cDNA EST yk338g10.5 comes from this gene [*C. elegans*] | 4.424107656 |
| 24, 7, 24 | AA013832 | Clpx | caseinolytic protease X (*E. coli*) | 3.183287717 |
| 24, 8, 16 | AW537419 | | ESTs | 2.296850796 |
| 24, 9, 21 | AA209964 | D11Moh34 | DNA segment, Chr 11, KL Mohlke 34 | 7.590178566 |
| 25, 18, 17 | AW536755 | | ESTs, Highly similar to similar to nuclear domain 10 protein NDP52 [*H. sapiens*] | 7.509323804 |
| 25, 19, 8 | AW552431 | Scp2 | sterol carrier protein 2, liver | 4.818202195 |
| 25, 22, 7 | AW555335 | | | 2.161464496 |
| 26, 10, 9 | AW546296 | | ESTs | 2.764721009 |
| 26, 19, 16 | C77513 | | ESTs, Highly similar to GUANINE NUCLEOTIDE-BINDING PROTEIN G(I)/G(S)/G(O) GAMMA-5 SUBUNIT [*Bos taurus; Rattus norvegicus*] | 1.935966462 |
| 26, 19, 8 | AW551969 | Prtb | proline rich protein expressed in brain | 3.399624829 |
| 26, 20, 9 | AW547818 | Fmr1 | fragile X mental retardation syndrome 1 homolog | 3.184148074 |
| 26, 21, 24 | AA031120 | Psma1 | proteasome (prosome, macropain) subunit, alpha type 1 | 2.663765326 |
| 26, 8, 17 | AW544153 | | ESTs | 1.877502862 |
| 27, 1, 17 | AW543439 | Fkbp4 | FK506 binding protein 4 (59 kDa) | 3.254740967 |
| 27, 10, 15 | C79409 | | | 1.66090225 |
| 27, 10, 16 | AW537744 | | *Mus musculus* protein inhibitor of activated STAT protein PIAS1 mRNA, complete cds | 2.159440423 |
| 27, 10, 17 | AW545798 | D13Abb1e | DNA segment, Chr 13, Abbott 1 expressed | 1.779679579 |
| 27, 11, 12 | AU020432 | | ESTs | 2.383793282 |
| 27, 11, 20 | AA265845 | | *Mus musculus* mRNA for heterogeneous nuclear ribonucleoprotein H | 2.185702249 |
| 27, 12, 14 | C86757 | | ESTs | 1.706875968 |
| 27, 12, 26 | W36917 | D17Wsu155e | DNA segment, Chr 17, Wayne State University 155, expressed | 1.967356236 |
| 27, 13, 17 | AW536071 | | | 2.574043367 |
| 27, 15, 14 | C87823 | | ESTs, Weakly similar to cDNA EST EMBL:T01156 comes from this gene [*C. elegans*] | 2.446705774 |
| 27, 15, 7 | AW554328 | | ESTs, Highly similar to RSP5 PROTEIN [*Saccharomyces cerevisiae*] | 3.913617092 |
| 27, 17, 9 | AW547193 | | | 2.222157441 |
| 27, 18, 19 | AA403949 | Capn12 | calpain 12 | 2.38344367 |
| 27, 18, 6 | AW557115 | | | 3.252730213 |
| 27, 2, 8 | AW548748 | | ESTs, Weakly similar to proline-rich protein [*M. musculus*] | 2.840416615 |
| 27, 20, 16 | C78065 | | ESTs | 1.707168222 |
| 27, 20, 18 | AW542945 | | ESTs | 1.832348729 |
| 27, 21, 18 | AW543112 | | | 1.910260087 |
| 27, 23, 4 | AI426498 | | *Mus musculus* radio-resistance/chemo-resistance/cell cycle checkpoint control protein (Rad9) mRNA, complete cds | 4.007328711 |
| 27, 4, 15 | C79174 | | ESTs | 4.058936269 |
| 27, 6, 12 | AU019031 | Hist4 | histone 4 protein | 2.341178338 |
| 27, 6, 26 | AA415519 | | ESTs, Weakly similar to HYPOTHETICAL 40.4 KD PROTEIN R06F6.5 IN CHROMOSOME II [*Caenorhabditis elegans*] | 2.101349422 |

SUPPLEMENTAL TABLE 1-continued

| ID | Acc No | Gene | Description | N/F ratio |
|---|---|---|---|---|
| 27, 7, 21 | AA189879 | | ESTs, Weakly similar to similar to Zinc finger, C2H2 type [*C. elegans*] | 1.878407963 |
| 27, 8, 23 | AA057995 | | ESTs, Moderately similar to AF151892_1 CGI-134 protein [*H. sapiens*] | 2.147568646 |
| 27, 8, 25 | W81857 | | ESTs, Highly similar to HYPOTHETICAL 39.7 KD PROTEIN C34E10.2 IN CHROMOSOME III [*Caenorhabditis elegans*] | 2.458320944 |
| 27, 9, 16 | AW537685 | | ESTs, Highly similar to HYPOTHETICAL 83.2 KD PROTEIN IN CHA1-APA1/DTP INTERGENIC REGION [*Saccharomyces cerevisiae*] | 2.342999287 |
| 27, 9, 17 | AW544704 | | ESTs, Weakly similar to CGI-90 protein [*H. sapiens*] | 1.864913487 |
| 27, 9, 26 | W14928 | Smpd1 | Sphingomyelin phosphodiesterase 1, acid lysosomal | 2.035892157 |
| 28, 11, 23 | AA051256 | Cbx5 | chromobox homolog 5 (*Drosophila* HP1a) | 1.994358091 |
| 28, 12, 18 | AW538480 | | ESTs, Moderately similar to serine proteinase inhibitor 6 [*M. musculus*] | 4.92457718 |
| 28, 17, 14 | C87270 | | ESTs | 2.583812733 |
| 28, 17, 5 | AI327096 | | *Mus musculus* neuronal calcium sensor-1 (NCS-1) mRNA, complete cds | 4.676318103 |
| 28, 18, 17 | AW536321 | | ESTs | 1.679945548 |
| 28, 19, 6 | AW556708 | | ESTs | 1.426373054 |
| 28, 19, 7 | AW553932 | | EST | 1.637328157 |
| 28, 21, 12 | AU021314 | | *Mus musculus* KOI-4 gene, partial cds | 3.064952305 |
| 28, 22, 19 | AA068665 | | ESTs, Weakly similar to AF152841_1 polymyositis scleroderma overlap syndrome [*M. musculus*] | 3.05957507 |
| 28, 23, 12 | AU015222 | | ESTs | 2.795922775 |
| 28, 23, 9 | AW547880 | | | 3.239702305 |
| 28, 4, 17 | AW543978 | | ESTs | 3.969831883 |
| 28, 6, 10 | AU040813 | | ESTs, Weakly similar to T23G11.9 [*C. elegans*] | 2.309549316 |
| 28, 6, 2 | AI449074 | | ESTs | 4.497049697 |
| 28, 7, 7 | AW552851 | | ESTs | 2.139124061 |
| 28, 9, 18 | AW538390 | | | 1.833998742 |
| 29, 10, 18 | AW539386 | | ESTs | 7.008050386 |
| 29, 10, 9 | AW547284 | | ESTs, Weakly similar to PYRROLINE-5-CARBOXYLATE REDUCTASE [*Glycine max*] | 2.049181802 |
| 29, 11, 13 | AU023662 | | | 20.59840816 |
| 29, 14, 17 | AW536258 | Tpp2 | tripeptidyl peptidase II | 1.835506405 |
| 29, 15, 4 | AI427491 | | ESTs, Highly similar to PROBABLE UBIQUITIN CARBOXYL-TERMINAL HYDROLASE [*Homo sapiens*] | 2.394177647 |
| 29, 18, 10 | AU041939 | | *Mus musculus* TBX1 protein mRNA, complete cds | 2.221932511 |
| 29, 19, 15 | C81124 | Hsp60 | heat shock protein, 60 kDa | 1.968544873 |
| 29, 20, 10 | AU042003 | | | 2.441024607 |
| 29, 3, 10 | AU043450 | Msh2 | mutS homolog 2 (*E. coli*) | 2.659901068 |
| 3, 1, 10 | AU041246 | | ESTs, Highly similar to 26S PROTEASE REGULATORY SUBUNIT 4 HOMOLOG [*Schizasaccharomyces pombe*] | 7.575991278 |
| 3, 1, 17 | AW543415 | | *Mus musculus* secretory carrier membrane protein 4 mRNA, complete cds | 3.643663528 |
| 3, 11, 17 | AW545809 | Mdu1 | antigen identified by monoclonal antibodies 4F2 | 1.791428539 |
| 3, 13, 16 | C76908 | | | 6.203526972 |
| 3, 13, 17 | AW536067 | Aop2 | anti-oxidant protein 2 | 2.425678079 |
| 3, 13, 7 | AW554240 | | ESTs, Highly similar to OLIGOSACCHARYL TRANSFERASE STT3 SUBUNIT HOMOLOG [*Caenorhabditis elegans*] | 2.752467221 |
| 3, 14, 10 | AU044892 | | ESTs | 1.705319286 |
| 3, 14, 24 | AA030271 | | ESTs | 2.483517776 |
| 3, 14, 6 | AW556999 | | ESTs, Moderately similar to hypothetical protein [*H. sapiens*] | 2.840617772 |
| 3, 15, 15 | C80485 | Zfr | zinc finger RNA binding protein | 4.204981315 |
| 3, 17, 20 | AA260352 | | *Mus musculus* cerebellar postnatal development protein-1 (Cpd1) mRNA, partial cds | 3.268033947 |
| 3, 18, 9 | AW548431 | | ESTs, Highly similar to CYTOCHROME C OXIDASE POLYPEPTIDE VIIB PRECURSOR [*Homo sapiens*] | 4.009096262 |
| 3, 19, 18 | AW542927 | Bcap31 | B-cell receptor-associated protein 31 | 5.066787673 |
| 3, 19, 6 | AW557152 | | ESTs, Highly similar to spliceosomal protein SAP 155 [*H. sapiens*] | 2.706136493 |
| 3, 19, 9 | AW548470 | | ESTs | 12.88458118 |
| 3, 2, 11 | AU015947 | | ESTs | 1.788247928 |
| 3, 20, 8 | AW552411 | Ech1 | enoyl coenzyme A hydratase 1, peroxisomal | 2.315044879 |
| 3, 23, 12 | AU015879 | | *Mus musculus* LIM-kinase1 (Limk1) gene, complete cds; Wbscr1 (Wbscr1) gene, alternative splice products, complete cds; and replication factor C, 40kDa subunit (Rfc2) gene, complete cds | 3.239108652 |
| 3, 3, 12 | AU018928 | | ESTs, Highly similar to TRAF4-associated factor 2 [*H. sapiens*] | 5.510048965 |
| 3, 4, 11 | AU016022 | Anxa4 | annexin A4 | 3.448280131 |
| 3, 4, 12 | AU018954 | | | 3.272069232 |
| 3, 5, 26 | AA413831 | LOC56463 | p100 co-activator | 7.850930684 |
| 3, 5, 5 | AW558170 | | ESTs | 1.841319116 |
| 3, 6, 22 | AA172774 | D16Wsu83e | DNA segment, Chr 16, Wayne State University 83, expressed | 7.71686883 |
| 3, 6, 24 | AA015136 | LOC56046 | hypothetical protein | 3.596271768 |
| 3, 6, 26 | AA422809 | | ESTs, Highly similar to KIAA0368 [*H. sapiens*] | 4.173186503 |
| 3, 7, 8 | AW550056 | | ESTs | 5.478942934 |
| 3, 9, 2 | AI666581 | | RIBOSOMAL PROTEIN S6 KINASE II ALPHA 1 | 2.016029612 |
| 30, 1, 11 | AU015616 | | ESTs, Weakly similar to cDNA EST yk338f6.5 comes from this gene [*C. el* [*C. elegans*] | 2.330288731 |
| 30, 1, 14 | C85143 | | | 2.940279646 |
| 30, 1, 16 | AW536713 | | ESTs | 2.28356006 |
| 30, 10, 5 | AI893564 | Anx5 | Annexin V | 2.032674021 |
| 30, 11, 7 | AW553280 | Itgb1 | integrin beta 1 (fibronectin receptor beta) | 2.003708956 |
| 30, 12, 14 | C86480 | Plp | proteolipid protein (myelin) | 2.746272119 |
| 30, 14, 12 | AU020233 | Arf1 | ADP-ribosylation factor 1 | 3.991526009 |

SUPPLEMENTAL TABLE 1-continued

| ID | Acc No | Gene | Description | N/F ratio |
|---|---|---|---|---|
| 30, 16, 12 | AU021489 | Omd | osteomodulin | 2.593848954 |
| 30, 16, 16 | C76750 | Hnrpa1 | heterogeneous nuclear ribonucleoprotein A1 | 4.582363217 |
| 30, 19, 14 | C87694 | | ESTs, Weakly similar to acid ceramidase [*M. musculus*] | 1.879731613 |
| 30, 2, 15 | C78024 | | | 1.973706153 |
| 30, 2, 19 | AA472933 | | ESTs, Highly similar to unknown [*H. sapiens*] | 2.602536474 |
| 30, 20, 8 | AW552159 | Atp2a2 | ATPase, Ca++ transporting, cardiac muscle, slow twitch 2 | 2.409551934 |
| 30, 21, 11 | AU018151 | | ESTs | 1.913900772 |
| 30, 21, 19 | AA068842 | Ubc2e | ubiquitin conjugating enzyme 2e | 2.435798543 |
| 30, 22, 15 | C85070 | | ESTs | 2.177609374 |
| 30, 22, 8 | AW552205 | Zfp101 | zinc finger protein 101 | 1.845671095 |
| 30, 23, 9 | AW548330 | | ESTs, Moderately similar to NADH-UBIQUINONE OXIDOREDUCTASE CHAIN 2 [*Mus musculus*] | 2.646892785 |
| 30, 3, 14 | C85216 | | | 48.97196172 |
| 30, 3, 16 | AW537334 | | ESTs, Weakly similar to signal recognition particle 54K protein [*M. musculus*] | 2.647412355 |
| 30, 5, 7 | AW553103 | | ESTs, Weakly similar to es 64 [*M. musculus*] | 2.470432192 |
| 30, 7, 16 | AW537446 | Tcea1 | transcription elongation factor A (SII), 1 | 3.353756593 |
| 30, 9, 13 | AU023128 | | ESTs, Highly similar to CAMP-DEPENDENT PROTEIN KINASE TYPE I-ALPHA REGULATORY CHAIN [*Homo sapiens*] | 2.971627282 |
| 31, 1, 5 | AW558291 | | ESTs | 2.31484213 |
| 31, 1, 7 | AW552672 | Btd | biotinidase | 1.873607374 |
| 31, 1, 8 | AW549121 | Hmg14 | high mobility group protein 14 | 5.305166988 |
| 31, 11, 7 | AW553645 | Slc12a2 | solute carrier family 12, member 2 | 5.209225843 |
| 31, 12, 7 | AW554493 | | | 2.108393101 |
| 31, 12, 9 | AW547310 | | ESTs | 2.724827548 |
| 31, 13, 8 | AW551817 | Madh4 | MAD homolog 4 (*Drosophila*) | 2.757229361 |
| 31, 14, 15 | C80862 | | ESTs, Moderately similar to (defline not available 5931553) [*M. musculus*] | 3.090776963 |
| 31, 14, 18 | AW539487 | Pabpc1 | poly A binding protein, cytoplasmic 1 | 3.2298131 |
| 31, 15, 24 | AA030846 | Coq7 | demethyl-Q 7 | 2.013748884 |
| 31, 18, 10 | AU041887 | | ESTs, Highly similar to HYPOTHETICAL 30.3 KD PROTEIN IN APE1/LAP4-CWP1 INTERGENIC REGION [*Saccharomyces cerevisiae*] | 5.573324729 |
| 31, 18, 8 | AW551918 | Ube2i | ubiquitin-conjugating enzyme E2I | 3.500959948 |
| 31, 2, 8 | AW548978 | | | 3.416858729 |
| 31, 22, 14 | AU022550 | | ESTs | 2.059326983 |
| 31, 3, 11 | AU016270 | | ESTs, Highly similar to CYCLIN-DEPENDENT KINASES REGULATORY SUBUNIT 2 [*Homo sapiens*] | 3.395812648 |
| 31, 6, 26 | AA414612 | Cappa1 | capping protein alpha 1 | 4.335956318 |
| 31, 8, 12 | AU020667 | Uchl3 | ubiquitin carboxyl-terminal esterase L3 (ubiquitin thiolesterase) | 3.225200079 |
| 31, 8, 13 | AU023550 | Fin14 | fibroblast growth factor inducible 14 | 2.195941034 |
| 31, 8, 20 | AA272115 | | ESTs | 2.392741899 |
| 31, 9, 7 | AW553602 | | ESTs, Weakly similar to (defline not available 6016842) [*M. musculus*] | 2.285573594 |
| 32, 10, 13 | AU023139 | | ESTs, Weakly similar to natural killer cell tumor-recognition protein [*M. musculus*] | 2.061470989 |
| 32, 18, 17 | AW536519 | | ESTs, Weakly similar to lens epithelium-derived growth factor [*H. sapiens*] | 2.623225239 |
| 32, 21, 11 | AU018130 | | ESTs, Weakly similar to cholesterol 25-hydroxylase [*M. musculus*] | 6.335735765 |
| 32, 23, 6 | AW557836 | | ESTs | 8.740904908 |
| 32, 9, 16 | AW537469 | | ESTs, Moderately similar to BB1 | 2.052267636 |
| 33, 11, 19 | AA423209 | Psme3 | Proteaseome (prosome, macropain) 28 subunit, 3 | 2.222939666 |
| 33, 15, 17 | AW536140 | Hsp86-1 | heat shock protein, 86 kDa 1 | 3.220069536 |
| 33, 15, 7 | AW554376 | Dlgh1 | discs, large homolog 1 (*Drosophila*) | 3.049574352 |
| 33, 18, 15 | C80708 | | ESTs, Weakly similar to 62D9.a [*D. melanogaster*] | 2.119484585 |
| 33, 18, 18 | AW542919 | | ESTs, Highly similar to KIAA0398 [*H. sapiens*] | 2.049586337 |
| 33, 19, 14 | C88028 | | ESTs, Highly similar to small membrane protein 1 [*H. sapiens*] | 3.66566524 |
| 33, 2, 8 | AW548794 | | ESTs | 1.861249227 |
| 33, 21, 5 | AI327246 | | ESTs, Weakly similar to titin [*M. musculus*] | 3.507243434 |
| 33, 3, 8 | AW549937 | Hdac2 | histone deacetylase 2 | 2.292864895 |
| 33, 6, 11 | AU016137 | Fth | ferritin heavy chain | 2.464959455 |
| 33, 6, 8 | AW550050 | | | 4.277912854 |
| 33, 8, 15 | C79363 | | *Mus musculus* hsp40 mRNA for heat shock protein 40, complete cds | 1.623760717 |
| 33, 9, 18 | AW538992 | | *Mus musculus* mRNA for 26S proteasome non-ATPase subunit | 4.76789816 |
| 34, 10, 14 | C86107 | Actn3 | actinin alpha 3 | 2.520902204 |
| 34, 13, 17 | AW545272 | | | 1.647750981 |
| 34, 18, 18 | AW539649 | | ESTs, Highly similar to DEK PROTEIN [*Homo sapiens*] | 2.542495091 |
| 34, 18, 20 | AA266868 | | ESTs, Highly similar to RIBOSOMAL PROTEIN S6 KINASE [*Homo sapiens*] | 2.364627315 |
| 34, 2, 14 | C81381 | | ESTs, Weakly similar to BcDNA.GH03108 [*D. melanogaster*] | 2.2321414 |
| 34, 2, 15 | C77692 | | EST | 2.004659901 |
| 34, 2, 26 | AA543829 | | ESTs, Weakly similar to CG17593 gene product [*D. melanogaster*] | 1.770333636 |
| 34, 21, 8 | AW552022 | Nudt5 | nudix (nucleoside diphosphate linked moiety X)-type motif 5 | 2.155260382 |
| 34, 23, 21 | AA213017 | Fmo3 | flavin containing monooxygenase 3 | 1.940084944 |
| 34, 6, 9 | AU042383 | | ESTs | 2.922097599 |
| 35, 11, 17 | AW545818 | | ESTs, Weakly similar to /prediction | 3.339835947 |
| 35, 13, 14 | C87726 | | *Mus musculus* mitotic checkpoint component Mad2 mRNA, complete cds | 2.391344308 |
| 35, 4, 15 | C79176 | | ESTs, Weakly similar to TYROSINE-PROTEIN KINASE JAK3 [*M. musculus*] | 2.826660135 |
| 35, 8, 9 | AU043040 | | | 2.289264614 |
| 36, 12, 7 | AW553719 | | ESTs | 2.383654235 |
| 36, 12, 9 | AW546347 | | *Mus musculus* geminin mRNA, complete cds | 2.181899423 |
| 36, 15, 12 | AU021009 | | *Mus musculus* cleavage and polyadenylation specificity factor 73 kDa subunit mRNA, complete cds | 1.731270685 |

SUPPLEMENTAL TABLE 1-continued

| ID | Acc No | Gene | Description | N/F ratio |
|---|---|---|---|---|
| 36, 16, 3 | AI451984 | Prim1 | DNA primase, p49 subunit | 2.250302092 |
| 36, 2, 8 | AW548009 | | ESTs, Highly similar to PTD014 [*H. sapiens*] | 2.346432008 |
| 36, 3, 16 | AW537083 | | ESTs, Highly similar to cellular apoptosis susceptibilty protein [*H. sapiens*] | 2.766532496 |
| 36, 3, 8 | AW549140 | | ESTs, Weakly similar to Peter Pan [*D. melanogaster*] | 2.379705926 |
| 36, 4, 11 | AU015435 | | ESTs | 2.654766001 |
| 36, 5, 10 | AU040801 | | ESTs, Highly similar to rer [*M. musculus*] | 3.236111635 |
| 36, 5, 25 | W62229 | Ube1c | ubiquitin-activating enzyme E1C | 5.477163155 |
| 37, 11, 18 | AW539443 | | | 4.636199091 |
| 37, 12, 6 | AW556511 | | ESTs | 1.84141389 |
| 37, 14, 12 | AU020998 | Plat | plasminogen activator, tissue | 2.599921486 |
| 37, 14, 2 | AI451597 | | EST | 2.740582523 |
| 37, 16, 6 | AW557336 | Vti1b-pending | vesicle transport through interaction with t-SNAREs 1b homolog | 1.877835528 |
| 37, 17, 18 | AW543524 | Ghrh | growth hormone releasing hormone | 3.731298401 |
| 37, 7, 11 | AU016461 | Ssfa1 | sperm specific antigen 1 | 2.512128647 |
| 37, 8, 14 | C86958 | | ESTs | 2.444945562 |
| 37, 8, 22 | AA161815 | | ESTs | 4.123898045 |
| 38, 1, 5 | AW557863 | | ESTs | 2.491298002 |
| 38, 18, 14 | C87642 | | ESTs, Weakly similar to coded for by C. elegans cDNAs GenBank: M88869 and T01933 [*C. elegans*] | 1.869067234 |
| 38, 20, 12 | AU021687 | | ESTs | 1.803038147 |
| 38, 20, 2 | AI464450 | | ESTs | 2.204202038 |
| 38, 3, 5 | AW557915 | Ezh1 | enhancer of zeste homolog 1 (*Drosophila*) | 2.416855801 |
| 38, 3, 7 | AW552394 | | ESTs | 2.487914695 |
| 38, 4, 9 | AU042629 | | ESTs | 2.392060207 |
| 38, 5, 12 | AU018693 | | | 1.983728331 |
| 38, 5, 5 | AW557968 | | EST | 3.514174584 |
| 39, 12, 20 | AA265633 | | ESTs | 3.087599296 |
| 39, 14, 25 | W97741 | | | 1.867206344 |
| 39, 15, 18 | AW539528 | D13Wsu177e | DNA segment, Chr 13, Wayne State University 177, expressed | 1.970460782 |
| 39, 19, 17 | AW536910 | | ESTs, Moderately similar to chromosome-associated protein-E [*H. sapiens* | 2.365185976 |
| 39, 19, 18 | AW543636 | Anxa5 | annexin A5 | 2.471442908 |
| 39, 21, 3 | AI447815 | | ESTs, Moderately similar to LUTHERAN BLOOD GROUP GLYCOPROTEIN PRECURSOR [*H. sapiens*] | 2.20379027 |
| 39, 4, 17 | AW544818 | Rab18 | RAB18, member RAS oncogene family | 3.109347054 |
| 39, 7, 24 | AA014196 | Glud | Glutamate dehydrogenase | 3.238249096 |
| 39, 8, 24 | AA020034 | | ESTs, Weakly similar to cleft lip and palate transmembrane protein 1 [*H. sapiens*] | 2.376903716 |
| 4, 1, 10 | AU040633 | | | 6.851119345 |
| 4, 1, 5 | AW557574 | Lrpap1 | low density lipoprotein receptor related protein, associated protein 1 | 3.789636371 |
| 4, 10, 17 | AW545006 | Psmb1 | proteasome (prosome, macropain) subunit, beta type 1 | 4.277781412 |
| 4, 10, 8 | AW549474 | | ESTs, Moderately similar to unknown [*H. sapiens*] | 3.314824736 |
| 4, 11, 17 | AW545119 | | ESTs | 7.994504577 |
| 4, 11, 18 | AW538456 | | ESTs | 1.80382642 |
| 4, 11, 6 | AW555755 | | ESTs | 2.562143842 |
| 4, 12, 18 | AW538474 | | ESTs, Highly similar to PUTATIVE SERINE/THREONINE-PROTEIN KINASE A [*Trypanosoma brucei brucei*] | 2.247826338 |
| 4, 12, 7 | AW553714 | Tlk | Tousled-like kinase (*Arabidopsis*) | 2.510671023 |
| 4, 13, 17 | AW545033 | | ESTs, Moderately similar to KIAA0007 [*H. sapiens*] | 5.424290287 |
| 4, 15, 9 | AW546427 | | ESTs, Highly similar to RAS-LIKE PROTEIN TC21 [*Homo sapiens*] | 2.78308135 |
| 4, 16, 25 | W83959 | | ESTs | 3.01450973 |
| 4, 18, 10 | AU045568 | | ESTs, Weakly similar to IgG Fc binding protein [*M. musculus*] | 3.362501582 |
| 4, 18, 18 | AW539607 | | ESTs, Weakly similar to All-1 protein +GTE form [*M. musculus*] | 3.099324211 |
| 4, 2, 26 | AA545607 | Mtf2 | metal response element binding transcription factor 2 | 3.777112474 |
| 4, 20, 11 | AU017822 | | ESTs, Weakly similar to NSP-like 1 [*M. musculus*] | 3.226784472 |
| 4, 21, 14 | AU021740 | | ESTs, Weakly similar to POSSIBLE GLOBAL TRANSCRIPTION ACTIVATOR SNF2L [*Caenorhabditis elegans*] | 4.128979953 |
| 4, 23, 11 | AU017911 | | ESTs, Weakly similar to implantation-associated protein [*R. norvegicus*] | 1.976753477 |
| 4, 3, 5 | AW557657 | Idh1 | Isocitrate dehydrogenase 1 (NADP+), soluble | 8.106563202 |
| 4, 4, 23 | AA041834 | Tk1 | Thymidine kinase 1 | 8.480042707 |
| 4, 4, 6 | AW554926 | | ESTs, Highly similar to PTB-ASSOCIATED SPLICING FACTOR [*Homo sapiens*] | 4.181277703 |
| 4, 6, 17 | AW544040 | | ESTs | 5.628414012 |
| 4, 6, 21 | AA208818 | Fxr1h | fragile X mental retardation gene, autosomal homolog | 2.574882839 |
| 40, 12, 18 | AW538705 | | | 3.202681524 |
| 40, 13, 8 | AW551167 | | ESTs | 2.085037733 |
| 40, 14, 18 | AW538766 | | ESTs, Weakly similar to HYPOTHETICAL UOG-1 PROTEIN [*M. musculus*] | 2.625140435 |
| 40, 17, 11 | AU017992 | Ktn1 | kinectin 1 | 1.910629157 |
| 40, 2, 16 | AW536696 | Ndufv1 | NADH dehydrogenase flavoprotein 1 | 3.16947838 |
| 40, 22, 12 | AU014587 | | ESTs, Highly similar to POLYADENYLATE-BINDING PROTEIN [Xenopu [*Xenopus laevis*] | 2.983364731 |
| 40, 23, 18 | AW542401 | | ESTs | 4.622707745 |
| 40, 4, 26 | AA473234 | | ESTs | 1.879559343 |
| 40, 5, 13 | AU022276 | Ask-pending | activator of S phase kinase | 1.801825864 |
| 40, 7, 22 | AA154888 | | | 2.045741456 |
| 41, 10, 13 | AU023417 | Xnp | X-linked nuclear protein | 2.30515632 |
| 41, 10, 17 | AW545835 | | *Mus musculus* Smt3A protein mRNA, complete cds | 4.7826417 |
| 41, 13, 10 | AU044944 | Rab11a | RAB11a, member RAS oncogene family | 3.257027215 |
| 41, 14, 10 | AU044964 | | | 2.561072945 |

SUPPLEMENTAL TABLE 1-continued

| ID | Acc No | Gene | Description | N/F ratio |
|---|---|---|---|---|
| 41, 15, 7 | AW554377 | | ESTs | 3.210449861 |
| 41, 18, 18 | AW542924 | | ESTs, Highly similar to hSgt1p [*H. sapiens*] | 1.661318391 |
| 41, 19, 8 | AW552438 | | ESTs, Moderately similar to (defline not available 5714400) [*M. musculus*] | 2.084900792 |
| 41, 23, 17 | AW536843 | Cct4 | chaperonin subunit 4 (delta) | 2.060855635 |
| 41, 3, 16 | AW537566 | | ESTs, Highly similar to HYPOTHETICAL PROTEIN C22G7.01C IN CHROMOSOME I [*Schizosaccaharomyces pombe*] | 4.125279614 |
| 41, 6, 17 | AW544660 | | ESTs | 1.666988225 |
| 41, 6, 26 | AA422973 | | ESTs, Moderately similar to AF161556_1 HSPC071 [*H. sapiens*] | 2.652581493 |
| 41, 7, 26 | AA465980 | | ESTs, Highly similar to HYPOTHETICAL 51.6 KD PROTEIN F59B2.5 IN CHROMOSOME III [*Caenorhabditis elegans*] | 4.083961131 |
| 41, 8, 26 | AA413694 | Rab7 | RAB7, member RAS oncogene family | 2.948415605 |
| 41, 9, 11 | AU017162 | Rpl5 | ribosomal protein L5 | 1.694246937 |
| 42, 1, 11 | AU015293 | | ESTs | 2.490522603 |
| 42, 11, 18 | AW538500 | | | 2.199109471 |
| 42, 11, 9 | AW546328 | | | 1.838459869 |
| 42, 14, 7 | AW553808 | | ESTs, Weakly similar to (defline not available 5579011) [*M. musculus*] | 1.766528451 |
| 42, 16, 16 | C76345 | | | 1.894584674 |
| 42, 18, 17 | AW536342 | | ESTs, Weakly similar to RSP-1 PROTEIN [*Mus musculus*] | 2.542866132 |
| 42, 18, 19 | AA105717 | Ddx20 | DEAD/H (Asp-Glu-Ala-Asp/His) box polypeptide 20 | 1.909088139 |
| 42, 19, 17 | AW536359 | | ESTs, Highly similar to UNR PROTEIN [*Rattus norvegicus*] | 4.798453644 |
| 42, 2, 8 | AW548051 | | ESTs | 2.874137372 |
| 42, 21, 2 | AI465270 | | ESTs | 1.931439126 |
| 42, 22, 17 | AW536450 | | ESTs | 2.60324142 |
| 42, 22, 6 | AW557553 | | ESTs | 4.423763724 |
| 42, 23, 18 | AW541003 | | ESTs | 2.283016335 |
| 42, 23, 9 | AW547945 | | ESTs, Weakly similar to ZIP-kinase [*M. musculus*] | 3.234869937 |
| 42, 5, 11 | AU015486 | Cappa2 | capping protein alpha 2 | 3.894401118 |
| 42, 6, 17 | AW544098 | | ESTs | 1.800285186 |
| 42, 6, 25 | W67062 | | ESTs, Weakly similar to CST1_HUMAN CLEAVAGE STIMULATION FACTOR, 50 KD SUBUNIT [*H. sapiens*] | 3.272511033 |
| 42, 6, 26 | AA467238 | | ESTs, Moderately similar to AF155107_1 NY-REN-37 antigen [*H. sapiens*] | 2.025843113 |
| 43, 14, 24 | AA024255 | Slc22a5 | solute carrier family 22 (organic cation transporter), member 5 | 1.880231831 |
| 43, 15, 19 | AA396298 | | *Mus musculus* mRNA for RNase 4, complete cds | 3.470957341 |
| 43, 15, 9 | AW547111 | Myhca | myosin heavy chain, cardiac muscle, adult | 3.155653539 |
| 43, 16, 4 | AI431019 | | ESTs | 3.158363336 |
| 43, 18, 6 | AW557123 | Dok1 | downstream of tyrosine kinase 1 | 1.906960586 |
| 43, 19, 14 | C87993 | Mtf1 | metal response element binding transcription factor 1 | 1.998123193 |
| 43, 20, 14 | C88019 | | EST | 2.320518989 |
| 43, 22, 15 | C85340 | | ESTs | 2.94188799 |
| 43, 22, 17 | AW536816 | | ESTs, Weakly similar to ZW10 interactor Zwint [*H. sapiens*] | 3.211073781 |
| 43, 23, 18 | AW543413 | | ESTs | 2.826341304 |
| 43, 23, 8 | AW552337 | | ESTs, Highly similar to RAS-RELATED PROTEIN RAB-6 [*Homo sapiens*] | 2.641220499 |
| 43, 5, 22 | AA162800 | Cul3 | cullin 3 | 4.189740174 |
| 44, 14, 13 | AU023746 | Tacc3 | transforming, acidic coiled-coil containing protein 3 | 4.176773893 |
| 44, 2, 16 | AW536480 | | ESTs | 2.67138219 |
| 44, 22, 17 | AW536428 | | ESTs, Moderately similar to BLEOMYCIN HYDROLASE [*Oryctolagus cuniculus*] | 2.170625189 |
| 44, 6, 16 | AW537169 | | ESTs, Weakly similar to misato [*D. melanogaster*] | 3.140606246 |
| 45, 1, 8 | AW549019 | | ESTs | 2.220328696 |
| 45, 10, 17 | AW536183 | Cct3 | chaperonin subunit 3 (gamma) | 2.05541031 |
| 45, 13, 11 | AU017619 | Ak3 | adenylate kinase 3 | 3.186508194 |
| 45, 18, 17 | AW536926 | | ESTs, Highly similar to KIAA0601 protein [*H. sapiens*] | 2.282157312 |
| 45, 4, 10 | AU043481 | | ESTs | 3.309811859 |
| 45, 4, 11 | AU016359 | | ESTs, Weakly similar to G PROTEIN PATHWAY SUPPRESSOR 1 [*R. norvegicus*] | 1.949742502 |
| 45, 7, 14 | C86941 | | | 15.31639347 |
| 45, 7, 6 | AW556373 | | ESTs, Highly similar to HAM1 PROTEIN [*Saccharomyces cerevisiae*] | 2.228965982 |
| 45, 7, 9 | AW546162 | | ESTs, Weakly similar to CARG-BINDING FACTOR-A [*M. musculus*] | 2.189482216 |
| 45, 9, 18 | AW539377 | | | 2.065750725 |
| 45, 9, 9 | AW546244 | | ESTs, Weakly similar to G protein-coupled receptor kinase 6, splice variant A [*M. musculus*] | 1.671515989 |
| 46, 10, 5 | AI573427 | Catnb | Catenin beta | 2.08164667 |
| 46, 10, 6 | AW556036 | | ESTs, Weakly similar to Weak similarity in middle of protein to HIV-1 TAT protein [*S. cerevisiae*] | 1.693522568 |
| 46, 14, 10 | AU044566 | | ESTs, Highly similar to VACUOLAR ATP SYNTHASE SUBUNIT D [*Bos taurus*] | 2.897417571 |
| 46, 16, 11 | AU018011 | | *Mus musculus* truncated SON protein (Son) mRNA, complete cds | 2.729861304 |
| 46, 16, 18 | AW538862 | | ESTs, Weakly similar to P9513.2 gene product [*S. cerevisiae*] | 3.054927766 |
| 46, 17, 18 | AW541468 | | ESTs, Highly similar to HYPOTHETICAL 64.5 KD PROTEIN ZK652.9 IN CHROMOSOME III [*Caenorhabditis elegans*] | 2.985037992 |
| 46, 2, 12 | AU018547 | | EST, Weakly similar to NaPi-2 beta [*R. norvegicus*] | 2.580324249 |
| 46, 2, 16 | AW536727 | | ESTs, Highly similar to HYPOTHETICAL 18.5 KD PROTEIN C12G12.05 IN CHROMOSOME I [*Schizosaccharomyces pombe*] | 2.254945336 |
| 46, 20, 7 | AW555047 | | *Mus musculus* major histocompatibility complex region NG27, NG28, RPS28, NADH oxireductase, NG29, KIFC1, Fas-binding protein, BING1, tapasin, RalGDS-like, KE2, BING4, beta 1,3-galactosyl transferase, and RPS18 genes, complete cds: Sacm21 gene, partial cd | 3.290258007 |

SUPPLEMENTAL TABLE 1-continued

| ID | Acc No | Gene | Description | N/F ratio |
|---|---|---|---|---|
| 46, 22, 3 | AI447150 | | *Mus musculus* insulin-like growth factor I receptor mRNA, complete cds | 1.805486723 |
| 46, 22, 9 | AW548322 | Pctk1 | PCTAIRE-motif protein kinase 1 | 12.057525 |
| 47, 1, 13 | AU022611 | | | 2.776415523 |
| 47, 1, 16 | AW537042 | | ESTs | 1.729832182 |
| 47, 1, 3 | AI426662 | | EST | 4.156422912 |
| 47, 10, 17 | AW536175 | Adh5 | alcohol dehydrogenase 5 | 2.650134514 |
| 47, 11, 9 | AW547270 | | ESTs, Weakly similar to Smarce1-related protein [*M. musculus*] | 1.624951679 |
| 47, 12, 17 | AW536197 | | *Mus musculus* Tera (Tera) mRNA, complete cds | 8.192347763 |
| 47, 12, 6 | AW556482 | | ESTs, Moderately similar to hypothetical protein [*H. sapiens*] | 2.303394618 |
| 47, 13, 18 | AW539474 | | ESTs | 2.191349291 |
| 47, 13, 8 | AW551820 | | ESTs, Highly similar to HYPOTHETICAL 37.2 KD PROTEIN C12C2.09C IN CHROMOSOME I [*Schizosaccaromyces pombe*] | 2.736097382 |
| 47, 14, 14 | C88094 | | ESTs, Weakly similar to teg292 protein [*M. musculus*] | 14.31878982 |
| 47, 15, 18 | AW539529 | | ESTs | 2.64445063 |
| 47, 15, 2 | AI451613 | | ESTs, Highly similar to CYP4B1 [*M. musculus*] | 2.318913225 |
| 47, 15, 8 | AW551863 | | | 2.647171891 |
| 47, 19, 26 | W59202 | Stat3ip1-pending | signal transducer and activator of transcription 3 interacting protein 1 | 5.10228177 |
| 47, 2, 15 | C78609 | | ESTs, Highly similar to EUKARYOTIC INITIATION FACTOR 4 GAMMA [*Oryctolagus cuniculus*] | 2.621287161 |
| 47, 22, 18 | AW543722 | | ESTs, Highly similar to ARGINYL-TRNA SYNTHETASE [*Cricetulus longicaudatus*] | 7.643773902 |
| 47, 3, 10 | AU043407 | | ESTs, Highly similar to elongation factor SIII p15 subunit [*R. norvegicus*] | 3.0792624 |
| 47, 3, 9 | AW545936 | Cks1 | cyclin-dependent kinase regulatory subunit 1 | 3.202532356 |
| 47, 4, 11 | AU016321 | | ESTs | 1.943316321 |
| 47, 6, 7 | AW553551 | | ESTs, Highly similar to calcium-independent alpha-latrotoxin receptor homolog 2 [*R. norvegicus*] | 2.235170069 |
| 47, 7, 15 | C79581 | Msn | moesin | 3.670385369 |
| 47, 8, 8 | AW550493 | Dbi | diazepam binding inhibitor | 2.555492823 |
| 47, 8, 9 | AW546174 | Tgfb1i4 | transforming growth factor beta 1 induced transcript 4 | 5.668988417 |
| 48, 12, 7 | AW553985 | | ESTs | 1.839714835 |
| 48, 14, 15 | C80147 | Hdgf | hepatoma-derived growth factor | 2.579618455 |
| 48, 15, 7 | AW554081 | Adnp | activity-dependent neuroprotective protein | 3.055989327 |
| 5, 14, 12 | AU020992 | | ESTs | 2.568169261 |
| 5, 14, 5 | AI894273 | | ESTs, Moderately similar to HIGH MOBILITY GROUP-LIKE NUCLEAR PROTEIN 2 [*Saccharomyces cerevisiae*] | 13.46949084 |
| 5, 15, 14 | C88181 | | ESTs, Moderately similar to CCR4-ASSOCIATED FACTOR 1 [*M. musculus*] | 2.049163559 |
| 5, 15, 18 | AW539545 | | ESTs | 1.804206411 |
| 5, 16, 24 | AA030995 | Ppib | peptidylprolyl isomerase B | 5.335704428 |
| 5, 17, 12 | AU015031 | | ESTs | 1.870335095 |
| 5, 17, 18 | AW543515 | | ESTs, Highly similar to TRNA-PROCESSING PROTEIN SEN3 [*Saccharomyces cerevisiae*] | 2.600612477 |
| 5, 2, 12 | AU019262 | | ESTs, Weakly similar to DNAJ PROTEIN HOMOLOG MTJ1 [*M. musculus*] | 4.084659729 |
| 5, 22, 18 | AW543750 | | *M. musculus* mRNA for glutamyl-tRNA synthetase | 3.038063168 |
| 5, 3, 16 | AW537799 | | *Mus musculus* SIK similar protein mRNA, complete cds | 2.636695362 |
| 5, 4, 12 | AU019331 | | ESTs | 2.092198567 |
| 5, 6, 24 | AA016759 | Mcmd6 | mini chromosome maintenance deficient 6 (*S. cerevisiae*) | 3.942228729 |
| 5, 8, 26 | AA547555 | Cks1 | CDC28 protein kinase 1 | 2.842163855 |
| 6, 1, 18 | AA475488 | | ESTs, Highly similar to KIAA1008 protein [*H. sapiens*] | 1.907792508 |
| 6, 10, 11 | AU016865 | Zpk | zipper (leucine) protein kinase | 1.87496068 |
| 6, 11, 6 | AW556065 | | | 5.780334277 |
| 6, 12, 6 | AW556081 | | ESTs | 2.22898364 |
| 6, 15, 13 | AU023995 | | *Mus musculus* chromosome segregation protein SmcB (SmcB) mRNA, complete cds | 2.530486227 |
| 6, 17, 18 | AW541455 | | ESTs, Weakly similar to anillin [*D. melanogaster*] | 1.752249825 |
| 6, 17, 9 | AW546860 | | ESTs | 2.576070438 |
| 6, 19, 18 | AW541501 | | ESTs, Highly similar to CLATHRIN HEAVY CHAIN [*Rattus norvegicus*] | 2.117485424 |
| 6, 19, 8 | AW552139 | Adcy6 | adenylate cyclase 6 | 3.731201924 |
| 6, 22, 10 | AU041439 | Gnai2 | guanine nucleotide binding protein, alpha inhibiting 2 | 2.87168005 |
| 6, 22, 9 | AW548297 | Gtse1 | G two S phase expressed protein 1 | 1.95946572 |
| 6, 3, 5 | AW557901 | | ESTs, Weakly similar to C54G7.4 gene product [*C. elegans*] | 2.522377919 |
| 6, 5, 8 | AW549706 | Nedd4 | neural precursor cell expressed, developmentally down-regulated gene 4 | 2.327084972 |
| 6, 6, 7 | AW553142 | | | 2.086689668 |
| 6, 6, 8 | AW549721 | Hspa9a | heat shock protein, 74 kDa, A | 2.535480124 |
| 6, 7, 8 | AW549786 | Atp5b | ATP synthase, H+ transporting mitochondrial F1 complex, alpha subunit | 3.883486547 |
| 6, 8, 8 | AW549817 | Blr1 | Burkitt lymphoma receptor 1 | 1.904634735 |
| 6, 9, 10 | AU044286 | | ESTs | 2.426995221 |
| 7, 1, 11 | AU016189 | | ESTs | 2.013455426 |
| 7, 1, 6 | AW555561 | Mybl2 | myeloblastosis oncogene-like 2 | 2.467492726 |
| 7, 10, 7 | AW553629 | | ESTs, Moderately similar to LEYDIG CELL TUMOR 10 KD PROTEIN [*Rattus norvegicus*] | 1.78861896 |
| 7, 12, 7 | AW554486 | Unp | ubiquitous nuclear protein | 1.967446342 |
| 7, 16, 8 | AW551867 | Csrp2 | cysteine-rich protein 2 | 1.642967264 |
| 7, 16, 9 | AW547491 | | ESTs, Highly similar to nuclear pore complex glycoprotein p62 [*M. musculus*] | 1.751627931 |
| 7, 20, 17 | AW536943 | | ESTs | 5.965587283 |
| 7, 23, 25 | AA003258 | | ESTs | 3.034150589 |
| 7, 3, 11 | AU016261 | | ESTs | 2.130579346 |

SUPPLEMENTAL TABLE 1-continued

| ID | Acc No | Gene | Description | N/F ratio |
|---|---|---|---|---|
| 7, 6, 16 | AW537692 | | ESTs, Highly similar to AUXIN-RESISTANCE PROTEIN AXR1 [*Arabidopsis thaliana*] | 4.828573083 |
| 7, 6, 26 | AA437614 | | ESTs, Highly similar to S1-1 protein [*R. norvegicus*] | 2.580768885 |
| 7, 7, 16 | AW537731 | | ESTs | 3.026122202 |
| 7, 8, 10 | AU043672 | | ESTs, Highly similar to PUTATIVE ATP-DEPENDENT RNA HELICASE C22F3.08C [*Schizosaccaromyces pombe*] | 2.123346276 |
| 7, 8, 12 | AU020664 | | *Mus musculus* dUB-type TGT mRNA for deubiquitinating enzyme, complete cds | 3.722164894 |
| 7, 8, 22 | AA168656 | D5Ertd363e | DNA segment, Chr 5, ERATO Doi 363, expressed | 3.199043745 |
| 7, 9, 10 | AU045064 | | ESTs, Highly similar to SOH1 PROTEIN [*Saccharomyces cerevisiae*] | 2.035291187 |
| 8, 1, 20 | AA241756 | sid2057p | small acidic protein sid2057p | 3.155791289 |
| 8, 10, 7 | AW553223 | | ESTs | 2.428431066 |
| 8, 12, 17 | AW545455 | | ESTs | 2.121493764 |
| 8, 12, 5 | AI573460 | Chd1 | Chromodomain helicase DNA binding protein 1 | 2.550880804 |
| 8, 14, 8 | AW551176 | | | 3.984110864 |
| 8, 16, 18 | AW538820 | Ak4 | adenylate kinase 4 | 5.590412241 |
| 8, 2, 5 | AW557865 | Rad50 | RAD50 homolog (*S. cerevisiae*) | 2.71088834 |
| 8, 21, 11 | AU018118 | Nap1l1 | nucleosome assembly protein 1-like 1 | 4.577669891 |
| 8, 21, 7 | AW555020 | | ESTs, Highly similar to UBIQUINOL-CYTOCHROME C REDUCTASE COMPLEX CORE PROTEIN 2 PRECURSOR [*Bos taurus*] | 3.13400887 |
| 8, 22, 18 | AW542335 | | ESTs, Highly similar to MICROSOMAL SIGNAL PEPTIDASE 21 KD SUBUNIT [*Canis familiaris*] | 2.436734688 |
| 8, 23, 3 | AI452358 | | ESTs | 2.785539438 |
| 8, 5, 26 | AA474386 | | ESTs | 3.472579152 |
| 8, 6, 17 | AW544320 | | ESTs, Highly similar to G10 PROTEIN [*Xenopus laevis*] | 3.666082859 |
| 8, 6, 6 | AW555813 | | ESTs | 2.358368809 |
| 8, 8, 24 | AA014445 | Fl10 | FL10 | 3.940466825 |
| 8, 9, 6 | AW555985 | Rpa2 | replication protein A2 | 2.490514775 |
| 9, 1, 15 | C78280 | | | 2.916669069 |
| 9, 1, 5 | AW558079 | | ESTs, Weakly similar to PPAR gamma coactivator [*M. musculus*] | 2.596900062 |
| 9, 11, 16 | C76867 | | ESTs, Moderately similar to TROPOMYOSIN ALPHA CHAIN, SKELETAL AND CARDIAC MUSCLE [*M. musculus*] | 2.862563996 |
| 9, 12, 11 | AU017259 | eed | embryonic ectoderm development | 3.343130988 |
| 9, 13, 11 | AU017276 | Ntan1 | N-terminal Asn amidase | 2.571512897 |
| 9, 13, 7 | AW554273 | | ESTs, Weakly similar to VRK2 [*H. sapiens*] | 1.647320818 |
| 9, 14, 23 | AA086829 | Mssk1 | muscle-specific serine kinase 1 | 2.100087115 |
| 9, 16, 11 | AU018261 | | ESTs | 4.232824804 |
| 9, 17, 11 | AU040108 | | | 2.163537648 |
| 9, 17, 8 | AW551726 | Wbp5 | WW domain binding protein 5 | 2.496644567 |
| 9, 2, 6 | AW555464 | | ESTs, Weakly similar to neuronal-specific septin 3 [*M. musculus*] | 2.857649535 |
| 9, 20, 17 | AW536798 | | ESTs | 2.045207463 |
| 9, 21, 10 | AU041740 | | *M. musculus* mRNA for fibromodulin | 2.01868023 |
| 9, 22, 10 | AU041756 | | ESTs | 2.554725916 |
| 9, 22, 8 | AW552312 | | | 1.97837746 |
| 9, 3, 9 | AU042878 | Psmc3ip | proteasome (prosome, macropain) 26S subunit, ATPase 3, interacting protein | 2.069863024 |
| 9, 4, 16 | AW537568 | | ESTs, Weakly similar to similar to yeast heat shock protein STI1 [*C. elegans*] | 2.212010488 |
| 9, 5, 25 | W82194 | LOC57423 | hypothetical protein, clone: 2-31 | 3.004332364 |
| 9, 6, 22 | AA144221 | Hic53 | hydrogen peroxide inducible protein 53 | 1.613906386 |
| 9, 7, 17 | AW544666 | | ESTs | 1.573680622 |
| 24, 13, 17 | AW545557 | | | 0.289781915 |
| 11, 23, 13 | AU018762 | gMCK2 | *Mus musculus* casein kinase 2 beta subunit | 0.213188567 |
| 37, 21, 16 | C78503 | Ask-pending | activator of S phase kinase | 0.193218524 |
| 2, 18, 12 | AU021170 | Abca1 | Macrophage specific gene | 0.390186712 |
| 8, 10, 15 | C79113 | | weakly similar to casein kinase 2 beta subunit | 0.195588578 |
| 38, 15, 18 | AW538851 | | ESTs | 0.18013489 |
| 39, 5, 15 | C79508 | | ESTs | 0.288885071 |
| 37, 7, 13 | AU023540 | | | 0.167735354 |
| 12, 10, 7 | AW552972 | | ESTs, Highly similar to ATP-DEPENDENT PROTEASE LA 2 [*Myxococcus xanthus*] | 0.297372968 |
| 11, 2, 12 | AU018863 | Klf4 | Kruppel-like factor 4 (gut) | 0.403065274 |
| 24, 17, 15 | C80212 | | ESTs | 0.338126518 |
| 17, 20, 15 | C85300 | unp | *Mus musculus* ubiquitin-specific protease | 0.323004358 |
| 43, 13, 2 | AI451378 | | ESTs | 0.454721961 |
| 31, 7, 13 | AU023508 | | *Mus musculus* uroporphyrinogen III synthase gene, promoter, | 0.168448583 |
| 24, 22, 13 | AU018397 | Nek7 | *Mus musculus* NIMA (never in mitosis gene a)-related expressed kinase 7 | 0.359839285 |

SUPPLEMENTAL TABLE 2

Primers used in Quantitative RT-PCR (QRT-PCR).

| Gene Name | Primer type | Primer sequence 5'-3' | Annealing Temperature (° C.) | Product Size (bp) |
|---|---|---|---|---|
| Apoptosis Inhibitor 4 | Forward | accttcaagaactggccctt | 60 | 117 |
| | Reverse | aaaacactgggccaaatcag | | |
| Breast Cancer Associated Protein 2 | Forward | ttggacaaccccaattaaa | 60 | 100 |
| | Reverse | ctggagtgcттттгgaaggc | | |
| Defender Against Death 1 | Forward | ttgctggatgcctatctcct | 60 | 147 |
| | Reverse | gcaaaccgctaagatgaagc | | |
| Heat Shock Protein 60 | Forward | acacaaatgaagaggctggg | 60 | 106 |
| | Reverse | actggattagcccctttgct | | |
| Integrin Beta 1 | Forward | cagtgaacagcaagggtgaa | 60 | 115 |
| | Reverse | taagaacaattccggcaacc | | |
| Macrophage Migration Inhibitory Factor 1 | Forward | ttcatcgtgaacaccaatgt | 60 | 147 |
| | Reverse | aaaagtcatgagctggtccg | | |
| Ornithine Decarboxy-lase 1 | Forward | catccaaaggcaaagttggt | 60 | 104 |
| | Reverse | agcctgctggttttcagtgt | | |
| Beta-actin | Forward | gatctggcaccacaccttct | 60 | 144 |
| | Reverse | ggggtgttgaaggtctcaaa | | |
| GAPDH | Forward | gaagggctcatgaccacagt | 60 | 125 |
| | Reverse | ggatgcagggatgatgttct | | |

SUPPLEMENTAL TABLE 3

Primers used in Quantitative Real Time PCR (QRT-PCR).

| Primer name | | Sequence 5'-3' | Product size (bp) | Annealing temperature (° C.) |
|---|---|---|---|---|
| ZBP1 | Forward | tcaagattgctccaccagaa | 91 | 60 |
| | Reverse | cttccctgagccttgaactg | | |
| Arp2/3, p21 | Forward | ttcaaggccaacgtcttctt | 120 | 60 |
| | Reverse | tctggagттgcaстттгgga | | |
| Actin gamma | Forward | actgggacgacatggagaag | 114 | 60 |
| | Reverse | tgttagctttggggttcagg | | |
| LIMK 1 | Forward | tcatcaagagcatggacagc | 113 | 60 |
| | Reverse | gaggtctcggtggatgatgt | | |
| Actn3 | Forward | gcaggagcagaacatcatca | 112 | 60 |
| | Reverse | catgctgtagaccgtgtgct | | |
| CFL1 | Forward | gtcaagatgctgccagacaa | 102 | 60 |
| | Reverse | ggcccagaaaatgaatacca | | |
| TMOD | Forward | cgagggttaaaggggaaaag | 102 | 60 |
| | Reverse | gacaggcatcgttctcccta | | |
| MNS1 | Forward | ctgccgatctctcatcctct | 100 | 60 |
| | Reverse | gagcacaagccactctgaca | | |
| Cap 1 | Forward | gaaagccaccagtttcaacc | 105 | 60 |
| | Reverse | cttgagcactccaaccacct | | |
| Rock 1 | Forward | ttcaagccgactaacggtatg | 114 | 60 |
| | Reverse | gctcgaggaattctggaaga | | |

SUPPLEMENTAL TABLE 3-continued

Primers used in Quantitative Real Time PCR (QRT-PCR).

| Primer name | | Sequence 5'-3' | Product size (bp) | Annealing temperature (° C.) |
|---|---|---|---|---|
| Arp2/3, p16 | Forward Reverse | gctaggctcgctgaagaaga tattcgtccacgtccacctt | 117 | 60 |
| Beta-actin | Forward Reverse | gatctggcaccacaccttct ggggtgttgaaggtctcaaa | 144 | 60 |
| GAPDH | Forward Reverse | gaagggctcatgaccacagt ggatgcagggatgatgttct | 125 | 60 |

SUPPLEMENTAL TABLE 4

| Acc No | Gene | Description | N/F ratio |
|---|---|---|---|
| AW536875 | | ESTs, Highly similar to 60S RIBOSOMAL PROTEIN L15 [*Rattus norvegicus*] | 28.07042798 |
| C88094 | | ESTs, Weakly similar to teg292 protein [*M. musculus*] | 14.31878982 |
| AI894273 | | ESTs, Moderately similar to HIGH MOBILITY GROUP-LIKE NUCLEAR PROTEIN 2 [*Saccharomyces cerevisiae*] | 13.46949084 |
| AW555456 | | *Mus musculus* centrin (Cetn2) gene, complete cds | 12.38855512 |
| AW548322 | Pctk1 | PCTAIRE-motif protein kinase 1 | 12.057525 |
| C86468 | Kcnn4 | potassium intermediate/small conductance calcium-activated channel, subfamily N, member 4 | 11.02530152 |
| AU019118 | | ESTs, Moderately similar to unknown [*H. sapiens*] | 9.327888895 |
| AA041834 | Tk1 | Thymidine kinase 1 | 8.480042707 |
| AW536197 | | *Mus musculus* Tera (Tera) mRNA, complete cds | 8.192347763 |
| AW557657 | Idh1 | isocitrate dehydrogenase 1 (NADP+), soluble | 8.106563202 |
| AW537075 | | ESTs, Weakly similar to SIG41 [*M. musculus*] | 7.942965646 |
| AA172774 | D16Wsu83e | DNA segment, Chr 16, Wayne State University 83, expressed | 7.71686883 |
| AW543722 | | ESTs, Highly similar to ARGINYL-TRNA SYNTHETASE [*Cricetulus longicaudatus*] | 7.643773902 |
| AA209964 | D11Moh34 | DNA segment, Chr 11, KL Mohlke 34 | 7.590178566 |
| AU041246 | | ESTs, Highly similar to 26S PROTEASE REGULATORY SUBUNIT 4 HOMOLOG [*Schizosaccaromyces pombe*] | 7.575991278 |
| AW536755 | | ESTs, Highly similar to similar to nuclear domain 10 protein NDP52 [*H. sapiens*] | 7.509323804 |
| AU019152 | Zfr | zinc finger RNA binding protein | 7.187804716 |
| AW554270 | Hnrpu | heterogeneous nuclear ribonucleoprotein U | 6.962446985 |
| AU024490 | | ESTs, Highly similar to PROTEIN TRANSLATION FACTOR SUI1 HOMOLOG [*Anopheles gambiae*] | 6.646581144 |
| AU018130 | | ESTs, Weakly similar to cholesterol 25-hydroxylase [*M. musculus*] | 6.335735765 |
| AW539791 | | ESTs, Weakly similar to coded for by *C. elegans* cDNAs GenBank: [*C. elegans*] | 6.21796016 |
| AU017180 | | ESTs, Highly similar to HETEROGENEOUS NUCLEAR RIBONUCLEOPROTEIN K [*Homo sapiens*; *Rattus norvegicus*] | 6.088798225 |
| AI464376 | | *M. musculus* mRNA for ribosomal protein S5 | 6.087358987 |
| AW544204 | Cct8 | chaperonin subunit 8 (theta) | 6.014885062 |
| AW546174 | Tgfb1i4 | transforming growth factor beta 1 induced transcript 4 | 5.668988417 |
| AA068436 | | ESTs, Highly similar to unknown [*R. norvegicus*] | 5.647684222 |
| AW538820 | Ak4 | adenylate kinase 4 | 5.590412241 |
| AW549255 | | ESTs, Weakly similar to unknown [*R. norvegicus*] | 5.576813364 |
| AU041887 | | ESTs, Highly similar to HYPOTHETICAL 30.3 KD PROTEIN IN APE1/LAP4-CWP1 INTERGENIC REGION [*Saccharomyces cerevisiae*] | 5.573324729 |
| AW547924 | Rbbp7 | retinoblastoma binding protein 7 | 5.560647246 |
| AU018928 | | ESTs, Highly similar to TRAF4-associated factor 2 [*H. sapiens*] | 5.510048965 |
| W62229 | Ube1c | ubiquitin-activating enzyme E1C | 5.477163155 |
| AW537279 | Macs | myristoylated alanine rich protein kinase C substrate | 5.47595949 |
| C78877 | Psmc5 | protease (prosome, macropain) 26S subunit, ATPase 5 | 5.462141323 |
| AW548086 | Ptma | prothymosin alpha | 5.460385354 |
| AU023751 | | ESTs, Highly similar to HPBRII-7 protein [*H. sapiens*] | 5.426224824 |
| C78481 | Eif3 | eukaryotic translation initiation factor 3 | 5.424426041 |
| AW545033 | | ESTs, Moderately similar to KIAA0007 [*H. sapiens*] | 5.424290287 |
| AU041313 | Etl1 | enhancer trap locus 1 | 5.38413569 |
| AU015358 | Ubl1a2-pending | ubiquitin-like 1 (sentrin) activating enzyme subunit 2 | 5.365114455 |
| AW543409 | DXWsu72e | DNA segment, Chr X, Wayne State University 72, expressed | 5.350172937 |
| AA030995 | Ppib | peptidylprolyl isomerase B | 5.335704428 |
| AW549121 | Hmg14 | high mobility group protein 14 | 5.305166988 |
| AW553645 | Slc12a2 | solute carrier family 12, member 2 | 5.209225843 |
| AW536460 | Sfrs3 | splicing factor, arginine/serine-rich 3 (SRp20) | 5.140661094 |
| W59202 | Stat3ip1-pending | signal transducer and activator of transcription 3 interacting protein 1 | 5.10228177 |
| AW542927 | Bcap31 | B-cell receptor-associated protein 31 | 5.066787673 |
| AW536194 | | ESTs, Highly similar to CGI-35 protein [*H. sapiens*] | 5.045862039 |
| AW538480 | | ESTs, Moderately similar to serine proteinase inhibitor 6 [*M. musculus*] | 4.92457718 |

SUPPLEMENTAL TABLE 4-continued

| Acc No | Gene | Description | N/F ratio |
|---|---|---|---|
| AW539467 | Eif3 | eukaryotic translation initiation factor 3 | 4.892017699 |
| AW544515 | Arl6ip | ADP-ribosylation-like factor 6 interacting protein | 4.837717593 |
| AW537692 | | ESTs, Highly similar to AUXIN-RESISTANCE PROTEIN AXR1 [*Arabidopsis thaliana*] | 4.828573083 |
| AW552431 | Scp2 | sterol carrier protein 2, liver | 4.818202195 |
| AW536911 | Cd97 | CD97 antigen | 4.810474487 |
| AW536359 | | ESTs, Highly similar to UNR PROTEIN [*Rattus norvegicus*] | 4.798453644 |
| AW544502 | Atp1b1 | ATPase, Na+/K+ transporting, beta 1 polypeptide | 4.787962787 |
| AW545835 | | *Mus musculus* Smt3A protein mRNA, complete cds | 4.7826417 |
| AW538992 | | *Mus musculus* mRNA for 26S proteasome non-ATPase subunit | 4.76789816 |
| AW545393 | | ESTs, Highly similar to TRANSLATION INITIATION FACTOR EIF-2B GAMMA SUBUNIT [*R. norvegicus*] | 4.68467069 |
| AW544140 | D10Wsu52e | DNA segment, Chr 10, Wayne State University 52, expressed | 4.683018189 |
| AI327096 | | *Mus musculus* neuronal calcium sensor-1 (NCS-1) mRNA, complete cds | 4.676318103 |
| AW541474 | Ncl | nucleolin | 4.657700504 |
| AW537584 | Krt2-8 | keratin complex 2, basic, gene 8 | 4.6321245 |
| AW557019 | | ESTs, Moderately similar to TRANSCRIPTION INITIATION FACTOR IIA SMALL CHAIN [*Saccharomyces cerevisiae*] | 4.63152 |
| AW538715 | Ass1 | arginosuccinate synthetase 1 | 4.609205297 |
| AW544376 | | ESTs, Weakly similar to predicted using Genefinder [*C. elegans*] | 4.596454455 |
| C76750 | Hnrpa1 | heterogeneous nuclear ribonucleoprotein A1 | 4.582363217 |
| AU018118 | Nap1l1 | nucleosome assembly protein 1-like 1 | 4.577669891 |
| AA166336 | | ESTs, Moderately similar to DRIM protein [*H. sapiens*] | 4.515841853 |
| C79184 | Kpna2 | karyopherin (importin) alpha 2 | 4.483193007 |
| AW538863 | | *Mus musculus* mRNA for mitochondrial acyl-CoA thioesterase, clone 1 | 4.480301436 |
| AW547148 | | ESTs, Highly similar to LL5 protein [*R. norvegicus*] | 4.473954317 |
| AW536137 | Cct5 | chaperonin subunit 5 (epsilon) | 4.469320692 |
| AU044379 | Arl6ip | ADP-ribosylation-like factor 6 interacting protein | 4.456690776 |
| AA272363 | | ESTs, Highly similar to KINESIN-II 85 KD SUBUNIT [*Strongylocentrotus purpuratus*] | 4.451371032 |
| AW537358 | | ESTs, Weakly similar to cDNA EST yk338g10.5 comes from this gene [*C. elegans*] | 4.424107656 |
| AU040277 | Rpms7 | ribosomal protein, mitochondrial, S7 | 4.42173964 |
| AU015699 | | ESTs, Highly similar to SPLICING FACTOR U2AF 35 KD SUBUNIT [*Homo sapiens*] | 4.396787304 |
| AU043252 | | *Mus musculus* succinyl-CoA synthetase (Sucla1) mRNA, complete cds | 4.389745409 |
| AU043400 | Supt4h | suppressor of Ty 4 homolog (*S. cerevisiae*) | 4.346211791 |
| AA414612 | Cappa1 | capping protein alpha 1 | 4.335956318 |
| AW558053 | Ugt1a1 | UDP-glucuronosyltransferase 1 family, member 1 | 4.324788648 |
| AW539780 | H3f3b | H3 histone, family 3B | 4.312364694 |
| AW545006 | Psmb1 | proteasome (prosome, macropain) subunit, beta type 1 | 4.277781412 |
| AW555779 | Mapk3 | mitogen activated protein kinase 3 | 4.26598905 |
| AW552398 | | ESTs, Moderately similar to TRANSCRIPTION INITIATION FACTOR TFIID 28 KD SUBUNIT [*H. sapiens*] | 4.263787523 |
| AW537694 | | ESTs, Highly similar to HYPOTHETICAL 109.5 KD PROTEIN IN PPA1-DAP2 INTERGENIC REGION [*Saccharomyces cerevisiae*] | 4.238918085 |
| C80485 | Zfr | zinc finger RNA binding protein | 4.204981315 |
| AW539102 | | ESTs, Weakly similar to EUKARYOTIC TRANSLATION INITIATION FACTOR 3 BETA SUBUNIT [*H. sapiens*] | 4.200882302 |
| W75853 | | ESTs, Moderately similar to SIGNAL RECOGNITION PARTICLE 19 KD PROTEIN [*Homo sapiens*] | 4.198748472 |
| AW542909 | Hmg14 | high mobility group protein 14 | 4.195667397 |
| AA162800 | Cul3 | cullin 3 | 4.189740174 |
| AW554926 | | ESTs, Highly similar to PTB-ASSOCIATED SPLICING FACTOR [*Homo sapiens*] | 4.181277703 |
| AW545839 | Nap1l1 | nucleosome assembly protein 1-like 1 | 4.179882367 |
| AU023746 | Tacc3 | transforming, acidic coiled-coil containing protein 3 | 4.176773893 |
| AA422809 | | ESTs, Highly similar to KIAA0368 [*H. sapiens*] | 4.173186503 |
| AW537017 | Odc | ornithine decarboxylase, structural | 4.144399442 |
| AW553526 | Npm1 | nucleophosmin 1 | 4.140352223 |
| AW538686 | Ubce7 | ubiquitin-conjugating enzyme 7 | 4.138451568 |
| AU021740 | | ESTs, Weakly similar to POSSIBLE GLOBAL TRANSCRIPTION ACTIVATOR SNF2L [*Caenorhabditis elegans*] | 4.128979953 |
| AW537566 | | ESTs, Highly similar to HYPOTHETICAL PROTEIN C22G7.01C IN CHROMOSOME I [*Schizosaccaromyces pombe*] | 4.125279614 |
| AW548258 | P4ha1 | procollagen-proline, 2-oxoglutarate 4-dioxygenase (proline 4-hydroxylase), alpha 1 polypeptide | 4.107549035 |
| AU040830 | | ESTs, Weakly similar to 60S RIBOSOMAL PROTEIN L30A [*Saccharomyces cerevisiae*] | 4.091843934 |
| AA033344 | Slc12a2 | solute carrier family 12, member 2 | 4.088397442 |
| AU019262 | | ESTs, Weakly similar to DNAJ PROTEIN HOMOLOG MTJ1 [*M. musculus*] | 4.084659729 |
| AA465980 | | ESTs, Highly similar to HYPOTHETICAL 51.6 KD PROTEIN F59B2.5 IN CHROMOSOME [*Caenorhabditis elegans*] | 4.083961131 |
| AW549711 | | *Mus musculus* fallotein mRNA, complete cds | 4.0677901 |
| C80966 | Timm8b | translocase of inner mitochondrial membrane 8 homolog b (yeast) | 4.044729993 |
| AW556206 | Hsp84-1 | heat shock protein, 84 kDa 1 | 4.022387626 |
| AU043443 | | ESTs, Highly similar to TRAM PROTEIN [*Canis familiaris*] | 4.011298228 |
| AW545939 | Rps12 | ribosomal protein S12 | 4.009116425 |
| AW548431 | | ESTs, Highly similar to CYTOCHROME C OXIDASE POLYPEPTIDE VIIB PRECURSOR [*Homo sapiens*] | 4.009096262 |
| AI426498 | | *Mus musculus* radio-resistance/chemo-resistance/cell cycle checkpoint control protein (Rad9) mRNA, complete cds | 4.007328711 |
| AI429136 | | ESTs, Highly similar to transforming acidic coiled-coil containing protein 3 [*M. musculus*] | 4.00493038 |

SUPPLEMENTAL TABLE 4-continued

| Acc No | Gene | Description | N/F ratio |
|---|---|---|---|
| AU020233 | Arf1 | ADP-ribosylation factor 1 | 3.991526009 |
| AU041628 | | ESTs, Weakly similar to ORF2 [*M. musculus*] | 3.98385943 |
| AU018486 | Ssb | Sjogren syndrome antigen B | 3.979536441 |
| AW536140 | Hsp86-1 | heat shock protein, 86 kDa 1 | 3.972152303 |
| AI323926 | Fau | Finkel-Biskis-Reilly murine sarcoma virus (FBR-MuSV) ubiquitously expressed (fox derived) | 3.970764464 |
| C86592 | Fn1 | fibronectin 1 | 3.964340966 |
| AW556230 | Cdc42 | cell division cycle 42 homolog (*S. cerevisiae*) | 3.958094748 |
| AI324227 | | *Mus musculus* 14-3-3 protein gamma mRNA, complete cds | 3.946899417 |
| AA016759 | Mcmd6 | mini chromosome maintenance deficient 6 (*S. cerevisiae*) | 3.942228729 |
| AA014445 | Fl10 | FL10 | 3.940466825 |
| C78998 | Rpl27 | ribosomal protein L27 | 3.935127734 |
| AA008189 | | ESTs, Highly similar to KINESIN-II 85 KD SUBUNIT [*Strongylocentrotus purpuratus*] | 3.921010056 |
| AW554328 | | ESTs, Highly similar to RSP5 PROTEIN [*Saccharomyces cerevisiae*] | 3.913617092 |
| AU042788 | | ESTs, Moderately similar to phosphoenolpyruvate carboxykinase [*M. musculus*] | 3.912511036 |
| AW539228 | Fasl | Faa antigen ligand | 3.910933775 |
| AW556588 | Tpi | triosephosphate isomerase | 3.903538184 |
| AU045251 | Ranbp1 | RAN binding protein 1 | 3.903340068 |
| AW539811 | Cdc10 | cell division cycle 10 homolog (*S. cerevisiae*) | 3.902125311 |
| AW555157 | | ESTs, Highly similar to C-1-TETRAHYDROFOLATE SYNTHASE, CYTOPLASMIC [*Homo sapiens*] | 3.896907728 |
| AU015486 | Cappa2 | capping protein alpha 2 | 3.894401118 |
| C87887 | Etl1 | enhancer trap locus 1 | 3.89073106 |
| AW542408 | Pea15 | phosphoprotein enriched in astrocytes 15 | 3.887421434 |
| AW549786 | Atp5b | ATP synthase, H+ transporting mitochondrial F1 complex, alpha subunit | 3.883486547 |
| AW537480 | Atp5a1 | ATP synthase, H+ transporting, mitochondrial F1 complex, alpha subunit, isoform 1 | 3.879801077 |
| AW555675 | | ESTs, Highly similar to ALCOHOL DEHYDROGENASE [*Homo sapiens*] | 3.873714959 |
| AA423312 | Ga17-pending | dendritic cell protein GA17 | 3.848176993 |
| AW544122 | Nap1l1 | nucleosome assembly protein 1-like 1 | 3.846161333 |
| AW548354 | | *Mus musculus* elongation factor 1-beta homolog mRNA, complete cds | 3.799007315 |
| C79212 | | ESTs, Weakly similar to R32611_2 [*H. sapiens*] | 3.7976083 |
| AW558177 | | ESTs, Weakly similar to head-elevated expression in 0.9 kb [*D. melanogaster*] | 3.796955936 |
| AW556707 | | ESTs, Moderately similar to PTB-ASSOCIATED SPLICING FACTOR [*Homo sapiens*] | 3.794530279 |
| AW557574 | Lrpap1 | low density lipoprotein receptor related protein, associated protein 1 | 3.789636371 |
| AA545607 | Mtf2 | metal response element binding transcription factor 2 | 3.777112474 |
| AW545354 | | *Mus musculus* mRNA for sid2057p, complete cds | 3.771481148 |
| AW553405 | Ube1x | ubiquitin-activating enzyme E1, Chr X | 3.743347278 |
| AW543524 | Ghrh | growth hormone releasing hormone | 3.731298401 |
| AU020664 | | *Mus musculus* dUB-type TGT mRNA for deubiquitinating enzyme, complete cds | 3.722164894 |
| C76678 | | *Mus musculus* mRNA for Sid6061p, complete cds | 3.720028548 |
| AW546455 | | ESTs, Moderately similar to nuclear factor of activated T-cells, cytoplasmic 3 [*H. sapiens*] | 3.70859768 |
| C87205 | | ESTs, Weakly similar to C44B9.1 [*C. elegans*] | 3.701990317 |
| AU021072 | | ESTs, Weakly similar to unknown [*R. norvegicus*] | 3.691199965 |
| AA073695 | Mea1 | male enhanced antigen 1 | 3.681248673 |
| C87164 | Ier3 | immediate early response 3 | 3.675300717 |
| AW547244 | Rpl10a | ribosomal protein L10A | 3.671627312 |
| C79581 | Msn | moesin | 3.670385369 |
| AW546184 | Atp6d | ATPase, H+ transporting, lysosomal (vacuolar proton pump), 42 kDa | 3.669772578 |
| AW544320 | | ESTs, Highly similar to G10 PROTEIN [*Xenopus laevis*] | 3.666082859 |
| C88028 | | ESTs, Highly similar to small membrane protein 1 [*H. sapiens*] | 3.66566524 |
| AW553254 | Zfp207 | zinc finger protein 207 | 3.651732585 |
| AW539757 | Zfp36 | zinc finger protein 36 | 3.649425165 |
| AU020890 | | ESTs, Weakly similar to CARG-BINDING FACTOR-A [*Mus musculus*] | 3.645112149 |
| AW543415 | | *Mus musculus* secretory carrier membrane protein 4 mRNA, complete cds | 3.643663528 |
| C87445 | | ESTs, Highly similar to PROBABLE 3-OXOADIPATE COA-TRANSFERASE SUBUNIT B [*Bacillus subtilis*] | 3.635344195 |
| AW554947 | | ESTs, Highly similar to translation initiation factor IF2 [*H. sapiens*] | 3.625644265 |
| AW545835 | | *Mus musculus* Smt3A protein mRNA, complete cds | 3.606723188 |
| AW554157 | Nsmaf | neutral sphingomyelinase (N-SMase) activation associated factor | 3.602107632 |
| C77976 | | ESTs, Weakly similar to retinoblastoma-associated protein HEC [*H. sapiens*] | 3.599674605 |
| AW543839 | | ESTs, Moderately similar to AKAP450 protein [*H. sapiens*] | 3.596313894 |
| AA015136 | LOC56046 | hypothetical protein | 3.596271768 |
| AI324640 | Amd3 | S-adenosylmethionine decarboxylase 3 | 3.595274519 |
| AW541494 | Surf4 | surfeit gene 4 | 3.591874393 |
| AI450158 | | SIGNAL RECOGNITION PARTICLE 54 KD PROTEIN | 3.578261456 |
| AW557661 | Taldo1 | transaldolase 1 | 3.573769539 |
| AA537161 | | ESTs, Highly similar to A55058 retinoic acid-regulated protein pH 34 - mouse [*M. musculus*] | 3.573741952 |
| AU043213 | Ewsh | Ewing sarcoma homolog | 3.565251777 |
| AU021819 | Top1 | topoisomerase (DNA) I | 3.548400292 |
| AW537207 | | ESTs, Highly similar to transcription factor NF-AT 45K chain [*H. sapiens*] | 3.53722457 |
| C86331 | H3f3b | H3 histone, family 3B | 3.533490685 |
| AW552131 | | ESTs, Highly similar to HYPOTHETICAL 109.5 KD PROTEIN IN PPA1-DAP2 INTERGENIC REGION [*Saccharomyces cerevisiae*] | 3.530658429 |
| AU018409 | ArhA | Rho family GTPase | 3.530268774 |
| AI323675 | Pctk3 | PCTAIRE-motif protein kinase 3 | 3.521685781 |

SUPPLEMENTAL TABLE 4-continued

| Acc No | Gene | Description | N/F ratio |
|---|---|---|---|
| AW536904 | Ppia | peptidylprolyl isomerase A | 3.507621504 |
| AI327246 | | ESTs, Weakly similar to titin [M. musculus] | 3.507243434 |
| AW544281 | | Mus musculus ASC-1 mRNA, complete cds | 3.50215121 |
| AW551918 | Ube2i | ubiquitin-conjugating enzyme E2I | 3.500959948 |
| W48168 | Hprt | Hypoxanthine guanine phosphoribosyl transferase | 3.495738168 |
| AU016813 | | ESTs, Highly similar to ubiquitin specific protease [H. sapiens] | 3.494717718 |
| AA396298 | | Mus musculus mRNA for RNase 4, complete cds | 3.470957341 |
| AW539445 | Homer2-pending | homer, neuronal immediate early gene, 2 | 3.468546701 |
| AW536666 | Hmg1 | high mobility group protein 1 | 3.462175648 |
| AW549114 | Dncic2 | dynein, cytoplasmic, intermediate chain 2 | 3.461903637 |
| AW544801 | Nap1l1 | nucleosome assembly protein 1-like 1 | 3.457665096 |
| AW543791 | Tbrg1 | transforming growth factor beta regulated gene 1 | 3.456539482 |
| AW538438 | Rpl27a | ribosomal protein L27a | 3.451778704 |
| AU016022 | Anxa4 | annexin A4 | 3.448280131 |
| C79628 | Psme1 | protease (prosome, macropain) 28 subunit, alpha | 3.442541693 |
| AA066250 | | ESTs, Weakly similar to BC-2 protein [H. sapiens] | 3.430116366 |
| AW542410 | Psmc5 | protease (prosome, macropain) 26S subunit, ATPase 5 | 3.429494424 |
| AU018029 | | ESTs, Highly similar to cbp146 [M. musculus] | 3.428043044 |
| C85115 | | ESTs, Highly similar to NADH-CYTOCHROME B5 REDUCTASE [Rattus norvegicus] | 3.427306351 |
| AW556395 | Oaz1 | ornithine decarboxylase antizyme | 3.418302938 |
| AW536137 | Cct5 | chaperonin subunit 5 (epsilon) | 3.417978956 |
| AA517043 | Rnf4 | ring finger protein 4 | 3.409788494 |
| AW551969 | Prtb | proline rich protein expressed in brain | 3.399624829 |
| AU016270 | | ESTs, Highly similar to CYCLIN-DEPENDENT KINASES REGULATORY SUBUNIT 2 [Homo sapiens] | 3.395812648 |
| AW549909 | Surf4 | surfeit gene 4 | 3.393471399 |
| AU044024 | Tjp2 | tight junction protein 2 | 3.392383317 |
| AW546168 | Rps5 | ribosomal protein S5 | 3.391993373 |
| AW538671 | Col5a3 | procollagen, type V, alpha 3 | 3.383446584 |
| AI894263 | Tuba2 | Tubulin alpha 2 | 3.37781933 |
| AW543832 | | ESTs, Highly similar to eukaryotic translation initiation factor elF3, p35 subunit [H. sapiens] | 3.374834929 |
| AW536945 | | ESTs, Weakly similar to female sterile homeotic-related protein Frg-1 [M. musculus] | 3.37311499 |
| AW536361 | | ESTs, Highly similar to KIAA0697 protein [H. sapiens] | 3.364917242 |
| AU045568 | | ESTs, Weakly similar to IgG Fc binding protein [M. musculus] | 3.362501582 |
| AW537446 | Tcea1 | transcription elongation factor A (SII), 1 | 3.353756593 |
| AI666653 | | Mus musculus ubiquitin conjugating enzyme UBC9 mRNA, complete cds | 3.347460034 |
| AU017259 | eed | embryonic ectoderm development | 3.343130988 |
| AI324671 | Rpl30 | Ribosomal protein L30 | 3.343001828 |
| W09723 | | ESTs, Moderately similar to HAT1_HUMAN HISTONE ACETYLTRANSFERASE TYPE B CATALYTIC SUBUNIT [H. sapiens] | 3.342429405 |
| AW545818 | | ESTs, Weakly similar to/prediction | 3.339835947 |
| AA278878 | H2-T23 | histocompatibility 2, T region locus 23 | 3.334974918 |
| AU014886 | Gnb2-rs1 | guanine nucleotide binding protein, beta-2, related sequence 1 | 3.333692828 |
| AW538432 | Rhoip3-pending | Rho interacting protein 3 | 3.330216015 |
| AW537357 | Sdcbp | syndecan binding protein | 3.329064842 |
| AW537048 | Ets2 | E26 avian leukemia oncogene 2,3' domain | 3.325078728 |
| AW549474 | | ESTs, Moderately similar to unknown [H. sapiens] | 3.314824736 |
| AW536101 | | Mus musculus mRNA for phosphorylated adaptor for RNA export (PHAX gene) | 3.313622909 |
| AW557102 | | ESTs, Moderately similar to INSULIN-DEGRADING ENZYME [R. norvegicus] | 3.304747476 |
| AW549980 | | ESTs, Highly similar to UBIQUITIN-CONJUGATING ENZYME E2-17 KD [Drosophila melanogaster] | 3.304680342 |
| AI413942 | | ESTs, Highly similar to UBIQUITIN-CONJUGATING ENZYME E2-17 KD [Drosophila melanogaster] | 3.295674825 |
| AW555047 | | Mus musculus major histocompatibility complex region NG27, NG28, RPS28, NADH oxidoreductase, NG29, KIFC1, Fas-binding protein, BING1, tapasin, RaIGDS-like, KE2, BING4, beta 1,3-galactosyl transferase, and RPS18 genes, complete cds; Sacm21 gene, partial cd | 3.290258007 |
| AA265636 | | ESTs, Highly similar to CALDESMON, SMOOTH MUSCLE [Gallus gallus] | 3.286488615 |
| AW557310 | Kap | kidney androgen regulated protein | 3.275864713 |
| W67062 | | ESTs, Weakly similar to CST1_HUMAN CLEAVAGE STIMULATION FACTOR, 50 KD SUBUNIT [H. sapiens] | 3.272511033 |
| C80438 | Gart | phosphoribosylglycinamide formyltransferase | 3.269100882 |
| AA260352 | | Mus musculus cerebellar postnatal development protein-1 (Cpd1) mRNA, partial cds | 3.268033947 |
| AW536682 | Impnb | importin beta | 3.263591322 |
| AU044944 | Rab11a | RAB11a, member RAS oncogene family | 3.257027215 |
| AW555762 | Tkt | transketolase | 3.255445846 |
| AW536849 | Ccnb1-rs1 | cyclin B1, related sequence 1 | 3.255108538 |
| AW543439 | Fkbp4 | FK506 binding protein 4 (59 kDa) | 3.254740967 |
| AU042923 | | ESTs, Highly similar to dJ483K16.1 [H. sapiens] | 3.250491765 |
| AU045845 | Ywhaq | tyrosine 3-monooxygenase/tryptophan 5-monooxygenase activation protein, theta polypeptide | 3.249673818 |
| AW544115 | | ESTs, Weakly similar to NSP-like 1 [M. musculus] | 3.245183948 |
| AW539262 | Etl1 | enhancer trap locus 1 | 3.240855617 |
| AW545451 | | ESTs, Moderately similar to ribonuclease P protein subunit p14 [H. sapiens] | 3.240611299 |

SUPPLEMENTAL TABLE 4-continued

| Acc No | Gene | Description | N/F ratio |
|---|---|---|---|
| AU015879 | | *Mus musculus* LIM-kinase1 (Limk1) gene, complete cds; Wbscr1 (Wbscr1) gene, alternative splice products, complete cds; and replication factor C, 40 kDa subunit (Rfc2) gene, complete cds | 3.239108652 |
| AA014196 | Glud | Glutamate dehydrogenase | 3.238249096 |
| AU040801 | | ESTs, Highly similar to rer [*M. musculus*] | 3.236111635 |
| AW547945 | | ESTs, Weakly similar to ZIP-kinase [*M. musculus*] | 3.234869937 |
| AW539487 | Pabpc1 | poly A binding protein, cytoplasmic 1 | 3.2298131 |
| AW548914 | | *Mus musculus* receptor activity modifying protein 2 mRNA, complete cds | 3.229667371 |
| AU017822 | | ESTs, Weakly similar to NSP-like 1 [*M. musculus*] | 3.226784472 |
| AU020667 | Uchl3 | ubiquitin carboxyl-terminal esterase L3 (ubiquitin thiolesterase) | 3.225200079 |
| AW536140 | Hsp86-1 | heat shock protein, 86 kDa | 3.220069536 |
| AA289001 | | ESTs, Weakly similar to DDX8_HUMAN PROBABLE ATP-DEPENDENT RNA HELICASE HRH1 [*H. sapiens*] | 3.213217918 |
| AW537501 | | ESTs, Weakly similar to hypothetical 43.2 kDa protein [*H. sapiens*] | 3.212946254 |
| AW536816 | | ESTs, Weakly similar to ZW10 interactor Zwint [*H. sapiens*] | 3.211073781 |
| AW536688 | Tra1 | tumor rejection antigen gp96 | 3.207785549 |
| AW545936 | Cks1 | cyclin-dependent kinase regulatory subunit 1 | 3.202532356 |
| AA168656 | D5Ertd363e | DNA segment, Chr 5, ERATO Doi 363, expressed | 3.199043745 |
| AW550880 | Txn | thioredoxin | 3.194798752 |
| AW557260 | | ESTs, Highly similar to testicular antigen [*M. musculus*] | 3.194109779 |
| AU017619 | Ak3 | adenylate kinase 3 | 3.186508194 |
| AU022272 | Rnaseli | ribonuclease L (2',5'-oligoisoadenylate synthetase-dependent) inhibitor | 3.184559303 |
| AW547818 | Fmr1 | fragile X mental retardation syndrome 1 homolog | 3.184148074 |
| AA013832 | Clpx | caseinolytic protease X (*E. coli*) | 3.183287717 |
| C86748 | Tgfb2 | transforming growth factor, beta 2 | 3.181199624 |
| AW546704 | | ESTs, Highly similar to 40S RIBOSOMAL PROTEIN S13 [*Homo sapiens*; *Rattus norvegicus*] | 3.179558602 |
| AI325159 | | *M. musculus* mRNA for gas5 growth arrest specific protein | 3.171264611 |
| AW536696 | Ndufv1 | NADH dehydrogenase flavoprotein 1 | 3.16947838 |
| AW552833 | | *Mus musculus* LNR42 mRNA, complete cds | 3.160749904 |
| AA080156 | Kap | kidney androgen regulated protein | 3.158901378 |
| AA241756 | sid2057p | small acidic protein sid2057p | 3.155791289 |
| AW547111 | Myhca | myosin heavy chain, cardiac muscle, adult | 3.155653539 |
| AW536212 | | ESTs, Weakly similar to moesin [*R. norvegicus*] | 3.150862062 |
| AI327319 | | ESTs, Highly similar to CYTOCHROME B5 [*Rattus norvegicus*] | 3.150293218 |
| AW550836 | Etl1 | enhancer trap locus 1 | 3.148741977 |
| AW537169 | | ESTs, Weakly similar to misato [*D. melanogaster*] | 3.140606246 |
| AA000038 | Usp23 | ubiquitin specific protease 23 | 3.137407556 |
| AW539360 | | ESTs, Weakly similar to matrin cyclophilin [*R. norvegicus*] | 3.135475267 |
| AW536967 | Etl1 | enhancer trap locus 1 | 3.135171966 |
| AW555020 | | ESTs, Highly similar to UBIQUINOL-CYTOCHROME C REDUCTASE COMPLEX CORE PROTEIN 2 PRECURSOR [*Bos taurus*] | 3.13400887 |
| AW553809 | Rnaseli | ribonuclease L (2',5'-oligoisoadenylate synthetase-dependent) inhibitor | 3.127019793 |
| AA154465 | | ESTs, Highly similar to similar to human DNA-binding protein 5. [*H. sapiens*] | 3.125092795 |
| AA285584 | | *Mus musculus* strain Swiss Webster/NIH actin-associated protein palladin mRNA, partial cds | 3.124624175 |
| AW546078 | Krt2-1 | keratin complex 2, basic, gene 1 | 3.124299027 |
| AU040705 | Erp | endoplasmic reticulum protein | 3.123823806 |
| AI426510 | | *Mus musculus* mkf-1 mRNA, complete cds | 3.116870544 |
| AW549685 | | *M. musculus* mRNA for Pr22 protein | 3.1146672 |
| AU042440 | | ESTs, Weakly similar to BRAIN SPECIFIC POLYPEPTIDE PEP-19 [*Rattus norvegicus*; *M. musculus*] | 3.114535048 |
| AW544818 | Rab18 | RAB18, member RAS oncogene family | 3.109347054 |
| AA237184 | Ddx5 | D-E-A-D (aspartate-glutamate-alanine-aspartate) box polypeptide 5 | 3.108934627 |
| W85513 | | ESTs, Highly similar to KIAA0925 protein [*H. sapiens*] | 3.1043914 |
| C87631 | Zfp68 | Zinc finger protein 68 | 3.103182346 |
| AU042346 | | ESTs, Moderately similar to serine/threonine protein kinase [*M. musculus*] | 3.102909947 |
| C81324 | | ESTs, Highly similar to ISOCITRATE DEHYDROGENASE [*Bos taurus*] | 3.102708564 |
| AI413150 | | HETEROGENEOUS NUCLEAR RIBONUCLEOPROTEIN A1 | 3.101332766 |
| AW544358 | | ESTs, Highly similar to PROTEIN DISULFIDE ISOMERASE PRECURSOR [*Medicago sativa*] | 3.100578685 |
| AW539607 | | ESTs, Weakly similar to All-1 protein +GTE form [*M. musculus*] | 3.099324211 |
| AW546793 | Actg | actin, gamma, cytoplasmic | 3.094036051 |
| C80862 | | ESTs, Moderately similar to (defline not available 5931553) [*M. musculus*] | 3.090776963 |
| AW536256 | Silg81 | silica-induced gene 81 | 3.089849843 |
| AW539609 | Jup | junction plakoglobin | 3.08822389 |
| W98547 | Bad | Bcl-associated death promoter | 3.088183956 |
| AW541488 | B2m | beta-2 microglobulin | 3.069100689 |
| AW545318 | Pcna | proliferating cell nuclear antigen | 3.067845966 |
| AW536215 | Stip1 | stress-induced phosphoprotein 1 | 3.065752133 |
| AU021314 | | *Mus musculus* KOI-4 gene, partial cds | 3.064952305 |
| AA175386 | | *Mus musculus* mRNA for partial LaXp180 protein | 3.063948171 |
| AA068665 | | ESTs, Weakly similar to AF152841_1 polymyositis scleroderma overlap syndrome [*M. musculus*] | 3.05957507 |
| AW554081 | Adnp | activity-dependent neuroprotective protein | 3.055989327 |
| AW538862 | | ESTs, Weakly similar to P9513.2 gene product [*S. cerevisiae*] | 3.054927766 |
| AW554376 | Dlgh1 | discs, large homolog 1 (*Drosophila*) | 3.049574352 |
| AW538403 | | *Mus musculus* formin binding protein 11 (FBP11) mRNA, complete cds | 3.04888214 |

SUPPLEMENTAL TABLE 4-continued

| Acc No | Gene | Description | N/F ratio |
| --- | --- | --- | --- |
| AW541446 | D6Wsu137e | DNA segment, Chr 6, Wayne State University 137, expressed | 3.044611755 |
| AW551959 | Cul1 | cullin 1 | 3.040828115 |
| AW548092 | | *Mus musculus* 14-3-3 protein beta mRNA, complete cds | 3.039487463 |
| AW543750 | | *M. musculus* mRNA for glutamyl-tRNA synthetase | 3.038063168 |
| AW538568 | Rpl44 | ribosomal protein L44 | 3.033122817 |
| AW548061 | | ESTs, Weakly similar to unknown [*C. elegans*] | 3.032513144 |
| AU016110 | | *Mus musculus* heat shock protein (HSPC030) mRNA, complete cds | 3.031383324 |
| C81083 | Hnrnpc | heterogeneous nuclear ribonucleoprotein C2 | 3.030135958 |
| AW554393 | | ESTs, Weakly similar to RNA binding motif protein 7 [*H. sapiens*] | 3.025632148 |
| W13785 | | ribosomal protein S27 | 3.025322982 |
| AW542456 | Lmnb1 | lamin B1 | 3.021908529 |
| AW537278 | Fmo5 | flavin containing monooxygenase 5 | 3.01565301 |
| AI326367 | | *Mus musculus* TCR beta locus from bases 250554 to 501917 (section 2 of 3) of the complete sequence | 3.010492026 |
| AU044431 | | *Mus musculus* DEBT-91 mRNA, complete cds | 3.009214891 |
| W82194 | LOC57423 | hypothetical protein, clone: 2-31 | 3.004332364 |
| AW537132 | Gdap2 | ganglioside-induced differentiation-associated-protein 2 | 3.002468515 |
| AI465251 | | ESTs, Moderately similar to CALPONIN, ACIDIC ISOFORM [*Rattus norvegicus*] | 2.998508138 |
| AU015421 | | ESTs, Highly similar to unknown [*H. sapiens*] | 2.988275793 |
| AW541468 | | ESTs, Highly similar to HYPOTHETICAL 64.5 KD PROTEIN ZK652.9 IN CHROMOSOME III [*Caenorhabditis elegans*] | 2.985037992 |
| AU014587 | | ESTs, Highly similar to POLYADENYLATE-BINDING PROTEIN [*Xenopus laevis*] | 2.983364731 |
| AW536274 | | *Mus musculus* mRNA for Sid6061p, complete cds | 2.975961818 |
| AW554565 | Aop1 | anti-oxidant protein 1 | 2.975547979 |
| AU016907 | Supl15h | suppressor of Lec15 homolog (*C. griseus*) | 2.97343761 |
| AW557067 | Dad1 | defender against cell death 1 | 2.971833739 |
| AU023128 | | ESTs, Highly similar to CAMP-DEPENDENT PROTEIN KINASE TYPE I-ALPHA REGULATORY CHAIN [*Homo sapiens*] | 2.971627282 |
| AA036347 | Klf9 | Kruppel-like factor 9 | 2.968829965 |
| AW536151 | Hsp60 | heat shock protein, 60 kDa | 2.955737367 |
| AW536963 | | ESTs, Highly similar to PUTATIVE ADENOSINE KINASE [*Saccharomyces cerevisiae*] | 2.950322741 |
| AA413694 | Rab7 | RAB7, member RAS oncogene family | 2.948415605 |
| AW554059 | | ESTs, Weakly similar to HYPOTHETICAL 15.9 KD PROTEIN IN GLNA-FDHE INTERGENIC REGION [*Escherichia coli*] | 2.945086458 |
| AW558048 | Cd24a | CD24a antigen | 2.943485748 |
| AW538527 | | ESTs, Moderately similar to R31341_1 [*H. sapiens*] | 2.940115188 |
| AW545662 | | ESTs, Highly similar to 26S PROTEASE REGULATORY SUBUNIT 7 [*Homo sapiens*] | 2.93417407 |
| AW555565 | Zyx | zyxin | 2.929015914 |
| W29492 | Asns | asparagine synthetase | 2.926212129 |
| AA416435 | | ESTs, Highly similar to KIAA0095 gene is related to *S. cerevisiae* NIC96 gene. [*H. sapiens*] | 2.91604107 |
| AI323814 | | Mouse mRNA for ARF4, complete cds | 2.915172345 |
| AI427441 | | *M. musculus* mRNA for neuronal protein 15.6 | 2.914821665 |
| AW538481 | | ESTs, Highly similar to TRANSLATIONAL INITIATION FACTOR 2 BETA SUBUNIT [*Oryctolagus cuniculus*] | 2.905782415 |
| AW552361 | | ESTs, Weakly similar to Similarity to Yeast YIP1 protein [*C. elegans*] | 2.905297661 |
| AU046228 | | ESTs, Highly similar to translation initiation factor IF2 [*H. sapiens*] | 2.904375747 |
| AU044835 | Ppp1cc | protein phosphatase 1, catalytic subunit, gamma isoform | 2.901644309 |
| AA404094 | C11orf17 | C11orf17 | 2.898634353 |
| W85166 | Tacc3 | transforming, acidic coiled-coil containing protein 3 | 2.897486584 |
| AU044566 | | ESTs, Highly similar to VACUOLAR ATP SYNTHASE SUBUNIT D [*Bos taurus*] | 2.897417571 |
| AU020132 | Odc | ornithine decarboxylase, structural | 2.890092488 |
| AW550627 | | *Mus musculus* drebrin E2 mRNA, complete cds | 2.888730948 |
| AU015096 | | ESTs, Weakly similar to nucleolin [*R. norvegicus*] | 2.883466921 |
| W10023 | Catnb | catenin beta | 2.882930209 |
| C80267 | Hnrnpc | heterogeneous nuclear ribonucleoprotein C2 | 2.882107319 |
| C85471 | Pdcd8 | programmed cell death 8 (apoptosis inducing factor) | 2.881879732 |
| AU024091 | Sucla2 | succinate-Coenzyme A ligase, ADP-forming, beta subunit | 2.881062765 |
| AA044475 | Nfe2l2 | Nuclear, factor, erythroid derived 2, like 2 | 2.876121329 |
| AW538967 | | *Mus musculus* mRNA for mDj3, complete cds | 2.874346371 |
| AU041439 | Gnai2 | guanine nucleotide binding protein, alpha inhibiting 2 | 2.87168005 |
| AW544616 | | ESTs, Weakly similar to ZW10 interactor Zwint [*H. sapiens*] | 2.870858344 |
| AI414590 | Srpk2 | Serine/arginine-rich protein specific kinase 2 | 2.864730663 |
| C76867 | | ESTs, Moderately similar to TROPOMYOSIN ALPHA CHAIN, SKELETAL AND CARDIAC MUSCLE [*M. musculus*] | 2.862563996 |
| AI325958 | | ESTs, Highly similar to REPLICATION PROTEIN A 14 KD SUBUNIT [*Homo sapiens*] | 2.862534762 |
| AW555464 | | ESTs, Weakly similar to neuronal-specific septin 3 [*M. musculus*] | 2.857649535 |
| AW536856 | | Mouse testis abundant mRNA sequence | 2.857368245 |
| C78835 | Actx | melanoma X-actin | 2.85464914 |
| AU021567 | Hip2 | huntingtin interacting protein 2 | 2.850054551 |
| AW554115 | Crcp | calcitonin gene-related peptide-receptor component protein | 2.847909648 |
| AW556509 | | ESTs, Highly similar to similar to human DNA-binding protein 5. [*H. sapiens*] | 2.847314257 |
| AW558020 | | ESTs, Highly similar to CELL GROWTH REGULATING NUCLEOLAR PROTEIN [*M. musculus*] | 2.843396393 |
| AW548709 | | ESTs, Moderately similar to EUKARYOTIC INITIATION FACTOR 4A [*Caenorhabditis elegans*] | 2.843274915 |
| AA547555 | Cks1 | CDC28 protein kinase 1 | 2.842163855 |
| AW556999 | | ESTs, Moderately similar to hypothetical protein [*H. sapiens*] | 2.840617772 |

SUPPLEMENTAL TABLE 4-continued

| Acc No | Gene | Description | N/F ratio |
|---|---|---|---|
| AW546373 | | ESTs, Highly similar to 54K arginine-rich nuclear protein [*H. sapiens*] | 2.840574103 |
| AW548748 | | ESTs, Weakly similar to proline-rich protein [*M. musculus*] | 2.840416615 |
| AW536817 | | ESTs, Highly similar to ALPHA ENOLASE [*Mus musculus*] | 2.840261891 |
| AW539487 | Pabpc1 | poly A binding protein, cytoplasmic 1 | 2.84011637 |
| AW537045 | | *Mus musculus* mRNA for initiation factor 2-associated 67 kDa protein, complete cds | 2.83718519 |
| AW544601 | | ESTs, Weakly similar to cDNA EST EMBL:T00542 comes from this gene [*C. elegans*] | 2.83318307 |
| C79176 | | ESTs, Weakly similar to TYROSINE-PROTEIN KINASE JAK3 [*M. musculus*] | 2.826660135 |
| AA185258 | | ESTs, Highly similar to IDN3 [*H. sapiens*] | 2.824275465 |
| AW543973 | | ESTs, Highly similar to thyroid hormone receptor-associated protein complex component TRAP150 [*H. sapiens*] | 2.82307595 |
| AW555383 | | ESTs, Highly similar to NADH-UBIOUINONE OXIDOREDUCTASE B22 SUBUNIT [*Bos taurus*] | 2.820575628 |
| AW549145 | Fkbp3 | FK506-binding protein 3 (25 kD) | 2.812895276 |
| AW545658 | Catns | catenin src | 2.812160453 |
| AW556635 | | ESTs, Weakly similar to splicing factor SC35 [*M. musculus*] | 2.808058439 |
| AW546855 | | *M. musculus* (C57 Black/6X CBA) LAL mRNA for lysosomal acid lipase | 2.802794138 |
| AW553068 | | ESTs, Weakly similar to KIAA0344 [*H. sapiens*] | 2.799512259 |
| W97442 | Map3k12 | mitogen activated protein kinase kinase kinase 12 | 2.798312097 |
| AW536734 | | ESTs, Highly similar to EUKARYOTIC INITIATION FACTOR 4B [*Homo sapiens*] | 2.79472633 |
| C81194 | Hap105 | heat shock protein, 105 kDa | 2.79345821 |
| AA537566 | | Histocompatibility 2, class II antigen A alpha | 2.792318423 |
| AW557878 | | *M. musculus* GAS 6 mRNA associated with growth-arrest | 2.791570157 |
| AW548139 | | *Mus musculus* mRNA, complete cds, clone: 2-31 | 2.79079344 |
| AW555176 | D15Wsu59e | DNA segment, Chr 15, Wayne State University 59, expressed | 2.784158457 |
| AW546427 | | ESTs, Highly similar to RAS-LIKE PROTEIN TC21 [*Homo sapiens*] | 2.78308135 |
| AW537671 | | ESTs, Highly similar to similar to human DNA-binding protein 5. [*H. sapiens*] | 2.779263429 |
| C77223 | Rpo2-1 | RNA polymerase II 1 | 2.776921055 |
| AA000318 | | ESTs, Highly similar to REPLICATION PROTEIN A 14 KD SUBUNIT [*Homo sapiens*] | 2.773773419 |
| AW543985 | | ESTs, Weakly similar to MYELOID DIFFERENTIATION PRIMARY RESPONSE PROTEIN MYD116 [*M. musculus*] | 2.77132421 |
| AW552638 | | Mouse mRNA for dbpA murine homologue, complete cds | 2.769626773 |
| AU043911 | | ESTs, Weakly similar to UBIQUITIN-CONJUGATING ENZYME E2-17 KD 2 [*M. musculus*] | 2.769540325 |
| AW543811 | | ESTs, Weakly similar to HYPOTHETICAL 86.9 KD PROTEIN ZK945.3 IN CHROMOSOME II [*Caenorhabditis elegans*] | 2.767962067 |
| AW538407 | Slc20a1 | solute carrier family 20, member 1 | 2.767681717 |
| AW551944 | | ESTs, Highly similar to Similar to D. melanogaster parallel sister chromatids protein [*Homo sapiens*] | 2.767267283 |
| AW537083 | | ESTs, Highly similar to cellular apoptosis susceptibilty protein [*H. sapiens*] | 2.766532496 |
| AW544737 | Atpl | ATPase-like vacuolar proton channel | 2.763759005 |
| AW556977 | Zpk | zipper (leucine) protein kinase | 2.763133879 |
| AW555759 | Phb | prohibitin | 2.761699761 |
| AW536246 | | ESTs, Highly similar to PUTATIVE METHIONINE AMINOPEPTIDASE 1 [*H. sapiens*] | 2.760259754 |
| AW551817 | Madh4 | MAD homolog 4 (*Drosophila*) | 2.757229361 |
| AA146020 | | *Mus musculus* chromosome X contigB; X-linked lymphocyte regulated 5 gene, Zinc finger protein 28, Zinc finger protein 92, mmxq28orf | 2.756223603 |
| AW554240 | | ESTs, Highly similar to OLIGOSACCHARYL TRANSFERASE STT3 SUBUNIT HOMOLOG [*Caenorhabditis elegans*] | 2.752467221 |
| AU043122 | Cox5b | cytochrome c oxidase, subunit Vb | 2.751396487 |
| AA265396 | Lag | leukemia-associated gene | 2.750567219 |
| AW550641 | Frg1 | FSHD region gene 1 | 2.747989143 |
| C86480 | Plp | proteolipid protein (myelin) | 2.746027119 |
| AA399854 | | ESTs, Highly similar to PUTATIVE ASPARAGINYL-TRNA SYNTHETASE DED81 [*Saccharomyces cerevisiae*] | 2.743198399 |
| C76349 | Sclip | Scgn10 like-protein | 2.742268969 |
| AA509855 | | ESTs, Highly similar to TROPOMYOSIN 4, EMBRYONIC FIBROBLAST ISOFORM [*Rattus norvegicus*] | 2.740953545 |
| AI528760 | | Mouse mRNA for dbpA murine homologue, complete cds | 2.739257165 |
| AW551820 | | ESTs, Highly similar to HYPOTHETICAL 37.2 KD PROTEIN C12C2.09C IN CHROMOSOME I [*Schizosaccharomyces pombe*] | 2.736097382 |
| AW553001 | lslr | immunoglobulin superfamily containing leucine-rich repeat | 2.735275152 |
| AI324702 | | 60S RIBOSOMAL PROTEIN L19 | 2.733803162 |
| AU018011 | | *Mus musculus* truncated SON protein (Son) mRNA, complete cds | 2.729861304 |
| C87907 | Mor2 | malate dehydrogenase, soluble | 2.728657356 |
| AW556389 | Cappb1 | capping protein beta 1 | 2.727836531 |
| AI661905 | | ESTs, Highly similar to similar to nuclear domain 10 protein NDP52 [*H. sapiens*] | 2.72394245 |
| AW537825 | | ESTs, Moderately similar to unknown protein IT12 [*H. sapiens*] | 2.723239257 |
| AA122891 | Gapd | Glyceraldehyde-3-phosphate dehydrogenase | 2.72255977 |
| AW550518 | | *Mus musculus* acidic ribosomal phosphoprotein P1 mRNA, complete cds | 2.722524256 |
| AW546168 | Rps5 | ribosomal protein S5 | 2.722225631 |
| AW549855 | Scp2 | sterol carrier protein 2, liver | 2.72161746 |
| AW555634 | Dld | dihydrolipoamide dehydrogenase | 2.72129 |
| AW537250 | | ESTs, Weakly similar to damage-specific DNA binding protein 1 [*M. musculus*] | 2.720679787 |
| AW553320 | | *Mus musculus* mRNA for ribosomal protein L35a | 2.720548204 |
| AA547684 | | ESTs, Highly similar to translation initiation factor IF2 [*H. sapiens*] | 2.719806487 |
| AW545347 | | ESTs, Highly similar to HYPOTHETICAL 47.4 KD PROTEIN IN PAS1-MST1 INTERGENIC REGION [*Saccharomyces cerevisiae*] | 2.719059223 |

SUPPLEMENTAL TABLE 4-continued

| Acc No | Gene | Description | N/F ratio |
|---|---|---|---|
| AA276030 | Atpl | ATPase-like vacuolar proton channel | 2.715993411 |
| AW555415 | Gtf2i | general transcription factor II I | 2.714548958 |
| AU023806 | Rock1 | Rho-associated coiled-coil forming kinase 1 | 2.714535436 |
| AW557865 | Rad50 | RAD50 homolog (*S. cerevisiae*) | 2.71088834 |
| C77773 | | ESTs, Weakly similar to (define not available 5453421) [*M. musculus*] | 2.706432587 |
| AW557152 | | ESTs, Highly similar to spliceosomal protein SAP 155 [*H. sapiens*] | 2.706136493 |
| AW547604 | | ESTs, Weakly similar to ORF YOL071w [*S. cerevisiae*] | 2.704938801 |
| AW555995 | Lrpap1 | low density lipoprotein receptor related protein, associated protein 1 | 2.70479575 |
| AW556062 | Tex10 | testis expressed gene 10 | 2.704249677 |
| AW536817 | | ESTs, Highly similar to ALPHA ENOLASE [*Mus musculus*] | 2.700717507 |
| AA050086 | Ube2i | ubiquitin-conjugating enzyme E2I | 2.699647334 |
| AI427886 | | ESTs, Highly similar to RAS-RELATED PROTEIN RAB-28 [*R. norvegicus*] | 2.694100196 |
| AA032437 | | ESTs, Moderately similar to DUAL SPECIFICITY PROTEIN PHOSPHATASE PAC-1 [*Homo sapiens*] | 2.688124354 |
| AW551468 | | ESTs, Weakly similar to sorting nexin 1 [*M. musculus*] | 2.684742798 |
| AI451433 | Abc2 | ATP-binding cassette 2 | 2.67945398 |
| AW538472 | Biklk | Bcl2-interacting killer-like | 2.677929061 |
| AW546384 | Psma3 | proteasome (prosome, macropain) subunit, alpha type 3 | 2.675903592 |
| AW550900 | Emd | emerin | 2.674320907 |
| AU019004 | Cd63 | Cd63 antigen | 2.673939197 |
| AI326913 | | ESTs, Highly similar to CYCLIN-DEPENDENT KINASES REGULATORY SUBUNIT 1 [*Homo sapiens*] | 2.672753295 |
| AW536576 | Tex9 | testis expressed gene 9 | 2.671550442 |
| AA031120 | Psma1 | proteasome (prosome, macropain) subunit, alpha type 1 | 2.663765326 |
| AW544996 | M6pr | mannose-6-phosphate receptor, cation dependent | 2.661867728 |
| AI451372 | | ESTs, Weakly similar to similar to kinensin-like protein [*C. elegans*] | 2.661294957 |
| AU022547 | | ESTs, Highly similar to ACTIVATOR 1 38 KD SUBUNIT [*Homo sapiens*] | 2.660297025 |
| AU043450 | Msh2 | mutS homolog 2 (*E. coli*) | 2.659901068 |
| AW536154 | Ctps | CTP synthase | 2.659526849 |
| C76763 | | ESTs, Moderately similar to GOLIATH PROTEIN [*Drosophila melanogaster*] | 2.657128663 |
| AW554567 | Fkbp1a | FK506 binding protein 1a (12 kDa) | 2.653957746 |
| AU018277 | | ESTs, Highly similar to OLIGOSACCHARYL TRANSFERASE STT3 SUBUNIT HOMOLOG [*Caenorhabditis elegans*] | 2.653900272 |
| AW537202 | Dhfr | dihydrofolate reductase | 2.653293004 |
| AW552167 | Il1rak | interleukin 1 receptor-associated kinase | 2.652630575 |
| AA422973 | | ESTs, Moderately similar to AF161556_1 HSPC071 [*H. sapiens*] | 2.652581493 |
| AW536175 | Adh5 | alcohol dehydrogenase 5 | 2.650134514 |
| AW549687 | | *Mus musculus* ribosomal protein L23 (Rpl23) gene, complete cds | 2.649942368 |
| AW537221 | Fgfrp | fibroblast growth factor regulated protein | 2.648558726 |
| AW537334 | | ESTs, Weakly similar to signal recognition particle 54K protein [*M. musculus*] | 2.647412355 |
| AW548330 | | ESTs, Moderately similar to NADH-UBIQUINONE OXIDOREDUCTASE CHAIN 2 [*Mus musculus*] | 2.646892785 |
| AU019197 | Bet3-pending | Bet3 homolog (*S. cerevisiae*) | 2.644793591 |
| AW552337 | | ESTs, Highly similar to RAS-RELATED PROTEIN RAB-6 [*Homo sapiens*] | 2.641220499 |
| AW537799 | | *Mus musculus* SIK similar protein mRNA, complete cds | 2.636695362 |
| AW548397 | | ESTs, Weakly similar to cDNA EST EMBL:T01421 comes from this gene [*C. elegans*] | 2.636437564 |
| C85373 | | ESTs, Highly similar to ARGINYL-TRNA SYNTHETASE, MITOCHONDRIAL PRECURSOR [*Saccharomyces cerevisiae*] | 2.635279092 |
| W64196 | | ESTs, Weakly similar to HG17_MOUSE NONHISTONE CHROMOSOMAL PROTEIN HMG-17 [*M. musculus*] | 2.63462814 |
| W12375 | Hnrpa2b1 | heterogeneous nuclear ribonucleoprotein A2/B1 | 2.633808409 |
| AW539363 | Nsbp1 | nucleosome binding protein 1 | 2.630394701 |
| AU020218 | Zrf2 | zuotin related factor 2 | 2.627413283 |
| AW537655 | Gapd | glyceraldehyde-3-phosphate dehydrogenase | 2.625964554 |
| AW552715 | | ESTs, Weakly similar to DnaJ-like protein [*M. musculus*] | 2.625449507 |
| AW538766 | | ESTs, Weakly similar to HYPOTHETICAL UOG-1 PROTEIN [*M. musculus*] | 2.625140435 |
| AI326146 | | ESTs, Highly similar to HYPOTHETICAL 23.3 KD PROTEIN ZK688.3 IN CHROMOSOME III [*Caenorhabditis elegans*] | 2.62464727 |
| AU040819 | | ESTs, Highly similar to VESICULAR INTEGRAL-MEMBRANE PROTEIN VIP36 PRECURSOR [*Canis familiaris*] | 2.624615038 |
| AW536519 | | ESTs, Weakly similar to lens epithelium-derived growth factor [*H. sapiens*] | 2.623225239 |
| C78609 | | ESTs, Highly similar to EUKARYOTIC INITIATION FACTOR 4 GAMMA [*Oryctolagus cuniculis*] | 2.621287161 |
| AI662104 | | *Mus musculus* CYP2C40 (Cyp2c40) mRNA, complete cds | 2.619833394 |
| AW537395 | Ube3a | ubiquitin conjugating enzyme E3A | 2.619748772 |
| AW554398 | Tcea1 | transcription elongation factor A (SII), 1 | 2.619234745 |
| W09453 | | proton pump polypeptide [*R. rattus*] | 2.618453637 |
| AW544762 | Fbln1 | fibulin 1 | 2.617861014 |
| AI426727 | | ESTs, Weakly similar to 5'-AMP-ACTIVATED PROTEIN KINASE, GAMMA-1 SUBUNIT [*M. musculus*] | 2.617120238 |
| AW537625 | | ESTs, Highly similar to TRNA-PROCESSING PROTEIN SEN3 [*Saccharomyces cerevisiae*] | 2.615208114 |
| AW537195 | | *M. musculus* mRNA for e1 protein | 2.610502282 |
| AW537401 | Pk3 | pyruvate kinase 3 | 2.609416814 |
| AW549044 | | *Mus musculus* SPARC-related protein (SRG) mRNA, complete cds | 2.609089766 |
| AA274739 | Pnn | pinin | 2.604930495 |
| AW556049 | Aco2 | aconitase 2, mitochondrial | 2.602835974 |

SUPPLEMENTAL TABLE 4-continued

| Acc No | Gene | Description | N/F ratio |
|---|---|---|---|
| AA472933 | | ESTs, Highly similar to unknown [*H. sapiens*] | 2.602536474 |
| AW543515 | | ESTs, Highly similar to TRNA-PROCESSING PROTEIN SEN3 [*Saccharomyces cerevisiae*] | 2.600612477 |
| AU020998 | Plat | plasminogen activator, tissue | 2.599921486 |
| AW545301 | Dnpep | aspartyl aminopeptidase | 2.598735375 |
| AI324089 | | EST, Highly similar to PHOSPHATIDYLINOSITOL-4-PHOSPHATE 5-KINASE TYPE II ALPHA [*M. musculus*] | 2.598540553 |
| AW558079 | | ESTs, Weakly similar to PPAR gamma coactivator [*M. musculus*] | 2.596900062 |
| AU021489 | Omd | osteomodulin | 2.593848954 |
| AI327309 | | *Mus musculus* clone TA-9 ATP synthase b chain homolog mRNA, partial cds | 2.591834166 |
| AI427644 | Egfr | Epidermal growth factor receptor | 2.591598589 |
| AW544372 | | ESTs, Highly similar to pEachy [*R. norvegicus*] | 2.591522355 |
| AW537730 | | ESTs, Highly similar to PRE-MRNA SPLICING FACTOR PRP9 [*Saccharomyces cerevisiae*] | 2.589914483 |
| AA034561 | Fen1 | Flap structure specific endonuclease 1 | 2.587417174 |
| W98303 | Sema3a | sema domain, immunoglobulin domain (Ig), short basic domain, secreted, (semaphorin) 3A | 2.586437483 |
| AI528850 | Fasn | Fatty acid synthase | 2.585878999 |
| AW548198 | Gpx3 | glutathione peroxidase 3 | 2.584222275 |
| C86630 | | ESTs, Highly similar to similar to nuclear domain 10 protein NDP52 [*H. sapiens*] | 2.582573765 |
| C87669 | Mod1 | malic enzyme, supernatant | 2.581027133 |
| AA437614 | | ESTs, Highly similar to S1-1 protein [*R. norvegicus*] | 2.580768885 |
| AU018547 | | EST, Weakly similar to NaPi-2 beta [*R. norvegicus*] | 2.580324249 |
| C80147 | Hdgf | hepatoma-derived growth factor | 2.579618455 |
| AI322431 | | ESTs, Highly similar to MICROSOMAL SIGNAL PEPTIDASE 18 KD SUBUNIT [*Canis familiaris*] | 2.579173299 |
| AW548906 | | ESTs, Highly similar to PROBABLE 60S RIBOSOMAL PROTEIN L14EB [*Saccharomyces cerevisiae*] | 2.579131557 |
| AW546306 | Hmg2 | high mobility group protein 2 | 2.57498711 |
| AA208818 | Fxr1h | fragile X mental retardation gene, autosomal homolog | 2.574882839 |
| AU017276 | Ntan1 | N-terminal Asn amidase | 2.571512897 |
| AW536609 | Eif3 | eukaryotic translation initiation factor 3 | 2.57065592 |
| AW548091 | | ESTs, Moderately similar to LAR PROTEIN PRECURSOR [*Homo sapiens*] | 2.570578867 |
| AU023604 | | ESTs, Weakly similar to SEX-LETHAL PROTEIN, FEMALE-SPECIFIC [*Drosophila melanogaster*] | 2.569110342 |
| C81388 | Slc16a1 | solute carrier family 16 (monocarboxylic acid transporters), member 1 | 2.568588458 |
| AA060863 | | *Mus musculus* TSC22-related inducible leucine zipper 1b (Tilz1b) mRNA, complete cds | 2.567506201 |
| AW555706 | Ppia | peptidylprolyl isomerase A | 2.564464822 |
| AW551564 | | *Mus musculus* mRNA for sid2057p, complete cds | 2.559018224 |
| AW548086 | Ptma | prothymosin alpha | 2.558161157 |
| AW550493 | Dbi | diazepam binding inhibitor | 2.555492823 |
| AW544081 | Rbbp7 | retinoblastoma binding protein 7 | 2.554967829 |
| AA003408 | 3-Sep | septin 3 | 2.553331559 |
| AW536320 | Orc4 | origin recognition complex, subunit 4 | 2.55331517 |
| AI324242 | | ESTs, Highly similar to HOMEOBOX PROTEIN OTX1 [*M. musculus*] | 2.552903418 |
| AI573460 | Chd1 | Chromodomain helicase DNA binding protein 1 | 2.550880804 |
| AA061763 | | ESTs, Highly similar to HYPOTHETICAL 70.2 KD PROTEIN IN GSH1-CHS6 INTERGENIC REGION [*Saccharomyces cerevisiae*] | 2.550225644 |
| AW549809 | Abcd4 | ATP-binding cassette, sub-family D (ALD), member 4 | 2.548870042 |
| AW538647 | Rps11 | ribosomal protein S11 | 2.545085369 |
| AW539270 | | ESTs, Highly similar to TUBULIN GAMMA CHAIN [*Homo sapiens*] | 2.543404596 |
| AW536342 | | ESTs, Weakly similar to RSP-1 PROTEIN [*Mus musculus*] | 2.542866132 |
| AW536182 | Sec61a | SEC61, alpha subunit (*S. cerevisiae*) | 2.542719816 |
| AW539649 | | ESTs, Highly similar to DEK PROTEIN [*Homo sapiens*] | 2.542495091 |
| AA426845 | Sox15 | SRY-box containing gene 15 | 2.54230538 |
| AI427918 | | ESTs, Moderately similar to dJ206D15.3 [*H. sapiens*] | 2.541668093 |
| AW547546 | Pmp20-pending | peroxisomal membrane protein 20 | 2.540500727 |
| AA266975 | Cdc42 | Cell division cycle 42 | 2.539715246 |
| AW557331 | | ESTs, Weakly similar to F15D4.3 [*C. elegans*] | 2.53958994 |
| AU042135 | | ESTs, Moderately similar to protocadherin-3 [*R. norvegicus*] | 2.539044703 |
| AW555666 | | ESTs, Highly similar to CAMP-DEPENDENT PROTEIN KINASE TYPE I-ALPHA REGULATORY CHAIN [*Homo sapiens*] | 2.538023165 |
| AW549721 | Hspa9a | heat shock protein, 74 kDa, A | 2.535480124 |
| AU023995 | | *Mus musculus* chromosome segregation protein SmcB (SmcB) mRNA, complete cds | 2.530486227 |
| AW541453 | Capg | capping protein (actin filament), gelsolin-like | 2.530408897 |
| AA222216 | Tubb4 | tubulin, beta 4 | 2.528905535 |
| AW536795 | Clk | CDC-like kinase | 2.522978124 |
| AW557901 | | ESTs, Weakly similar to C54G7.4 gene product [*C. elegans*] | 2.522377919 |
| AW552709 | | *Mus musculus* brain protein 44-like protein (Brp44l) mRNA, complete cds | 2.521723313 |
| AW536179 | | ESTs, Weakly similar to CGI-59 protein [*H. sapiens*] | 2.521255841 |
| C86107 | Actn3 | actinin alpha 3 | 2.520902204 |
| AU044498 | Bcap37 | B-cell receptor-associated protein 37 | 2.518818666 |
| AW547403 | Adcyap1r1 | adenylate cyclase activating polypeptide 1 receptor 1 | 2.518240435 |
| AW554737 | | ESTs, Weakly similar to KIAA0512 protein [*H. sapiens*] | 2.514867936 |
| AA445435 | | ESTs, Moderately similar to PTD017 [*H. sapiens*] | 2.512197233 |
| AU016461 | Ssfa1 | sperm specific antigen 1 | 2.512128647 |

SUPPLEMENTAL TABLE 4-continued

| Acc No | Gene | Description | N/F ratio |
|---|---|---|---|
| AA080011 | Ywhae | Tyrosine 3-monooxygenase/tryptophan 5-monooxygenase activatioprotein, epsilon polypeptide | 2.511644859 |
| AU022118 | Pnn | pinin | 2.511460674 |
| AW539549 | | ESTs, Highly similar to KIAA0095 gene is related to *S. cerevisiae* NIC96 gene. [*H. sapiens*] | 2.510991932 |
| AW553714 | Tlk | Tousled-like kinase (*Arabidopsis*) | 2.510671023 |
| C86454 | | ESTs, Weakly similar to SOX13 [*M. musculus*] | 2.510141101 |
| AA474681 | | ESTs, Moderately similar to A53770 growth factor-responsive protein, vascular smooth muscle-rat [*R. norvegicus*] | 2.509526639 |
| AW552886 | Vcp | valosin containing protein | 2.50801841 |
| AU021911 | | ESTs, Moderately similar to ERYTHROID KRUEPPEL-LIKE TRANSCRIPTION FACTOR [*Mus musculus*] | 2.507198715 |
| AW539120 | | ESTs, Weakly similar to BETA-MANNOSIDASE PRECURSOR [*H. sapiens*] | 2.505882042 |
| AU042815 | LOC53325 | putative transcription factor | 2.505471313 |
| AW544505 | Soat1 | sterol O-acyltransferase 1 | 2.498847559 |
| AW546367 | | *Mus musculus* CRIPT protein mRNA, complete cds | 2.497650335 |
| AW551726 | Wbp5 | WW domain binding protein 5 | 2.496644567 |
| W97837 | D10Ertd322e | DNA segment, Chr 10, ERATO Doi 322, expressed | 2.494826439 |
| AU016534 | | ESTs, Weakly similar to PARATHYMOSIN [*Rattus norvegicus*] | 2.493713568 |
| AW546141 | Macs | myristoylated alanine rich protein kinase C substrate | 2.492012377 |
| AW547469 | Ywhae | tyrosine 3-monooxygenase/tryptophan 5-monooxygenase activatioprotein, epsilon polypeptide | 2.491814894 |
| AW539320 | Pl1 | placental lactogen 1 | 2.490879313 |
| AW555985 | Rpa2 | replication protein A2 | 2.490514775 |
| AA050684 | Silg81 | silica-induced gene 81 | 2.490476063 |
| AW544374 | Fin14 | fibroblast growth factor inducible 14 | 2.490464918 |
| AA016827 | | ESTs, Weakly similar to RING CANAL PROTEIN [*Drosophila melanogaster*] | 2.489325106 |
| AU015783 | | ESTs, Highly similar to unknown [*H. sapiens*] | 2.489003752 |
| AW555631 | | ESTs, Highly similar to PUTATIVE RECEPTOR PROTEIN [*Homo sapiens*] | 2.488892742 |
| C80070 | | ESTs, Moderately similar to hypothetical protein [*H. sapiens*] | 2.488351328 |
| AA016810 | D15Wsu77e | DNA segment, Chr 15, Wayne State University 77, expressed | 2.487746386 |
| AA000223 | | *Mus musculus* SPARC-related protein (SRG) mRNA, complete cds | 2.484495842 |
| AU045850 | | ESTs, Highly similar to PUTATIVE ATP-DEPENDENT RNA HELICASE T26G10.1 IN CHROMOSOME III [*Caenorhabditis elegans*] | 2.480950679 |
| AI326091 | | *Mus musculus* antioxidant enzyme AOE372 mRNA, complete cds | 2.480362721 |
| AA014915 | Hsp74 | Heat shock protein, 74 kDa | 2.479501024 |
| AW544689 | | ESTs, Weakly similar to KIAA0869 protein [*H. sapiens*] | 2.478339667 |
| AW542349 | | ESTs, Highly similar to SIGNAL RECOGNITION PARTICLE 72 KD PROTEIN [*Canis familiaris*] | 2.474356861 |
| AI426202 | | ESTs, Highly similar to leucine-rich-domain inter-acting protein 1 [*M. musculus*] | 2.472494776 |
| AW543636 | Anxa5 | annexin A5 | 2.471442908 |
| AW553103 | | ESTs, Weakly similar to es 64 [*M. musculus*] | 2.470432192 |
| AI448428 | | ESTs, Weakly similar to Rigui [*M. musculus*] | 2.470113702 |
| AW546519 | Trt | translationally regulated transcript (21 kDa) | 2.469720709 |
| AW539820 | Lv | delta-aminolevulinate dehydratase | 2.468434243 |
| AU046028 | | ESTs, Moderately similar to RNA polymerase II transcription factor SIII p18 subunit [*R. norvegicus*] | 2.467860062 |
| AW555561 | Mybl2 | myeloblastosis oncogene-like 2 | 2.467492726 |
| AW543683 | Ncl | nucleolin | 2.466832971 |
| W13561 | Jag2 | jagged 2 | 2.465200657 |
| AU016137 | Fth | ferritin heavy chain | 2.464959455 |
| AW536987 | Snta1 | syntrophin, acidic 1 | 2.464853599 |
| AW536435 | | ESTs, Moderately similar to KIAA0755 protein [*H. sapiens*] | 2.463881083 |
| AI327112 | | *Mus musculus* NADP-dependent isocitrate dehydrogenase (Idh) mRNA, complete cds | 2.463800442 |
| AA268327 | | ESTs, Highly similar to FIBRILLIN 1 PRECURSOR [*Homo sapiens*] | 2.462447346 |
| AI528700 | Rab1 | RAB1, member RAS oncogene family | 2.46222509 |
| AA220617 | Bak | Bcl2 homologous antagonist/killer | 2.461291028 |
| AW542307 | Gtpbp | GTP binding protein 1 | 2.460990263 |
| AU022218 | Ptp4a1 | protein tyrosine phosphatase 4a1 | 2.459877353 |
| W81857 | | ESTs, Highly similar to HYPOTHETICAL 39.7 KD PROTEIN C34E10.2 IN CHROMOSOME III [*Caenorhabditis elegans*] | 2.458320944 |
| C78257 | | ESTs, Highly similar to (defline not available 6012071) [*R. norvegicus*] | 2.45776456 |
| AW539362 | | ESTs, Highly similar to KIAA0515 protein [*H. sapiens*] | 2.455566909 |
| AA274915 | U2af1-rs1 | U2 small nuclear ribonucleoprotein auxiliary factor (U2AF), 35 kDa, related sequence 1 | 2.454199936 |
| AW536155 | Ddx5 | DEAD (aspartate-glutamate-alanine-aspartate) box polypeptide 5 | 2.450399008 |
| AI451115 | Tcof1 | Treacher Collins Franceschetti syndrome 1, homolog | 2.449114592 |
| AI415181 | | ESTs, Highly similar to adaptor protein [*H. sapiens*] | 2.447784219 |
| C87823 | | ESTs, Weakly similar to cDNA EST EMBL:T01156 comes from this gene [*C. elegans*] | 2.446705774 |
| AU045477 | | *M. musculus* ASF mRNA | 2.44424645 |
| C87175 | | ESTs, Highly similar to TUBULIN BETA CHAIN [*Lytechinus pictus*] | 2.444103591 |
| AW555877 | Gdi3 | guanosine diphosphate (GDP) dissociation inhibitor 3 | 2.443313285 |
| AU023429 | | ESTs, Moderately similar to heat shock factor binding protein 1 HSBP1 [*H. sapiens*] | 2.443174621 |
| AW551192 | Psme1 | protease (prosome, macropain) 28 subunit, alpha | 2.442839637 |
| AW545938 | Sap18 | Sin3-associated polypeptide 18 | 2.441113088 |
| AU016501 | Ltbp3 | latent transforming growth factor beta binding protein 3 | 2.439347726 |
| AW551042 | | *Mus musculus* X chromosome: L1cam locus | 2.438710922 |
| AW552195 | | ESTs, Highly similar to MITOCHONDRIAL IMPORT RECEPTOR SUBUNIT TOM20 HOMOLOG [*R. norvegicus*] | 2.4386961 |

SUPPLEMENTAL TABLE 4-continued

| Acc No | Gene | Description | N/F ratio |
| --- | --- | --- | --- |
| AW542335 | | ESTs, Highly similar to MICROSOMAL SIGNAL PEPTIDASE 21 KD SUBUNIT [*Canis familiaris*] | 2.436734688 |
| AW547166 | | ESTs, Highly similar to UBIQUINOL-CYTOCHROME C REDUCTASE COMPLEX 14 KD PROTEIN [*Bos taurus*] | 2.436219154 |
| AA068842 | Ubc2e | ubiquitin conjugating enzyme 2e | 2.435798543 |
| AU016480 | | ESTs, Highly similar to 40S RIBOSOMAL PROTEIN S25 [*Homo sapiens*; *Rattus norvegicus*] | 2.434092714 |
| AU023232 | Pigf | phosphatidylinositol glycan, class F | 2.433935408 |
| AA266531 | AA930106 | EST AA930106 | 2.43269159 |
| AW548819 | | ESTs, Moderately similar to acidic 82 kDa protein [*H. sapiens*] | 2.432596162 |
| AA517431 | | ESTs, Moderately similar to GLYCOPROTEIN 25L PRECURSOR [*Canis familiaris*] | 2.431952116 |
| AA000842 | | ESTs, Highly similar to KINESIN-II 85 KD SUBUNIT [*Strongylocentrotus purpuratus*] | 2.4312569 |
| AU020424 | Slc12a2 | solute carrier family 12, member 2 | 2.42972381 |
| W08137 | | ESTs, Weakly similar to HYPOTHETICAL 86.9 KD PROTEIN ZK945.3 IN CHROMOSOME II [*Caenorhabditis elegans*] | 2.429186971 |
| AW536067 | Aop2 | anti-oxidant protein 2 | 2.425678079 |
| AW555001 | | *Mus musculus* RW1 protein mRNA, complete cds | 2.422600237 |
| AA274946 | Eif1a | eukaryotic translation initiation factor 1A | 2.420039228 |
| AW557915 | Ezh1 | enhancer of zeste homolog 1 (*Drosophila*) | 2.416855801 |
| AA168538 | Orc4 | origin recognition complex, subunit 4 | 2.413722611 |
| AW537427 | Tstap91a | tissue specific transplantation antigen P91A | 2.413410871 |
| AI429159 | | ESTs, Weakly similar to ultra-high-sulfur keratin 1 [*M. musculus*] | 2.413170232 |
| AW536433 | Hsp70-4 | heat shock protein, 70 kDa 4 | 2.413114212 |
| AW541013 | | ESTs, Moderately similar to HYPOTHETICAL PROTEIN HI0376 [*Haemophilus influenzae*] | 2.412854555 |
| AA272821 | | ESTs, Highly similar to PUTATIVE ADENOSINE KINASE [*Saccharomyces cerevisiae*] | 2.412651495 |
| AW552159 | Atp2a2 | ATPase, Ca++ transporting, cardiac muscle, slow twitch 2 | 2.409551934 |
| AW555351 | | *Mus musculus domesticus* mitochondrial carrier homolog 1 isoform a mRNA, complete cds; nuclear gene for mitochondrial product | 2.408853343 |
| AI323543 | | *Mus musculus* (clone: pMAT1) mRNA, complete cds | 2.40628791 |
| AW536140 | Hsp86-1 | heat shock protein, 86 kDa 1 | 2.405500262 |
| C76941 | Tif1b | transcriptional intermediary factor 1, beta | 2.40299958 |
| AA414211 | | ESTs, Highly similar to RSP5 PROTEIN [*Saccharomyces cerevisiae*] | 2.401776272 |
| W08937 | | FAN protein | 2.401104291 |
| AW549671 | | ESTs, Weakly similar to SOX13 [*M. musculus*] | 2.398051225 |
| AA416246 | Pmp22 | Peripheral myelin protein, 22 kDa | 2.394587625 |
| AI427491 | | ESTs, Highly similar to PROBABLE UBIQUITIN CARBOXYL-TERMINAL HYDROLASE [*Homo sapiens*] | 2.394177647 |
| AU015183 | Ptprc | protein tyrosine phosphatase, receptor type, C | 2.393529137 |
| AA031056 | Mcmd5 | mini chromosome maintenance deficient 5 (*S. cerevisiae*) | 2.391689429 |
| C87726 | | *Mus musculus* mitotic checkpoint component Mad2 mRNA, complete cds | 2.391344308 |
| AW552558 | Eif2s3x | eukaryotic translation initiation factor 2, subunit 3, structural gene X-linked | 2.390411491 |
| AW547239 | | ESTs, Highly similar to TRANSLOCON-ASSOCIATED PROTEIN, ALPHA SUBUNIT PRECURSOR [*Canis familiaris*] | 2.388404892 |
| AW552412 | | ESTs, Highly similar to TRANSLOCON-ASSOCIATED PROTEIN, BETA SUBUNIT PRECURSOR [*Homo sapiens*] | 2.385307516 |
| AU018839 | Hmg14 | high mobility group protein 14 | 2.384908256 |
| AA403949 | Capn12 | calpain 12 | 2.38344367 |
| C86052 | Cnn1 | calponin 1 | 2.380586251 |
| AW549140 | | ESTs, Weakly similar to Peter Pan [*D. melanogaster*] | 2.379705926 |
| AA245492 | | ESTs, Moderately similar to AF151064_1 HSPC230 [*H. sapiens*] | 2.379149074 |
| AA466838 | | ESTs, Highly similar to Cdc5-like protein [*R. norvegicus*] | 2.377796701 |
| AW552727 | Fasn | fatty acid synthase | 2.377306081 |
| AA020034 | | ESTs, Weakly similar to cleft lip and palate transmembrane protein 1 [*H. sapiens*] | 2.376903716 |
| AA023641 | Madh3 | MAD homolog 3 (*Drosophila*) | 2.376148136 |
| C86367 | | ESTs, Weakly similar to BAT2 [*M. musculus*] | 2.375988234 |
| AA388122 | Mem3 | Maternal embryonic message 3 | 2.374556107 |
| AA004149 | | ESTs, Weakly similar to PROBABLE PEPTIDYL-TRNA HYDROLASE [*Bacillus subtilis*] | 2.373057115 |
| AW553203 | | *Mus musculus* mRNA, complete cds, clone: 2-24 | 2.371518772 |
| AW536206 | Hsp86-1 | heat shock protein, 86 kDa 1 | 2.370643703 |
| W91463 | Ddef1 | development and differentiation enhancing | 2.369512617 |
| AW548540 | | *Mus musculus* SIK similar protein mRNA, complete cds | 2.368814949 |
| AA288977 | | ESTs, Moderately similar to GOLIATH PROTEIN [*Drosophila melanogaster*] | 2.368498766 |
| AA033138 | Ant2 | Adenine nucleotide translocator 2, fibroblast | 2.36746577 |
| AW536910 | | ESTs, Moderately similar to chromosome-associated protein-E [*H. sapiens*] | 2.365185976 |
| AW556217 | Ash2l | ash2 (absent, small, or homeotic)-like (*Drosophila*) | 2.364972967 |
| AA266868 | | ESTs, Highly similar to RIBOSOMAL PROTEIN S6 KINASE [*Homo sapiens*] | 2.364627315 |
| C81301 | Rbpsuh | recombining binding protein suppressor of hairless (*Drosophila*) | 2.364326297 |
| AA274539 | | *Mus musculus* mRNA for 26S proteasome non-ATPase subunit | 2.362706461 |
| AI325930 | | ESTs, Highly similar to CELL DIVISION CONTROL PROTEIN 23 [*Saccharomyces cerevisiae*] | 2.361095885 |
| AW555373 | | *Mus musculus* short coiled coil protein SCOCO (Scoc) mRNA, complete cds | 2.36056201 |
| AW554706 | | ESTs, Highly similar to hypothetical protein [*H. sapiens*] | 2.357478513 |
| AW551989 | Eef2 | eukaryotic translation elongation factor 2 | 2.357184652 |
| AA203922 | Tmod3 | tropomodulin 3 | 2.355290717 |
| AU041196 | | ESTs, Highly similar to 60S RIBOSOMAL PROTEIN L22 [*Tripneustes gratilla*] | 2.355169604 |

SUPPLEMENTAL TABLE 4-continued

| Acc No | Gene | Description | N/F ratio |
|---|---|---|---|
| AA290484 | | ESTs, Weakly similar to SPORULATION-SPECIFIC PROTEIN 1 [*Saccharomyces cerevisiae*] | 2.354693252 |
| AU046294 | Magoh | mago-nashi homolog, proliferation-associated (*Drosophila*) | 2.353138844 |
| AA050900 | Egr1 | Early growth response 1 | 2.352134769 |
| AW548009 | | ESTs, Highly similar to PTD014 [*H. sapiens*] | 2.346432008 |
| AU023893 | | ESTs, Highly similar to choline/ethanolaminephosphotransferase [*H. sapiens*] | 2.343732092 |
| AW537685 | | ESTs, Highly similar to HYPOTHETICAL 83.2 KD PROTEIN IN CHA1-APA1/DTP INTERGENIC REGION [*Saccharomyces cerevisiae*] | 2.342999287 |
| AW540984 | Api4 | apoptosis inhibitor 4 | 2.342898046 |
| C77892 | Hba-a1 | hemoglobin alpha, adult chain 1 | 2.342638604 |
| AU019031 | Hist4 | histone 4 protein | 2.341178338 |
| AI414575 | | ESTs, Moderately similar to HISTONE ACETYLTRANSFERASE TYPE B CATALYTIC SUBUNIT [*H. sapiens*] | 2.340858323 |
| AU043242 | | ESTs, Weakly similar to ORF YKR081c [*S. cerevisiae*] | 2.340501043 |
| AW553194 | | *Mus musculus* Cope1 mRNA for nonclathrin coat protein epsilon-COP, complete cds | 2.339239681 |
| AW556204 | | ESTs, Weakly similar to ORF YGR200c [*S. cerevisiae*] | 2.339173959 |
| AU043007 | | *M. musculus* mRNA for neuronal protein 15.6 | 2.339134449 |
| AW536641 | | ESTs, Highly similar to CLATHRIN HEAVY CHAIN [*Rattus norvegicus*] | 2.338980841 |
| AU040648 | | ESTs, Weakly similar to ORF YNL061w [*S. cerevisiae*] | 2.337816604 |
| AW558198 | Emap2 | endothelial monocyte activating polypeptide 2 | 2.335465842 |
| AU043578 | Tacc3 | transforming, acidic coiled-coil containing protein 3 | 2.332924372 |
| AW547363 | Fmo5 | flavin containing monooxygenase 5 | 2.330683655 |
| W44162 | | ESTs, Moderately similar to N153_RAT NUCLEAR PORE COMPLEX PROTEIN NUP153 [*R. norvegicus*] | 2.330309625 |
| AU015616 | | ESTs, Weakly similar to cDNA EST yk338f6.5 comes from this gene [*C. elegans*] | 2.330288731 |
| AI322439 | | ESTs, Moderately similar to SIGNAL RECOGNITION PARTICLE 19 KD PROTEIN [*Homo sapiens*] | 2.329157971 |
| AW544876 | | ESTs, Highly similar to TRANSCRIPTION FACTOR BTF3 [*Homo sapiens*] | 2.327613924 |
| AW536151 | Hsp60 | heat shock protein, 60 kDa | 2.327256569 |
| AW549706 | Nedd4 | neural precursor cell expressed, developmentally down-regulated gene 4 | 2.327084972 |
| AW555062 | | ESTs, Weakly similar to snRNP protein B [*D. melanogaster*] | 2.322730091 |
| AW556238 | | ESTs, Moderately similar to striatin [*M. musculus*] | 2.321466801 |
| AA444533 | | ESTs, Highly similar to G10 PROTEIN [*Xenopus laevis*] | 2.319746228 |
| AI451613 | | ESTs, Highly similar to CYP4B1 [*M. musculus*] | 2.318913225 |
| AU023815 | | ESTs, Weakly similar to (defline not available 5901816) [*D. melanogaster*] | 2.318446678 |
| AA052404 | CRIPT | CRIPT protein | 2.318310231 |
| AW547917 | | ESTs, Highly similar to SINGLE-STRANDED DNA-BINDING PROTEIN, MITOCHONDRIAL PRECURSOR [*Rattus norvegicus*] | 2.317172841 |
| AW536738 | Klf9 | Kruppel-like factor 9 | 2.316449053 |
| AW537096 | | ESTs, Highly similar to GLUTAMINYL-TRNA SYNTHETASE [*Homo sapiens*] | 2.316069284 |
| AW552222 | H19 | H19 fetal liver mRNA | 2.315271509 |
| AW552411 | Ech1 | enoyl coenzyme A hydratase 1, peroxisomal | 2.315044879 |
| AW556441 | | ESTs, Moderately similar to NY-REN-45 antigen [*H. sapiens*] | 2.314566763 |
| AW537615 | Orc1 | origin recognition complex, subunit 1 homolog (*S. cerevisiae*) | 2.313001263 |
| AW554187 | G2an | alpha glucosidase 2, alpha neutral subunit | 2.312088278 |
| AW556339 | | ESTs, Highly similar to RN protein [*R. norvegicus*] | 2.311016095 |
| AW536573 | | ESTs, Weakly similar to similar to leucyl-tRNA synthetase [*C. elegans*] | 2.311009258 |
| AU044452 | Nit1 | nitrilase 1 | 2.31027286 |
| AU040813 | | ESTs, Weakly similar to T23G11.9 [*C. elegans*] | 2.309549316 |
| AU021615 | | ESTs, Highly similar to SET PROTEIN [*Homo sapiens*] | 2.30703954 |
| AA444224 | | ESTs, Highly similar to UBP7_HUMAN UBIQUITIN CARBOXYL-TERMINAL HYDROLASE 7 [*H. sapiens*] | 2.305871297 |
| AU023417 | Xnp | X-linked nuclear protein | 2.30515632 |
| AW556482 | | ESTs, Moderately similar to hypothetical protein [*H. sapiens*] | 2.303394618 |
| AW546518 | Erh | enhancer of rudimentary homolog (*Drosophila*) | 2.303065378 |
| AA268423 | Rdh5 | retinol dehydrogenase type 5 | 2.301249007 |
| AA014771 | Pkcz | protein kinase C, zeta | 2.298782934 |
| AW545976 | Cops7a | COP9 (constitutive photomorphogenic), subunit 7a (*Arabidopsis*) | 2.297823068 |
| AU015592 | Ybx1 | Y box protein 1 | 2.296828893 |
| AW552368 | | ESTs, Weakly similar to F42A6.6 [*C. elegans*] | 2.296724442 |
| AU016947 | Rbbp6 | retinoblastoma binding protein 6 | 2.293981468 |
| AW539367 | | *Mus musculus* ribosomal protein L23 (Rpl23) gene, complete cds | 2.293923928 |
| AW549937 | Hdac2 | histone deacetylase 2 | 2.292864895 |
| AW553303 | | ESTs, Highly similar to NADH-UBIQUINONE OXIDOREDUCTASE 19 KD SUBUNIT [*Bos taurus*] | 2.292305877 |
| AW557882 | Anxa7 | annexin A7 | 2.291896987 |
| W34474 | | ESTs, Highly similar to HAM1 PROTEIN [*Saccharomyces cerevisiae*] | 2.290024001 |
| AW544089 | | ESTs, Highly similar to unknown [*H. sapiens*] | 2.289029466 |
| AW553526 | Npm1 | nucleophosmin 1 | 2.288099461 |
| AA444943 | | ESTs, Highly similar to GLYCOPROTEIN 25L PRECURSOR [*Canis familiaris*] | 2.28632601 |
| AW553602 | | ESTs, Weakly similar to (define not available 6016842) [*M. musculus*] | 2.285573594 |
| AW554909 | Rpl8 | ribosomal protein L8 | 2.285360197 |
| AU020790 | | *Mus musculus* BAF53a (Baf53a) mRNA, complete cds | 2.284270468 |
| AU024674 | | ESTs, Highly similar to CITRATE SYNTHASE, MITOCHONDRIAL PRECURSOR [*Sus scrofa*] | 2.28323685 |
| C88330 | | ESTs, Weakly similar to weak similarity to the yeast SSM4 protein [*C. elegans*] | 2.282437195 |
| AW536926 | | ESTs, Highly similar to KIAA0601 protein [*H. sapiens*] | 2.282157312 |
| W48017 | | ESTs, Highly similar to AF151859_1 CGI-101 protein [*H. sapiens*] | 2.28097946 |

SUPPLEMENTAL TABLE 4-continued

| Acc No | Gene | Description | N/F ratio |
|---|---|---|---|
| W13152 | | ESTs, Highly similar to CYCLIN-DEPENDENT KINASES REGULATORY SUBUNIT 2 [Homo sapiens] | 2.280916964 |
| AA388377 | D5Ertd363e | DNA segment, Chr 5, ERATO Doi 363, expressed | 2.280662428 |
| AW536490 | Usp5 | ubiquitin specific protease 5 (isopeptidase T) | 2.27846001 |
| AW546788 | Tgfbi | transforming growth factor, beta induced, 68 kDa | 2.275899113 |
| C80729 | Catna1 | catenin alpha 1 | 2.275074652 |
| AI426199 | | ESTs, Weakly similar to stromal cell-derived factor 2 [M. musculus] | 2.273575265 |
| AW554921 | | ESTs, Weakly similar to KIAA0690 protein [H. sapiens] | 2.270891671 |
| AA541870 | | ESTs, Highly similar to arsenate resistance protein ARS2 [H. sapiens] | 2.264516126 |
| AW548210 | | ESTs, Highly similar to 40S RIBOSOMAL PROTEIN S25 [Homo sapiens; Rattus norvegicus] | 2.262604986 |
| AI427473 | | ESTs, Moderately similar to COP9 PROTEIN [Arabidopsis thaliana] | 2.262114744 |
| AW538852 | Hmg14 | high mobility group protein 14 | 2.259961047 |
| AA030447 | Prph1 | Peripherin | 2.25921575 |
| AW536727 | | ESTs, Highly similar to HYPOTHETICAL 18.5 KD PROTEIN C12G12.05C IN CHROMOSOME IN [Schizosaccharomyces pombe] | 2.254945336 |
| AW552406 | | Mus musculus ATP synthase gamma-subunit gene, nuclear gene encoding a mitochondrial protein, partial cds | 2.25252829 |
| C78511 | Biklk | Bcl2-interacting killer-like | 2.2503145 |
| AI451984 | Prim1 | DNA primase, p49 subunit | 2.250302092 |
| AW544726 | Ywhaz | tyrosine 3-monooxygenase/tryptophan 5-monooxygenase activation protein, zeta polypeptide | 2.248914858 |
| AW538474 | | ESTs, Highly similar to PUTATIVE SERINE/THREONINE-PROTEIN KINASE A [Trypanosoma brucei brucei] | 2.247826338 |
| AW551451 | Spnb2 | beta-spectrin 2, non-erythrocytic | 2.245979336 |
| AW556933 | | ESTs, Weakly similar to PUTATIVE PRE-MRNA SPLICING FACTOR RNA HELICASE [H. sapiens] | 2.245882244 |
| AA049766 | | ESTs, Highly similar to KIAA0560 protein [H. sapiens] | 2.244003084 |
| AW552799 | | ESTs, Weakly similar to predicted using Genefinder [C. elegans] | 2.243647865 |
| AW536273 | Mcmd5 | mini chromosome maintenance deficient 5 (S. cerevisiae) | 2.243088262 |
| AA003951 | Alas2 | Aminolevulinic acid synthase 2, erythroid | 2.241855839 |
| AW544857 | | ESTs, Highly similar to ISOCITRATE DEHYDROGENASE [Bos taurus] | 2.241748363 |
| AA014456 | Atp6k | ATPase, H+ transporting lysosomal (vacuolar proton pump), 9.2 kDa | 2.23872792 |
| AA254528 | Magoh | mago-nashi homolog, proliferation-associated (Drosophila) | 2.236163487 |
| AU015485 | | ESTs, Weakly similar to PROBABLE PEROXISOMAL ENOYL-COA HYDRATASE [M. musculus] | 2.235591843 |
| AW553551 | | ESTs, Highly similar to calcium-independent alpha-latrotoxin receptor homolog 2 [R. norvegicus] | 2.235170069 |
| AU024141 | | ESTs, Highly similar to UBIQUITIN [Homo sapiens; Bos taurus; Sus scrofa; Cavia porcellus;Cricetulus griseus;Cricetulus longicaudatus;Rattus norvegicus;Mus musculus; Oryctlagus cuniculus; Gallus gallus; Xenopus laevis; Drosophila melanogaster; Cerati | 2.232630685 |
| C81381 | | ESTs, Weakly similar to BcDNA.GH03108 [D. melanogaster] | 2.2321414 |
| AW554765 | | ESTs, Moderately similar to tpr protein [H. sapiens] | 2.231202975 |
| AI323810 | | Mouse nucleolar protein N038 mRNA, complete cds | 2.23056495 |
| AW537485 | Pla2g6 | 85 kDa calcium-independent phospholipase A2 | 2.230310343 |
| AW556373 | | ESTs, Highly similar to HAM1 PROTEIN [Saccharomyces cerevisiae] | 2.228965982 |
| AU024437 | | ESTs, Weakly similar to rit [M. musculus] | 2.228758058 |
| AU023680 | | ESTs, Highly similar to SET PROTEIN [Homo sapiens] | 2.228390926 |
| W53962 | Tgfb2 | Transforming growth factor, beta 2 | 2.228071514 |
| AW544412 | | ESTs, Highly similar to TUBULIN BETA CHAIN [Lytechinus pictus] | 2.226024845 |
| AA423209 | Psme3 | Proteaseome (prosome, macropain) 28 subunit, 3 | 2.222939666 |
| AU042116 | | ESTs, Highly similar to 40S RIBOSOMAL PROTEIN S10 [Homo sapiens] | 2.222175184 |
| AU041939 | | Mus musculus TBX1 protein mRNA, complete cds | 2.221932511 |
| W83038 | Csnk | casein kappa | 2.220674318 |
| AU016810 | | EST, Weakly similar to coxsackie and adenovirus receptor homologue [M. musculus] | 2.220628518 |
| AA272067 | Fth | ferritin heavy chain | 2.21966855 |
| AW550222 | Mc2r | melanocortin 2 receptor | 2.219421336 |
| AW546733 | | Mus musculus mRNA for Arp2/3 complex subunit p21-Arc, complete cds | 2.219371653 |
| AW549040 | Rbmxrt | RNA binding motif protein, X chromosome retrogene | 2.218222838 |
| AW541478 | | ESTs, Highly similar to signal peptidase:SUBUNIT | 2.217423992 |
| AI447392 | Dgcr6 | DiGeorge syndrome chromosome region 6 | 2.216472345 |
| AW549381 | Rgds | ral guanine nucleotide dissociation stimulator | 2.21318416 |
| AU016133 | | ESTs, Weakly similar to MSSP [M. musculus] | 2.213009807 |
| AW537792 | Grp78 | glucose regulated protein, 78 kDa | 2.212760746 |
| AW551233 | Ptp4a2 | protein tyrosine phosphatase 4a2 | 2.212302179 |
| AW537568 | | ESTs, Weakly similar to similar to yeast heat shock protein STI1 [C. elegans] | 2.212010488 |
| AW550650 | Tctex1 | t-complex testis expressed 1 | 2.210463986 |
| AA016507 | Eif2ak4 | eukaryotic translation initiation factor 2 alpha kinase 4 | 2.209906084 |
| AA510877 | LOC56043 | aldo-keto reductase | 2.209674103 |
| AW556506 | | ESTs, Weakly similar to contains similarity to human cyclin A/CDK2-associated protein p19, an RNA polymerase II elongation factor-like protein [C. elegans] | 2.207942373 |
| AA033417 | Shd | src homology 2 domain-containing transforming protein D | 2.207103949 |
| AA270607 | HIRIP5 | HIRA-interacting protein 5 | 2.205698224 |
| AI447815 | | ESTs, Moderately similar to LUTHERAN BLOOD GROUP GLYCOPROTEIN PRECURSOR [H. sapiens] | 2.20379027 |
| AW536587 | Mkln1 | muskelin 1, intracellular mediator containing kelch motifs | 2.202865025 |
| AA427166 | | ESTs, Weakly similar to BAZF [M. musculus] | 2.202843556 |

SUPPLEMENTAL TABLE 4-continued

| Acc No | Gene | Description | N/F ratio |
|---|---|---|---|
| C80427 | | ESTs, Weakly similar to HYPOTHETICAL 32.0 KD PROTEIN IN SAP190-SPO14 INTERGENIC REGION [*Saccharomyces cerevisiae*] | 2.202416221 |
| AW537746 | Atp6k | ATPase, H+ transporting lysosomal (vacuolar proton pump), 9.2 kDa | 2.202077047 |
| AW554292 | Req | requiem | 2.199587912 |
| C76488 | Ubce7 | ubiquitin-conjugating enzyme 7 | 2.199583639 |
| W11665 | | ESTs, Highly similar to LEUCYL-TRNA SYNTHETASE, CYTOPLASMIC [*Saccharomyces cerevisiae*] | 2.199309009 |
| AW557050 | | ESTs, Highly similar to RADIAL SPOKE PROTEIN 3 [*Chlamydomonas reinhardtii*] | 2.198522495 |
| AI528531 | Pdha1 | Pyruvate dehydrogenase E1alpha subunit | 2.198483601 |
| AU023550 | Fin14 | fibroblast growth factor inducible 14 | 2.195941034 |
| W62248 | Cdh5 | cadherin 5 | 2.193808943 |
| AW536168 | Rangap1 | RAN GTPase activating protein 1 | 2.19351605 |
| AW554767 | Clk4 | CDC like kinase 4 | 2.190991173 |
| AA538228 | Rab25 | RAB25, member RAS oncogene family | 2.189550785 |
| AW546162 | | ESTs, Weakly similar to CARG-BINDING FACTOR-A [*M. musculus*] | 2.189482216 |
| AW539323 | | ESTs, Weakly similar to (defline not available 5852158) [*M. musculus*] | 2.189245581 |
| AU043933 | Gapd | glyceraldehyde-3-phosphate dehydrogenase | 2.189078854 |
| C77465 | | ESTs, Moderately similar to ZINC FINGER PROTEIN MLZ-4 [*Mus musculus*] | 2.188892377 |
| AW536852 | Fadk | focal adhesion kinase | 2.188786742 |
| AW536207 | | ESTs, Highly similar to TUBULIN BETA CHAIN [*Sus scrofa*] | 2.188517011 |
| W87197 | | ESTs, Highly similar to GLUTATHIONE S-TRANSFERASE P [*Homo sapiens*] | 2.188470627 |
| C79925 | Cox5a | cytochrome c oxidase, subunit Va | 2.187784867 |
| AI325926 | Pigf | Phosphatidylinositol glycan, class F | 2.18771481 |
| AW536073 | | ESTs, Weakly similar to cDNA EST yk338g10.5 comes from this gene [*C. elegans*] | 2.187551361 |
| AW555238 | | ESTs, Weakly similar to ORF YNL091w [*S. cerevisiae*] | 2.187097387 |
| AW546840 | | ESTs, Moderately similar to ubiquitin protein ligase [*M. musculus*] | 2.18669825 |
| AW544207 | Ubce4 | ubiquitin-conjugating enzyme 4 | 2.186399575 |
| W11957 | | Sm protein F [*H. sapiens*] | 2.185884275 |
| AA265845 | | *Mus musculus* mRNA for heterogeneous nuclear ribonucleoprotein H | 2.185702249 |
| C87751 | | *Mus musculus* sodium bicarbonate cotransporter isoform 3 kNBC-3 mRNA, complete | 2.185545754 |
| AW536982 | Syn1 | synapsin I | 2.18521333 |
| AA108797 | | ESTs, Highly similar to AF125100_1 HSPC039 protein [*H. sapiens*] | 2.185013011 |
| AU044169 | | ESTs, Weakly similar to TYROSINE-PROTEIN KINASE JAK3 [*M. musculus*] | 2.184892665 |
| AA105546 | | ESTs, Highly similar to CHROMOSOME REGION MAINTENANCE PROTEIN 1 [*Schizosaccharomyces pombe*] | 2.184752938 |
| AW536192 | | *Mus musculus* mRNA similar to human Sua1, complete cds | 2.184178135 |
| AW556780 | Cct3 | chaperonin subunit 3 (gamma) | 2.183029578 |
| AW552502 | | ESTs, Weakly similar to RHO GDP-DISSOCIATION INHIBITOR 2 [*M. musculus*] | 2.182648038 |
| AA517533 | Erf | Est2 repressor factor | 2.181963644 |
| AW546347 | | *Mus musculus* geminin mRNA, complete cds | 2.181899423 |
| AI414501 | | ESTs, Highly similar to citrin [*H. sapiens*] | 2.180840196 |
| AA521888 | Neo1 | neogenin | 2.180793589 |
| AW544317 | Psma6 | proteasome (prosome, macropain) subunit, alpha type 6 | 2.179852629 |
| AU019946 | | *Mus musculus* E2F-like transcriptional repressor protein mRNA, complete cds | 2.179418995 |
| AA050169 | Ppx | protein phosphatase X | 2.177816479 |
| AA111722 | Ccnd1 | cyclin D1 | 2.177805783 |
| W83655 | Prip | PPAR interacting protein PRIP | 2.177488026 |
| AA285673 | Rbmx | RNA binding motif protein, X chromosome | 2.17686901 |
| AA036275 | Gata1 | GATA-binding protein 1 | 2.176573242 |
| AW556431 | Krt2-1 | keratin complex 2, basic, gene 1 | 2.175571901 |
| AW536811 | H2afz | histone H2A.Z | 2.173945499 |
| C80066 | Hn1 | hematological and neurological expressed sequence 1 | 2.172659356 |
| W08432 | Brp44l | brain protein 44-like protein | 2.17256098 |
| C76660 | | ESTs, Moderately similar to KIAA0663 protein [*H. sapiens*] | 2.172287352 |
| C87299 | Csnk1e | casein kinase 1, epsilon | 2.167517796 |
| AW553712 | Ikbkb | inhibitor of kappa light polypeptide gene enhancer in B-cells, kinase beta | 2.166514209 |
| AU017536 | Cox6a1 | cytochrome c oxidase, subunit VI a, polypeptide 1 | 2.16607638 |
| AW544371 | Fin14 | fibroblast growth factor inducible 14 | 2.165438344 |
| W11746 | Tuba4 | tubulin alpha 4 | 2.164642273 |
| AU020791 | | Mouse mRNA for TI-225, complete cds | 2.164606896 |
| C77018 | G3bp2-pendin | ras-GTPase-activating protein (GAP<120>) SH3-domain-binding protein 2 | 2.164476129 |
| AU040132 | Shfdg1 | split hand/foot deleted gene 1 | 2.164347535 |
| AA275245 | | *Mus musculus* mRNA for vinculin, partial cds | 2.164119226 |
| AW547479 | | ESTs, Weakly similar to PERIPLASMIC DIVALENT CATION TOLERANCE PROTEIN CUTA [*Escherichia coli*] | 2.164045819 |
| AW537551 | Abcf3 | ATP-binding cassette, sub-family F (GCN20), member 3 | 2.163970346 |
| AI327284 | | ESTs, Highly similar to NADH-UBIQUINONE OXIDOREDUCTASE B15 SUBUNIT [*Bos taurus*] | 2.161072251 |
| AA182068 | | ESTs, Weakly similar to DEOXYRIBOSE-PHOSPHATE ALDOLASE [*Escherichia coli*] | 2.160741463 |
| AU020241 | Rps4x | ribosomal protein S4, X-linked | 2.160120787 |
| AW557678 | | ESTs, Moderately similar to CGI-147 protein [*H. sapiens*] | 2.15947136 |
| AW537744 | | *Mus musculus* protein inhibitor of activated STAT protein PIAS1 mRNA, complete cds | 2.159440423 |
| AW545312 | | *M. musculus* mRNA for GTP-binding protein | 2.159318938 |
| AW551617 | | ESTs, Weakly similar to HC1 ORF [*M. musculus*] | 2.157995583 |
| AW551441 | | *Mus musculus* carboxy terminus of Hsp70-interacting protein (Chip) mRNA, complete cds | 2.157761101 |

SUPPLEMENTAL TABLE 4-continued

| Acc No | Gene | Description | N/F ratio |
|---|---|---|---|
| AW552022 | Nudt5 | nudix (nucleoside diphosphate linked moiety X)-type motif 5 | 2.155260382 |
| AW549360 | Sfrs5 | splicing factor, arginine/serine-rich 5 (SRp40, HRS) | 2.154600128 |
| AW552668 | Lxn | latexin | 2.154541717 |
| AA204262 | | ESTs, Highly similar to ALPHA ENOLASE [*Mus musculus*] | 2.153653659 |
| AU021450 | | ESTs, Highly similar to step II splicing factor SLU7 [*H. sapiens*] | 2.153638703 |
| AI893442 | Cox6a1 | Cytochrome C oxidase, subunit VI a, polypeptide 1 | 2.152596602 |
| AW537050 | | ESTs, Moderately similar to HYPOTHETICAL 49.7 KD PROTEIN IN GIN2-STE3 INTERGENIC REGION [*Saccharomyces cerevisiae*] | 2.152451561 |
| W77190 | | ESTs, Weakly similar to 60S RIBOSOMAL PROTEIN L30A [*Saccharomyces cerevisiae*] | 2.151613671 |
| AA435101 | | ESTs, Highly similar to MDC-3.13 isoform 1 [*H. sapiens*] | 2.149988061 |
| AW556946 | | ESTs, Highly similar to TRANSCRIPTION INITIATION FACTOR IIF, ALPHA SUBUNIT [*Homo sapiens*] | 2.148972113 |
| AW554745 | | ESTs, Weakly similar to LA PROTEIN HOMOLOG [*Drosophila melanogaster*] | 2.148511594 |
| AW554784 | | ESTs, Weakly similar to Cxorf5 [*H. sapiens*] | 2.147980173 |
| AA057995 | | ESTs, Moderately similar to AF151892_1 CGI-134 protein [*H. sapiens*] | 2.147568646 |
| C85330 | | *Mus musculus* mRNA for aldolase C, partial | 2.146314267 |
| AW553718 | | *Mus musculus* CRIPT protein mRNA, complete cds | 2.146238796 |
| W98278 | | ESTs, Highly similar to AF161434_1 HSPC316 [*H. sapiens*] | 2.146162401 |
| C85794 | | ESTs, Weakly similar to myelin transcription factor 1-like [*M. musculus*] | 2.142786048 |
| AW553739 | Ttk | Ttk protein kinase | 2.14258919 |
| AA512757 | | ESTs, Weakly similar to cDNA EST EMBL; C08125 comes from this gene [*C. elegans*] | 2.139749244 |
| AW550795 | | ESTs, Highly similar to GUANINE NUCLEOTIDE-BINDING PROTEIN G(K), ALPHA SUBUNIT [*Rattus norvegicus*] | 2.137941679 |
| AU018994 | Atp5l | ATP synthase, H+ transporting, mitochondrial F0 complex, subunit g | 2.137180545 |
| AU040533 | | *Mus musculus* mRNA for mDj8, complete cds | 2.136122453 |
| AU043470 | | ESTs, Moderately similar to ubiquitin/60S ribosomal fusion protein [*M. musculus*] | 2.135402569 |
| AU041751 | Wbp2 | WW domain binding protein 2 | 2.13445614 |
| AU040781 | | *Mus musculus* ring-box protein 1 (Rbx1) mRNA, complete cds | 2.13360888 |
| AU040559 | Rpl3 | ribosomal protein L3 | 2.133597012 |
| AW546128 | Gli2 | GLI-Kruppel family member GLI2 | 2.133528553 |
| AU040711 | | ESTs, Weakly similar to All-1 protein + GTE form [*M. musculus*] | 2.132982988 |
| AW545556 | Rnps1 | ribonucleic acid binding protein S1 | 2.131229452 |
| AA386680 | Kif5b | kinesin family member 5B | 2.130805311 |
| AA276752 | | ESTs, Weakly similar to AF104033_1 MUEL protein [*M. musculus*] | 2.130751988 |
| AW536420 | Pfkl | phosphofructokinase, liver, B-type | 2.130381062 |
| AW537576 | Usf2 | upstream transcription factor 2 | 2.130169878 |
| AI324141 | Klc1 | Kinesin light chain 1 | 2.129968869 |
| AU023963 | | ESTs, Weakly similar to SIG41 [*M. musculus*] | 2.127150277 |
| W36959 | | ESTs, Weakly similar to AAKG_MOUSE 5'-AMP-ACTIVATED PROTEIN KINASE, GAMMA-1 SUBUNIT [*M. musculus*] | 2.126333607 |
| AA050135 | | ESTs, Highly similar to ISOCITRATE DEHYDROGENASE [*Bos taurus*] | 2.126317392 |
| AW537218 | | *Mus musculus* p53 apoptosis-associated target (Perp) mRNA, complete cds | 2.124913489 |
| AW554484 | Hnrpa2b1 | heterogenous nuclear ribonucleoprotein A2/B1 | 2.123621382 |
| AW551889 | Rnf4 | ring finger protein 4 | 2.123489733 |
| AU043672 | | ESTs, Highly similar to PUTATIVE ATP-DEPENDENT RNA HELICASE C22F3.08C [*Schizosaccharomyces pombe*] | 2.123346276 |
| AA183061 | | ESTs, Highly similar to RNA splicing-related protein [*R. norvegicus*] | 2.119535349 |
| C80708 | | ESTs, Weakly similar to 62D9.a [*D. melanogaster*] | 2.119484585 |
| W65230 | Cldn13 | claudin-13 gene | 2.119015454 |
| AA122896 | Slc22a11 | solute carrier family 22 (organic cation transporter), member 1-like | 2.118441117 |
| AU023882 | Brca2 | breast cancer 2 | 2.117866055 |
| AU019334 | | ESTs, Moderately similar to ACTIN-LIKE PROTEIN 14D [*Drosophila melanogaster*] | 2.117797328 |
| AW541501 | | ESTs, Highly similar to CLATHRIN HEAVY CHAIN [*Rattus norvegicus*] | 2.117485424 |
| AW557038 | | ESTs, Highly similar to TRANSCRIPTION INITIATION FACTOR TFIID 20/15 KD SUBUNIT [*H. sapiens*] | 2.116385548 |
| AW548472 | Rps8 | ribosomal protein S8 | 2.116104505 |
| AW540941 | | ESTs, Highly similar to CYTOCHROME C OXIDASE POLYPEPTIDE VIB [*Homo sapiens*] | 2.115464663 |
| AW545587 | | ESTs, Moderately similar to BIOTIN CARBOXYLASE [*Anabaena* pcc7120] | 2.112747687 |
| AW553979 | | ESTs, Highly similar to TYROSINE-PROTEIN KINASE JAK1 [*Homo sapiens*] | 2.11242201 |
| AW557096 | Nfix | nuclear factor I/X | 2.1119444 |
| AU044022 | | ESTs, Weakly similar to predicted using Genefinder [*C. elegans*] | 2.111675482 |
| AW550624 | | Mouse mRNA for TI-225, complete cds | 2.110955467 |
| AI415012 | | ESTs, Weakly similar to F25H9.7 [*C. elegans*] | 2.110875235 |
| AA003927 | Cct2 | chaperonin subunit 2 (beta) | 2.110823315 |
| W89599 | Eif2s3x | eukaryotic translation initiation factor 2, subunit 3, structural gene X-linked | 2.109036647 |
| AW549119 | RIE2 | RIE2 protein | 2.108802 |
| AA027675 | Tbx15 | T-box 15 | 2.107485233 |
| AW555686 | | ESTs, Moderately similar to FAD SYNTHETASE [*Saccharomyces cerevisiae*] | 2.107160343 |
| AW536333 | Tcfl1 | transcription factor-like 1 | 2.105768299 |
| AU015203 | Pttg1 | pituitary tumor-transforming 1 | 2.10557106 |
| W34455 | | ESTs, Highly similar to NADH-UBIQUINONE OXIDOREDUCTASE B12 SUBUNIT [*Bos taurus*] | 2.105042587 |
| AU041434 | Ulk1 | Unc-51 like kinase 1 (*C. elegans*) | 2.103857568 |
| AU017038 | | ESTs, Highly similar to REPLICATION PROTEIN A 14 KD SUBUNIT [*Homo sapiens*] | 2.102934707 |
| W14837 | Prsc1 | protease, cysteine, 1 | 2.102744346 |
| AA163432 | | ESTs, Weakly similar to ANX7_MOUSE ANNEXIN VII [*M. musculus*] | 2.102354444 |

SUPPLEMENTAL TABLE 4-continued

| Acc No | Gene | Description | N/F ratio |
|---|---|---|---|
| AW544350 | | ESTs, Highly similar to ESS1 PROTEIN [*Saccharomyces cerevisiae*] | 2.101933004 |
| AU018835 | | *Mus musculus* claudin-10 mRNA, complete cds | 2.101785421 |
| AA415519 | | ESTs, Weakly similar to HYPOTHETICAL 40.4 KD PROTEIN R06F6.5 IN CHROMOSOME II [*Caenorhabditis elegans*] | 2.101349422 |
| AW538436 | | *Mus musculus* protein inhibitor of nitric oxide synthase (PIN) mRNA, complete cds | 2.100694954 |
| AA086829 | Mssk1 | muscle-specific serine kinase 1 | 2.100087115 |
| AA212445 | Stat5a | Signal transducer and activator of transcription 5A | 2.099472632 |
| AW555798 | Ncor1 | nuclear receptor co-repressor 1 | 2.098583834 |
| AU041141 | | ESTs, Moderately similar to (defline not available 6118541) [*M. musculus*] | 2.097620163 |
| AA272878 | | ESTs, Highly similar to atypical PKC specific binding protein [*R. norvegicus*] | 2.09748684 |
| AA014127 | D15Wsu77e | DNA segment, Chr 15, Wayne State University 77, expressed | 2.094998947 |
| AW544533 | Tk1 | thymidine kinase 1 | 2.093696405 |
| AI528532 | | *Mus musculus* protein kinase C inhibitor (mPKCI) mRNA, complete cds | 2.093394542 |
| AU040509 | | ESTs, Weakly similar to Ring3 [*M. musculus*] | 2.092999984 |
| AA049416 | His1a | histone H1 | 2.092964075 |
| AA268862 | Saps-pending | SKAP55 homologue | 2.092899653 |
| C88157 | | *Mus musculus* RING finger protein AO7 mRNA, complete cds | 2.092505596 |
| AW536161 | Ftl1 | ferritin light chain 1 | 2.092408097 |
| AA032709 | D7Ertd462e | DNA segment, Chr 7, ERATO Doi 462, expressed | 2.091456089 |
| AW538753 | | ESTs, Highly similar to SORCIN [*Cricetulus longicaudatus*] | 2.090595934 |
| AW554607 | Ptk9r-pending | protein tyrosine kinase 9 related protein | 2.088525057 |
| AI325946 | | TESTIN 2 PRECURSOR | 2.088224301 |
| AW550148 | Spint2 | serine protease inhibitor, Kunitz type 2 | 2.088199037 |
| AW555109 | Chd1 | chromodomain helicase DNA binding protein 1 | 2.088170924 |
| AW557266 | | ESTs, Highly similar to MITOCHONDRIAL IMPORT RECEPTOR SUBUNIT TOM20 HOMOLOG [*R. norvegicus*] | 2.085963328 |
| AW538548 | | ESTs, Highly similar to PHOSPHATIDYLSERINE DECARBOXYLASE PROENZYME [*Cricetulus griseus*] | 2.085827569 |
| AW552438 | | ESTs, Moderately similar to (defline not available 5714400) [*M. musculus*] | 2.084900792 |
| AA413090 | | ESTs, Moderately similar to unknown protein IT12 [*H. sapiens*] | 2.08408988 |
| AI573427 | Catnb | Catenin beta | 2.08164667 |
| AW551843 | | ESTs, Highly similar to (defline not available 5901572) [*R. norvegicus*] | 2.081031756 |
| AW549786 | Atp5b | ATP synthase, H+ transporting mitochondrial F1 complex, alpha subunit | 2.080499984 |
| AW555377 | Ahcy | S-adenosylhomocysteine hydrolase | 2.080387755 |
| AW545836 | | ESTs, Highly similar to GLUCOSE-6-PHOSPHATASE [*Homo sapiens*] | 2.07946168 |
| AW554408 | Usp9x | ubiquitin specific protease 9, X chromosome | 2.079410205 |
| AU017036 | | ESTs, Highly similar to UBIQUITIN-CONJUGATING ENZYME E2-17 KD 3 [*Homo sapiens; Rattus norvegicus*] | 2.0788242 |
| AU023795 | | ESTs, Weakly similar to formin binding protein 11 [*M. musculus*] | 2.078771795 |
| AU021910 | | ESTs, Highly similar to C-1 [*H. sapiens*] | 2.078299566 |
| AA066209 | | *M. musculus* mRNA for glutamyl-tRNA synthetase | 2.078220839 |
| AA028539 | Pdgfc | platelet-derived growth factor, C polypeptide | 2.078034358 |
| AW545810 | | ESTs, Highly similar to P53-BINDING PROTEIN 53BP2 [*M. musculus*] | 2.077868917 |
| AW543954 | Ubl1 | ubiquitin-like 1 | 2.077687345 |
| AU015235 | | *Mus musculus* pre-B-cell colony-enhancing factor mRNA, complete cds | 2.077221503 |
| AI450292 | | ESTs, Highly similar to signal peptidase:SUBUNIT | 2.077147229 |
| AU021030 | | *Mus musculus* mACS4 mRNA for Acyl-CoA synthetase 4, complete cds | 2.076973921 |
| AW548833 | | ESTs, Weakly similar to coronin-3 [*M. musculus*] | 2.076920083 |
| AA241780 | Atp6s1 | ATPase, H+ transporting, lysosomal (vacuolar proton pump), subunit 1 | 2.074155421 |
| AU015646 | Rex3 | reduced expression 3 | 2.071644406 |
| W34672 | Sh3d2a | SH3 domain protein 2A | 2.071075902 |
| AU041272 | | ESTs, Weakly similar to cDNA EST EMBL:C08125 comes from this gene [*C. elegans*] | 2.07070659 |
| AW556256 | Tcfcp2 | transcription factor CP2 | 2.070422069 |
| AI465224 | | ESTs, Highly similar to 60S RIBOSOMAL PROTEIN L15 [*Rattus norvegicus*] | 2.06998501 |
| AW555326 | Smoh | smoothened homolog (*Drosophila*) | 2.069871303 |
| AU042878 | Psmc3Ip | proteasome (prosome, macropain) 26S subunit, ATPase 3, interacting protein | 2.069863024 |
| C78336 | Cnn2 | calponin 2 | 2.068042036 |
| AW545645 | Tpm5 | tropomyosin 5 | 2.067947872 |
| AW551315 | Rps29 | ribosomal protein S29 | 2.067794525 |
| AI428885 | | ESTs, Weakly similar to /prediction | 2.066416765 |
| AW536068 | Rrm1 | ribonucleotide reductase M1 | 2.066220888 |
| AI323636 | | *Mus musculus* eosinophil secondary granule protein (mEAR-2) mRNA, complete cds | 2.065726689 |
| AU042101 | Plp | proteolipid protein (myelin) | 2.065430884 |
| C77213 | | ESTs, Moderately similar to PUTATIVE ORAL CANCER SUPPRESSOR [*Mesocricetus auratus*] | 2.065210238 |
| AU023139 | | ESTs, Weakly similar to natural killer cell tumor-recognition protein [*M. musculus*] | 2.061470989 |
| AW536843 | Cct4 | chaperonin subunit 4 (delta) | 2.060855635 |
| AA221877 | | ESTs, Highly similar to GUAA_HUMAN GMP SYNTHASE [*H. sapiens*] | 2.060478391 |
| AU019894 | | ESTs, Highly similar to brain and reproductive organ-expressed protein [*H. sapiens*] | 2.059614762 |
| W59026 | | KIAA0857 | 2.05813772 |
| AU042518 | Hdc | histidine decarboxylase cluster | 2.056638675 |
| AW546468 | | ESTs, Highly similar to RIBONUCLEASE INHIBITOR [*Rattus norvegicus*] | 2.055993345 |
| AW536183 | Cct3 | chaperonin subunit 3 (gamma) | 2.05541031 |
| AI326287 | | ESTs, Highly similar to TUBULIN ALPHA-4 CHAIN [*Gallus gallus*] | 2.054481753 |
| AW551916 | | *Mus musculus* putative deubiquitinating enzyme UBPY (Ubpy) mRNA, complete cds | 2.054332813 |

SUPPLEMENTAL TABLE 4-continued

| Acc No | Gene | Description | N/F ratio |
|---|---|---|---|
| AW536647 | | ESTs, Highly similar to HYPOTHETICAL 25.7 KD PROTEIN IN MSH1-EPT1 INTERGENIC REGION [*Saccharomyces cerevisiae*] | 2.053538694 |
| AW556964 | Silg41 | silica-induced gene 41 | 2.05313114 |
| AW537469 | | ESTs, Moderately similar to BB1 | 2.052267636 |
| AU017931 | | ESTs, Highly similar to ALPHA-1,6-MANNOSYL-GLYCOPROTEIN BETA-1,2-N-ACETYLGLUCOSAMINYLTRANSFERASE [*Rattus norvegicus*] | 2.050617842 |
| AW542919 | | ESTs, Highly similar to KIAA0398 [*H. sapiens*] | 2.049586337 |
| AW547284 | | ESTs, Weakly similar to PYRROLINE-5-CARBOXYLATE REDUCTASE [*Glycine max*] | 2.049181802 |
| C88181 | | ESTs, Moderately similar to CCR4-ASSOCIATED FACTOR 1 [*M. musculus*] | 2.049163559 |
| C85992 | Tnni2 | troponin I, skeletal, fast 2 | 2.046590193 |
| AA124929 | | ESTs, Moderately similar to unnamed protein product [*H. sapiens*] | 2.046014815 |
| AA031105 | | ESTs, Weakly similar to nuclear protein ZAP [*M. musculus*] | 2.0462411 |
| AW547298 | | ESTs, Weakly similar to NG38 [*M. musculus*] | 2.045099916 |
| AW544241 | | ESTs, Highly similar to eukaryotic translation initiation factor eIF3, p35 subunit [*H. sapiens*] | 2.043937442 |
| AA542348 | | ESTs, Weakly similar to SIK similar protein [*M. musculus*] | 2.043764446 |
| AA030810 | | ESTs, Highly similar to AF161432_1 HSPC314 [*H. sapiens*] | 2.043627079 |
| AA273426 | | ESTs, Moderately similar to nebulette [*H. sapiens*] | 2.043366784 |
| AI447370 | | ESTs, Highly similar to CAAX prenyl protein protease RCE1 [*H. sapiens*] | 2.04179856 |
| AA087193 | Lcn2 | Lipocalin 2 | 2.040902926 |
| AW552069 | Atp5f1 | ATP synthase, H+ transporting, mitochondrial F0 complex, subunit b, isoform 1 | 2.040618398 |
| AW554249 | | ESTs, Weakly similar to microtubule-actin crosslinking factor [*M. musculus*] | 2.040394297 |
| AW552221 | Hdgf | hepatoma-derived growth factor | 2.039626815 |
| AW547185 | Arg1 | arginase 1, liver | 2.037574557 |
| AU020575 | | ESTs, Moderately similar to HYPOTHETICAL 27.1 KD PROTEIN CCE1-CAP1 INTERGENIC REGION [*Saccharomyces cerevisiae*] | 2.037569931 |
| AW545291 | Calm | calmodulin | 2.037514948 |
| AU020225 | | *Mus musculus* mRNA for Sid393p, complete cds | 2.037396367 |
| AW556673 | Anxa7 | annexin A7 | 2.036952459 |
| W14928 | Smpd1 | Sphingomyelin phosphodiesterase 1, acid lysosomal | 2.035892157 |
| AU045064 | | ESTs, Highly similar to SOH1 PROTEIN [*Saccharomyces cerevisiae*] | 2.035291187 |
| AU015736 | | ESTs, Moderately similar to KIAA0873 protein [*H. sapiens*] | 2.035101764 |
| AW554127 | Ly84l | lymphocyte antigen 84 ligand | 2.033282134 |
| AI893564 | Anx5 | Annexin V | 2.032674021 |
| AI414985 | | ESTs, Highly similar to HYPOTHETICAL 109.5 KD PROTEIN IN PPA1-DAP2 INTERGENIC REGION [*Saccharomyces cerevisiae*] | 2.032638418 |
| AW536161 | Ftl1 | ferritin light chain 1 | 2.031483082 |
| AW557154 | | ESTs, Highly similar to HYPOTHETICAL 64.5 KD PROTEIN ZK652.9 IN CHROMOSOME III [*Caenorhabditis elegans*] | 2.030895392 |
| AW544402 | | ESTs, Moderately similar to PROBABLE UBIQUITIN CARBOXYL-TERMINAL HYDROLASE [*Mus musculus*] | 2.028946654 |
| AA058194 | Ephb1 | Eph receptor B1 | 2.028898148 |
| AW538460 | Sfrs3 | splicing factor, arginine/serine-rich 3 (SRp20) | 2.027993079 |
| AU018866 | Abcd3 | ATP-binding cassette, sub-family D (ALD), member 3 | 2.027886388 |
| W89491 | Fus2 | fusion 2 (human) | 2.027721104 |
| AW556539 | | *Mus musculus* mRNA for eIF3 p66, complete cds | 2.026302738 |
| W63009 | D6Wsu137e | DNA segment, Chr 6, Wayne State University 137, expressed | 2.026028375 |
| AA467238 | | ESTs, Moderately similar to AF155107_1 NY-REN-37 antigen [*H. sapiens*] | 2.025843113 |
| W79958 | Xnp | X-linked nuclear protein | 2.025191263 |
| AU019848 | Ldb1 | LIM domain binding 1 | 2.024274047 |
| AA220582 | Cyp2f2 | Cytochrome P450, 2f2 | 2.023391931 |
| C76118 | | *Mus musculus* carboxy terminus of Hsp70-interacting protein (Chip) mRNA, complete cds | 2.022613159 |
| AA016824 | Cck | cholecystokinin | 2.022490481 |
| AI326325 | | ESTs, Weakly similar to CCAAT-BINDING TRANSCRIPTION FACTOR SUBUNIT A [*Petromyzon marinus*] | 2.020679018 |
| AA253928 | S100a11 | S100 calcium binding protein A11 | 2.019696914 |
| AW541485 | Ldlr | low density lipoprotein receptor | 2.019565667 |
| AW536904 | Ppia | peptidylprolyl isomerase A | 2.019439841 |
| AW552486 | Ube2i | ubiquitin-conjugating enzyme E2I | 2.018883876 |
| AU041740 | | *M. musculus* mRNA for fibromodulin | 2.01868023 |
| AI448352 | | ESTs, Highly similar to KIAA0670 protein [*H. sapiens*] | 2.018648182 |
| AW557886 | | ESTs, Highly similar to dJ30M3.2 [*H. sapiens*] | 2.018168191 |
| AW546615 | | ESTs, Highly similar to TRANSLATIONAL INITIATION FACTOR 2 ALPHA SUBUNIT [*Rattus norvegicus; Bos taurus*] | 2.017143269 |
| AW536942 | | *Mus musculus* mRNA for MSSP, complete cds | 2.017088183 |
| AU017987 | | ESTs, Weakly similar to NADH-CYTOCHROME B5 REDUCTASE [*R. norvegicus*] | 2.016928064 |
| C85531 | | *Mus musculus* TBX1 protein mRNA, complete cds | 2.016803084 |
| AW545339 | Ate1 | arginine-tRNA-protein transferase 1 | 2.016693199 |
| AW546437 | Rab6kifl | Rab6, kinesin-like | 2.016652063 |
| AI666581 | | RIBOSOMAL PROTEIN S6 KINASE II ALPHA 1 | 2.016029612 |
| AI447773 | | *Mus musculus* BAF53a (Baf53a) mRNA, complete cds | 2.015349198 |
| AA537763 | | matrin cyclophilin (matrin-cyp) [*R. rattus*] | 2.014990505 |
| AA030846 | Coq7 | demethyl-Q 7 | 2.013748884 |
| AW537679 | | ESTs, Highly similar to transcriptional co-activator CRSP77 [*H. sapiens*] | 2.012445473 |
| AW545196 | Sui1-rs1 | suppressor of initiator codon mutations, related sequence 1 (*S. cerevise*) | 2.012217503 |
| C78825 | | ESTs, Weakly similar to protein co-factor [*M. musculus*] | 2.011284548 |

SUPPLEMENTAL TABLE 4-continued

| Acc No | Gene | Description | N/F ratio |
|---|---|---|---|
| AW551014 | | ESTs, Highly similar to KIAA0594 protein [*H. sapiens*] | 2.011053628 |
| AW550287 | Map2k7 | mitogen activated protein kinase kinase 7 | 2.010008679 |
| C79872 | Psmd7 | proteasome (prosome, macropain) 26S subunit, non-ATPase, 7 | 2.009904416 |
| AW538975 | | ESTs, Weakly similar to ladinin [*H. sapiens*] | 2.009401476 |
| AI666784 | | ESTs, Weakly similar to protein kinase C-binding protein RACK7 [*H. sapiens*] | 2.00819018 |
| C79697 | Phgdh | 3-phosphoglycerate dehydrogenase | 2.00734278 |
| AW536784 | | ESTs, Weakly similar to HYPOTHETICAL PROTEIN KIAA0174 [*H. sapiens*] | 2.005216822 |
| AW552691 | | ESTs, Highly similar to KINESIN-II 85 KD SUBUNIT [*Strongylocentrotus purpuratus*] | 2.004947093 |
| W66889 | | ESTs, Highly similar to RABPHILIN-3A [*Rattus norvegicus*] | 2.004938025 |
| AW553280 | Itgb1 | integrin beta 1 (fibronectin receptor beta) | 2.003708956 |
| AI413372 | | ESTs, Highly similar to Rer1 protein [*H. sapiens*] | 2.003211999 |
| C77965 | Fgfrp | fibroblast growth factor regulated protein | 2.00177749 |
| AA153905 | | ESTs, Weakly similar to CG17019 gene product [*D. melanogaster*] | 2.000439106 |
| AW544501 | Hmox1 | heme oxygenase (decycling) 1 | 0.498585892 |
| W62969 | Fyn | Fyn protooncogene | 0.498473008 |
| AW547534 | Snrp116-pending | U5 small nuclear ribonucleoprotein 116 kDa | 0.497942009 |
| AW556002 | | ESTs, Weakly similar to open reading frame [*M. musculus*] | 0.497906318 |
| AW538495 | | ESTs, Moderately similar to GLYCOPROTEIN 25L PRECURSOR [*Canis familiaris*] | 0.497505758 |
| AU018809 | | ESTs, Weakly similar to cDNA EST EMBL:D70762 comes from this gene [*C. elegans*] | 0.497360848 |
| W34685 | Rora | RAR-related orphan receptor alpha | 0.496667567 |
| AI426288 | | ESTs, Weakly similar to ultra-high-sulfur keratin [*M. musculus*] | 0.496141712 |
| AI324866 | | *Mus musculus* PEST phosphatase interacting protein mRNA, complete cds | 0.495826245 |
| AI893650 | Usf2 | Upstream transcription factor 2 | 0.49557731 |
| AI426736 | | *Mus musculus* timeless homolog mRNA, complete cds | 0.494513325 |
| AA184214 | Gabpb1 | GA repeat binding protein, beta 1 | 0.494022907 |
| AA017867 | | ESTs, Highly similar to CARCINOEMBRYONIC ANTIGEN CGM6 PRECURSOR [*Homo sapiens*] | 0.493125955 |
| AA268219 | Mpeg1 | macrophage expressed gene 1 | 0.492580225 |
| AA239856 | Omi | serine protease OMI | 0.492467109 |
| W16354 | | ESTs, Moderately similar to LAR PROTEIN PRECURSOR [*Homo sapiens*] | 0.491968272 |
| C87660 | | ESTs, Weakly similar to melastatin [*M. musculus*] | 0.491744995 |
| AW555781 | C1qb | complement component 1, q subcomponent, beta polypeptide | 0.490941625 |
| AI428004 | | ESTs, Moderately similar to transporter protein [*H. sapiens*] | 0.489481805 |
| C77865 | | ESTs, Highly similar to major vault protein [*R. norvegicus*] | 0.488832841 |
| AI449541 | | ESTs, Highly similar to myc far upstream element-binding protein [*H. sapiens*] | 0.488201357 |
| W64937 | Arp2-pending | angiopoietin related protein 2 | 0.486616378 |
| AI327367 | Cd28 | CD28 antigen | 0.486573305 |
| AA413761 | Epn2 | epsin2 | 0.48638791 |
| AA511061 | | ESTs, Weakly similar to similar to kinensin-like protein [*C. elegans*] | 0.485798066 |
| AA462869 | C2 | Complement component 2 (within H-2S) | 0.485770605 |
| W30178 | | Platelet derived growth factoralpha | 0.485512789 |
| AW536657 | | ESTs, Highly similar to PHOSPHOENOLPYRUVATE CARBOXYKINASE, CYTOSOLIC [*Rattus norvegicus*] | 0.484491052 |
| C81284 | | ESTs, Moderately similar to TYROSINE-PROTEIN KINASE JAK2 [*M. musculus*] | 0.484285289 |
| AI661346 | | ESTs, Moderately similar to estradiol 17beta-dehydrogenase [*M. musculus*] | 0.484253534 |
| AA064183 | Pex16 | peroxisome biogenesis factor 16 | 0.483919369 |
| AI385600 | | *Mus musculus* cyclic nucleotide phosphodiesterase (PDE1A2) mRNA, complete cds | 0.48335782 |
| AI447349 | | ESTs, Moderately similar to hypothetical protein [*H. sapiens*] | 0.483147225 |
| AU045766 | | ESTs, Weakly similar to KIAA0926 protein [*H. sapiens*] | 0.482947335 |
| AA174729 | D13Ertd275e | DNA segment, Chr 13, ERATO Doi 275, expressed | 0.482851894 |
| W82220 | Rab3a | RAB3A, member RAS oncogene family | 0.482386856 |
| AI447993 | H2-Aa | Histocompatibility 2, class II antigen A, alpha | 0.48129597 |
| AI327389 | Stat4 | Signal transducer and activator of transcription 4 | 0.481241844 |
| AI427715 | | ESTs, Weakly similar to Rab8-interacting protein [*M. musculus*] | 0.481160908 |
| AI449408 | | RADIXIN | 0.48100611 |
| AA014942 | | ESTs, Weakly similar to RAS-like protein expressed in many tissues [*M. musculus*] | 0.480372777 |
| AA000726 | Vipr2 | Vasoactive intestinal peptide receptor 2 | 0.480224921 |
| C81465 | Taut | taurine/beta-alanine transporter | 0.479566248 |
| AI425920 | | ESTs, Weakly similar to HSPC010 [*H. sapiens*] | 0.479378243 |
| C77369 | | ESTs, Weakly similar to cDNA EST EMBL:C11678 comes from this gene [*C. elegans*] | 0.47922836 |
| C88320 | | ESTs, Weakly similar to RING1B protein [*M. musculus*] | 0.47820664 |
| AU040253 | | ESTs, Weakly similar to LR8 [*M. musculus*] | 0.47742886 |
| AA260747 | Birc6 | baculoviral IAP repeat-containing 6 | 0.476766539 |
| AW544351 | Kifap3 | kinesin-associated protein 3 | 0.476693505 |
| AU041202 | | *Mus musculus* mRNA, complete cds, clone: 2-68 | 0.475319304 |
| AU020028 | Ier5 | immediate early response 5 | 0.475163983 |
| AI413118 | Gng3lg | G protein gamma 3 linked gene | 0.473543339 |
| AA061278 | | ESTs, Weakly similar to KIAA0308 [*H. sapiens*] | 0.473431725 |
| AU014897 | Apc | adenomatosis polyposis coli | 0.472956452 |
| AA426926 | D14Ertd817e | DNA segment, Chr 14, ERATO Doi 817, expressed | 0.472580007 |
| AA108640 | Gdc1 | Glycerolphosphate dehydrogenase 1, cytoplasmic adult | 0.4722026 |
| AA261368 | Ywhaz | tyrosine 3-monooxygenase/tryptophan 5-monooxygenase activation protein, zeta polypeptide | 0.471958974 |
| AA435123 | | ESTs, Weakly similar to ZK1058.5 [*C. elegans*] | 0.471909449 |
| AU043840 | Ccr4 | carbon catabolite repression 4 homolog (*S. cerevisiae*) | 0.471612261 |
| AI450156 | | ESTs, Weakly similar to RING1B protein [*M. musculus*] | 0.470602473 |

SUPPLEMENTAL TABLE 4-continued

| Acc No | Gene | Description | N/F ratio |
|---|---|---|---|
| AW536169 | Sparc | secreted acidic cysteine rich glycoprotein | 0.468881114 |
| AW552818 | | *M. musculus* mRNA for GTP-binding protein | 0.466979012 |
| C77414 | Gpcr26 | G-protein coupled receptor 26 | 0.466353125 |
| AI449065 | | ESTs, Highly similar to SUSHI REPEAT-CONTAINING PROTEIN SRPX PRECURSOR [*R. norvegicus*] | 0.4658412 |
| AA260521 | Ucp2 | uncoupling protein 2, mitochondrial | 0.465029569 |
| AA200091 | | ESTs, Moderately similar to AF096286_1 pecanex 1 [*M. musculus*] | 0.46491171 |
| AI326894 | | ESTs, Moderately similar to HYPOTHETICAL 20.8 KD PROTEIN T09A5.6 IN CHROMOSOME III [*Caenorhabditis elegans*] | 0.46346233 |
| AA118392 | Staf | selenocysteine tRNA gene transcription activating factor | 0.460978805 |
| AA200942 | Slfn4 | schlafen 4 | 0.460594202 |
| AA275985 | | Rieske iron-sulfur protein [*R. Rattus*] | 0.459911898 |
| AI325975 | | ESTs, Highly similar to 65 KD YES-ASSOCIATED PROTEIN [*Mus musculus*] | 0.459243061 |
| AI323966 | | ESTs, Weakly similar to GOLIATH PROTEIN [*Drosophila melanogaster*] | 0.458644321 |
| W12425 | | ESTs, Highly similar to KIAA1533 protein [*H. sapiens*] | 0.457391655 |
| W81912 | Crabp2 | Cellular retinoic acid binding protein II | 0.457211976 |
| AA178121 | Ctss | cathepsin S | 0.457173001 |
| W70924 | | PK-120 precursor (itih-4) | 0.456587824 |
| AA123853 | Cast | calpastatin | 0.456342311 |
| AA230451 | S100a8 | S100 calcium binding protein A8 (calgranulin A) | 0.456297242 |
| AI430926 | | ESTs, Highly similar to KIAA1002 protein [*H. sapiens*] | 0.455164376 |
| W97303 | Meg3 | maternally expressed gene 3 | 0.454711379 |
| AI426555 | | *Mus musculus* histone deacetylase mHDA1 mRNA, complete cds | 0.454390478 |
| AA061732 | shrm | shroom | 0.45390698 |
| AU020551 | | ESTs, Moderately similar to NOF1 [*H. sapiens*] | 0.45336961 |
| AI429678 | Capn5 | Calpain 5 | 0.452911351 |
| AA213015 | Tstap35b | tissue specific transplantation antigen P35B | 0.452689264 |
| AU018982 | C1s | complement component 1, s subcomponent | 0.451660309 |
| AA268592 | Tgfbi | Transforming growth factor, beta induced, 68 kDa | 0.451233977 |
| C79673 | | ESTs, Weakly similar to TALIN [*M. musculus*] | 0.451086496 |
| AU019876 | | ESTs, Moderately similar to POLLEN SPECIFIC PROTEIN SF3 [*Helianthus annuus*] | 0.450242321 |
| W29855 | ep | Pale ear | 0.450183821 |
| AI325516 | | ESTs, Highly similar to ASPARTOACYLASE [*Homo sapiens*] | 0.449831178 |
| AU016285 | Unc5h3 | UNC-5 homolog (*C. elegans*) 3 | 0.449107031 |
| C81338 | Col5a1 | procollagen, type V, alpha 1 | 0.4484605 |
| AA120639 | D13Ertd372e | DNA segment, Chr 13, ERATO Doi 372, expressed | 0.447735968 |
| AI452234 | | ESTs, Weakly similar to Similar to aldehyde dehydrogenase [*C. elegans*] | 0.447667176 |
| AA073843 | | ESTs, Weakly similar to HYPOTHETICAL 29.5 KD PROTEIN C05B5.7 IN CHROMOSOME III [*Caenorhabditis elegans*] | 0.446317848 |
| AA189196 | | ESTs, Highly similar to T00325 hypothetical protein KIAA0546 - human [*H. sapiens*] | 0.446285677 |
| AA118626 | | ESTs, Highly similar to unnamed protein product [*H. sapiens*] | 0.445541417 |
| AI528706 | | *Mus musculus* MPS1 gene and mRNA, 3'end | 0.443511276 |
| AI324761 | | *Mus musculus* short-chain dehydrogenase CRAD2 mRNA, complete cds | 0.442839884 |
| W99968 | Kcnn4 | potassium intermediate/small conductance calcium-activated channel, subfamily N, member 4 | 0.441371237 |
| AA435060 | Lst1 | leucocyte specific transcript 1 | 0.441296333 |
| AA178076 | Cd53 | CD53 antigen | 0.440591878 |
| AU041801 | Drr3 | developmentally regulated repeat element-containing transcript 3 | 0.439266461 |
| AU019411 | | ESTs, Highly similar to ARGININOSUCCINATE LYASE [*Homo sapiens*] | 0.438910556 |
| AI326924 | | ESTs, Highly similar to MYO-INOSITOL-1(OR 4)-MONOPHOSPHATASE [*Xenopus laevis*] | 0.43795106 |
| AI450850 | | ESTs, Highly similar to 0-44 PROTEIN [*Rattus norvegicus*] | 0.43692673 |
| AA120432 | | *Mus musculus* prostaglandin transporter PGT mRNA, complete cds | 0.436751727 |
| AA110278 | | ESTs, Weakly similar to unknown [*R. norvegicus*] | 0.43638582 |
| AU042856 | | ESTs, Weakly similar to contains similarity to *Saccharomyces cerevisiae* MAF1 protein [*C. elegans*] | 0.43622857 |
| AA003252 | Myhca | myosin heavy chain, cardiac muscle, adult | 0.434973545 |
| AW546079 | | ESTs, Highly similar to HYPOTHETICAL 70.2 KD PROTEIN IN GSH1-CHS6 INTERGENIC REGION [*Saccharomyces cerevisiae*] | 0.434243151 |
| C79931 | jmj | jumonji | 0.430266963 |
| AI451309 | Plxn3 | Plexin 3 | 0.430074817 |
| AI426259 | | ESTs, Weakly similar to high affinity immunoglobulin gamma Fc receptor I [*M. musculus*] | 0.429035689 |
| AA474849 | | ESTs, Highly similar to KIAA1461 protein [*H. sapiens*] | 0.42741177 |
| W82668 | Spry1 | sprouty homolog 1 (*Drosophila*) | 0.426418559 |
| AA161816 | Api5 | apoptosis inhibitory protein 5 | 0.425689953 |
| AI323807 | | *Mus musculus* GDP-dissociation inhibitor mRNA, preferentially expressed in hematopoietic cells, complete cds | 0.423803111 |
| AA118878 | | ESTs, Highly similar to NEDD-4 PROTEIN [*Homo sapiens*] | 0.423726623 |
| AA212838 | Psmb7 | Proteasome (prosome, macropain) subunit, beta type 7 | 0.42279869 |
| W46125 | | ESTs, Weakly similar to D29149 proline-rich protein - mouse [*M. musculus*] | 0.422389477 |
| AA144383 | Clpx | caseinolytic protease X (*E. coli*) | 0.422311709 |
| AI385657 | Ext1 | Exostoses (multiple) 1 | 0.417206887 |
| C86591 | Sdfr2 | stromal cell derived factor receptor 2 | 0.415674914 |
| AU042151 | | ESTs, Highly similar to laminin B1 [*M. musculus*] | 0.412353937 |
| AI324011 | | ESTs, Weakly similar to BRAIN SPECIFIC POLYPEPTIDE PEP-19 [*Rattus norvegicus*; *Mus musculus*] | 0.411873664 |

SUPPLEMENTAL TABLE 4-continued

| Acc No | Gene | Description | N/F ratio |
|---|---|---|---|
| AI451431 | | ESTs, Highly similar to RAS-RELATED PROTEIN RAL-B [*Rattus norvegicus*] | 0.410550864 |
| AA175990 | | ESTs, Highly similar to P300_HUMAN E1A-ASSOCIATED PROTEIN P300 [*H. sapiens*] | 0.41013035 |
| AA250039 | Lgals9 | lectin, galactose binding, soluble 9 | 0.409511422 |
| AI326849 | | TRANSCRIPTIONAL REGULATOR PROTEIN HCNGP | 0.406388099 |
| C79775 | Hba-a1 | hemoglobin alpha, adult chain 1 | 0.40598605 |
| C77913 | Gdf3 | growth differentiation factor 3 | 0.404203495 |
| C77459 | | ESTs, Weakly similar to HYPOTHETICAL PROTEIN KIAA0008 [*H. sapiens*] | 0.404184781 |
| AW557391 | Nedd5 | neural precursor cell expressed, developmentally down-regulated gene 5 | 0.403827774 |
| AU018863 | Klf4 | Kruppel-like factor 4 (gut) | 0.403065274 |
| AU042260 | Cfi | complement component factor I | 0.402491799 |
| W34157 | | Secreted acidic cysteine rich glycoprotein SPARC | 0.401851169 |
| AA178132 | | *Mus musculus* PGES mRNA for prostaglandin E synthase, complete cds | 0.401791284 |
| W08086 | Gba | Acid beta glucosidase | 0.401380464 |
| AA250238 | Usp18 | ubiquitin specific protease 18 | 0.401098929 |
| AA048539 | | ESTs, Highly similar to INOSITOL 1,4,5-TRISPHOSPHATE-BINDING PROTEIN TYPE 1 RECEPTOR [*Rattus norvegicus*] | 0.396520353 |
| AA030377 | | ESTs, Highly similar to PDGF receptor beta-like tumor suppressor [*H. sapiens*] | 0.395814313 |
| C88171 | | ESTs, Weakly similar to KIAA0601 protein [*H. sapiens*] | 0.395639563 |
| AW549905 | Hba-a1 | hemoglobin alpha, adult chain 1 | 0.395434605 |
| AU015378 | Pde7a | phosphodiesterase 7A | 0.395371322 |
| AI429264 | | ESTs, Moderately similar to KIAA0948 protein [*H. sapiens*] | 0.395320909 |
| W87077 | | Cell cycle progression 2 protein (CPR2) [*H. sapiens*] | 0.393842569 |
| AI451393 | | ESTs, Weakly similar to HYPOTHETICAL PROTEIN HI1130 [*Haemophilus influenzae*] | 0.392399983 |
| AI323471 | Zfp147 | Zinc finger protein 147 | 0.391742059 |
| C79534 | Cstf3 | cleavage stimulation factor, 3' pre-RNA, subunit 3 | 0.389435064 |
| AI573376 | Fcer1g | Fc receptor, IgE, high affinity I, gamma polypeptide | 0.385223818 |
| AW549905 | Hba-a1 | hemoglobin alpha, adult chain 1 | 0.384703759 |
| AU045698 | | *Mus musculus* SOCS box-containing WD protein SWiP-2 (Swip2) mRNA, complete cds | 0.384692305 |
| W17967 | Pon1 | Paraoxonase 1 | 0.381300142 |
| AA118886 | H2-Oa | Histocompatibility 2, O region alpha locus | 0.379646356 |
| AA183698 | Sell | selectin, lymphocyte | 0.378737018 |
| AA028411 | D7Ertd760e | DNA segment, Chr 7, ERATO Doi 760, expressed | 0.377683276 |
| W33982 | HDAC7 | histone deacetylase 7 | 0.375622229 |
| AW544285 | Gnai2 | guanine nucleotide binding protein, alpha inhibiting 2 | 0.375530863 |
| AW544580 | Ero1l-pendin | ERO1-like (*S. cerevisiae*) | 0.373517048 |
| AI327378 | | ESTs, Highly similar to putative E1-E2 ATPase [*M. musculus*] | 0.372692878 |
| C79918 | | *Mus musculus* serine protease OMI (Omi) mRNA, complete cds | 0.371971496 |
| AA423584 | Expi | extracellular proteinase inhibitor | 0.371842492 |
| C81309 | Gata3 | GATA-binding protein 3 | 0.371089436 |
| AW553343 | Lgals7 | lectin, galactose binding, soluble 7 | 0.368788049 |
| AA017742 | Hdac5 | histone deacetylase 5 | 0.368222326 |
| AU021695 | | ESTs, Weakly similar to cDNA EST yk325c7.5 comes from this gene [*C. elegans*] | 0.362313766 |
| AI324651 | Csk | C-src tyrosine kinase | 0.361784019 |
| AI323916 | Hbb-bh3 | Hemoglobin beta, pseudogene bh3 | 0.359390956 |
| AA140511 | Coro1a | coronin, actin binding protein 1A | 0.348942089 |
| AW550250 | | ESTs, Moderately similar to P53-BINDING PROTEIN 53BP2 [*M. musculus*] | 0.348279234 |
| W59402 | | Solute carrier family 2 (facilitated glucose transporter) member 1 | 0.347266069 |
| AI323455 | | *Mus musculus* peptidylglycine alpha-amidating monooxygenase (PAM) mRNA, complete cds | 0.342252509 |
| AI324019 | | ESTs, Highly similar to PANCREATIC LIPASE RELATED PROTEIN 1 PRECURSOR [*Canis familiaris*] | 0.342094965 |
| AI323613 | Inpp5d | Inositol polyphosphate-5-phosphatase, 145 kDa | 0.341842445 |
| W48074 | | ESTs, Weakly similar to U82695_2 expressed-Xq28STS protein [*H. sapiens*] | 0.341545463 |
| AI449289 | | ESTs, Weakly similar to regulator of G protein signaling 12 [*H. sapiens*] | 0.340525506 |
| AW554421 | C1qa | complement component 1, q subcomponent, alpha polypeptide | 0.337939883 |
| AA286654 | LOC54129 | hypothetical protein | 0.337264557 |
| AW549905 | Hba-a1 | hemoglobin alpha, adult chain 1 | 0.330145717 |
| AA008051 | | *Mus musculus* Dkc1 gene for dyskerin, exon 1 and join CDS | 0.330043228 |
| W41258 | | GT12 protein | 0.325468276 |
| AW549905 | Hba-a1 | hemoglobin alpha, adult chain 1 | 0.324856566 |
| AA245029 | Dlk1 | Dlk1-like homolog (*Drosophila*) | 0.321318128 |
| C88087 | Pbx3 | pre B-cell leukemia transcription factor 3 | 0.320595592 |
| AU041875 | Apobec1 | apolipoprotein B editing complex 1 | 0.315363153 |
| AI451067 | | ESTs, Weakly similar to LIGATIN [*M. musculus*] | 0.314553028 |
| AA208883 | Tln | talin | 0.310653211 |
| AI326839 | | *Mus musculus* high mobility group protein homolog HMG4 (Hmg4) mRNA, complete cds | 0.310482414 |
| C79179 | | EST, Weakly similar to organic anion transporter OATP-C [*H. sapiens*] | 0.302074885 |
| AW552972 | | ESTs, Highly similar to ATP-DEPENDENT PROTEASE LA 2 [*Myxococcus xanthus*] | 0.297372968 |
| AA145212 | Clpx | caseinolytic protease X (*E. coli*) | 0.29513184 |
| AI605734 | | VCF-V21-Pnut | 0.295081875 |
| AW546106 | Tyms | thymidylate synthase | 0.295071229 |
| C77182 | | ESTs, Weakly similar to glycogen debranching enzyme isoform 6 [*H. sapiens*] | 0.294297238 |
| AW556657 | | ESTs, Weakly similar to NY-REN-45 antigen [*H. sapiens*] | 0.293288502 |
| AA276003 | Prlr-rs1 | prolactin receptor related sequence 1 | 0.286620436 |
| AU023528 | | *Mus musculus* tescalcin mRNA, complete cds | 0.280511647 |

SUPPLEMENTAL TABLE 4-continued

| Acc No | Gene | Description | N/F ratio |
|---|---|---|---|
| AI528713 | | *Mus musculus* predicted GTP binding protein (IRG-47) mRNA, complete cds | 0.277481051 |
| AW544018 | Slc23a2 | solute carrier family 23, (nucleobase transporters) member 2 | 0.274074155 |
| AA098166 | Pgf | Placental growth factor | 0.265680649 |
| AW551388 | | *Mus musculus* E2F-like transcriptional repressor protein mRNA, complete cds | 0.25836127 |
| AU045552 | Lrp | low density lipoprotein receptor related protein | 0.249126285 |
| C78643 | | ESTs, Moderately similar to H-REV 107 PROTEIN [*R. norvegicus*] | 0.246608761 |
| AI323599 | | H-2 CLASS II HISTOCOMPATIBILITY ANTIGEN, I-A BETA CHAIN PRECURSOR | 0.245441986 |
| AW549905 | Hba-a1 | hemoglobin alpha, adult chain 1 | 0.243800073 |
| AA413508 | Serk1 | SAPK/Erk/kinase 1 | 0.242356002 |
| AA120574 | Sod1 | superoxide dismutase 1, soluble | 0.235267761 |
| AI528547 | C2 | Complement component 2 (within H-2S) | 0.229074483 |
| AW548291 | Hbb-b2 | hemoglobin, beta adult minor chain | 0.227852807 |
| AW552978 | | ESTs, Highly similar to ALPHA-ACTININ, SMOOTH MUSCLE ISOFORM [*Gallus gallus*] | 0.213193615 |
| AW545280 | Tsn | translin | 0.21028048 |
| AA260985 | | ESTs, Weakly similar to ANX7_MOUSE ANNEXIN VII [*M. musculus*] | 0.204873897 |
| W89883 | Col3a1 | Procollagen, type III, alpha 1 | 0.196376754 |
| C78503 | Ask-pending | activator of S phase kinase | 0.193218524 |
| AU022963 | Selp | selectin, platelet | 0.192932242 |
| C86607 | Mat8 | mammary tumor 8 kDa | 0.190339745 |
| AA434863 | | ESTs, Moderately similar to no similarities to reported gene products [*H. sapiens*] | 0.189503955 |
| AI464480 | | ESTs, Moderately similar to KIAA1014 protein [*H. sapiens*] | 0.18862163 |
| AA272807 | H2-Aa | Histocompatibility 2, class II antigen A alpha | 0.167760814 |
| AA413764 | | ESTs, Weakly similar to P24_RAT COP-COATED VESICLE MEMBRANE PROTEIN P24 PRECURSOR [*R. norvegicus*] | 0.143346174 |
| AI451475 | | ESTs, Highly similar to nucleolar protein Nopp140, hepatic [*R. norvegicus*] | 0.121425101 |
| AW553502 | Cola2 | procollagen, type I, alpha 2 | 0.121045883 |

SUPPLEMENTARY TABLE 5

Details of the number of genes up or down regulated in functional group and a comparison of their relative abundance compared to the spots printed on the microarrays.

| Functional Groups | Cell Cycle | Apoptosis Tumor | Suppressors and Oncogenes | Development and Differentiation | Metabolism | Protein Metabolism | Cytoskeletan and ECM | Membrane Associated | Signal Transduction | Nucleic acid chemistry | Others |
|---|---|---|---|---|---|---|---|---|---|---|---|
| Printed on microarrays | 263 | 252 | 77 | 440 | 1102 | 698 | 468 | 1501 | 846 | 1134 | 1893 |
| % of Sum of annotated Regulated in the hyper-invasive cells | 3.0 | 2.9 | 0.9 | 5.1 | 12.7 | 8.0 | 5.4 | 17.3 | 9.8 | 13.1 | 21.8 |
| Total | 14 | 46 | 10 | 70 | 205 | 163 | 93 | 252 | 98 | 145 | 270 |
| upregulated | 11 | 39 | 8 | 59 | 172 | 137 | 78 | 211 | 82 | 121 | 225 |
| downregulated | 3 | 7 | 2 | 11 | 33 | 26 | 15 | 41 | 16 | 24 | 45 |
| % of Sum of regulated | 1.02 | 3.37 | 0.73 | 5.12 | 15.01 | 11.93 | 6.81 | 18.45 | 7.17 | 10.61 | 19.77 |

Difference between printed and regulated
Decrease
Increase

SUPPLEMENTARY TABLE 5-continued

Details of the number of genes up or down regulated in
functional group and a comparison of their relative abundance compared to the spots
printed on the microarrays.

3B: Details of the functional category called "Cell Cycle"

| Gene Symbol | Gene description | Fold change |
|---|---|---|
| | Suppression of cell proliferation | |
| Psmc5 | protease (prosome, macropain) 26S subunit, ATPase 5 | 5.5 |
| Rad9 | cell cycle checkpoint control protein (Rad9) mRNA | 4.0 |
| Hmg1 | high mobility group protein 1 | 3.5 |
| CKS2 | Cyclin-dependent kinases regulatory subunit 2 | 3.4 |
| Cks1 | cyclin-dependent kinase regulatory subunit 1 | 3.2 |
| Fmo5 | flavin containing monooxygenase 5 | 3.0 |
| GAS6 | GAS 6 mRNA associated with growth-arrest | 2.8 |
| Phb | prohibitin | 2.8 |
| Mad2 | mitotin checkpoint component Mad2 mRNA | 2.4 |
| Madh3 | MAD homolog 3 | 2.4 |
| Hmg14 | high mobility group protein 14 | 2.3 |
| | Enhancement of cell proliferation | |
| CGMC | Carcinoembryonic antigen CGM6 precursor | 0.5 |
| CPR2 | Cell cycle progression 2 protein (CPR2) | 0.4 |
| Ask | activator of S phase kinase | 0.2 |

What is claimed is:

1. A method of determining whether a cancer in a tissue of a mammal is likely to metastasize, the method comprising
obtaining a microneedle or capillary filled with a porous matrix comprising a chemotactic factor;
inserting the microneedle or capillary into the tissue for a time sufficient for motile cells to migrate into the porous matrix;
expelling the porous matrix with motile cells from the microneedle or capillary;
combining the porous matrix with microbeads, where the microbeads comprise a binding partner to a surface marker present on macrophages from the tissue;
removing the microbeads and bound macrophages; and
obtaining a gene expression profile of motile tumor cells remaining after removal of the microbeads,
wherein the gene that is profiled includes one or more of collagen type III α1, G-protein coupled receptor 26, Zip code binding protein 1, fibroblast growth factor receptor 1, Arp2/3 p16 subunit, tight junction protein 2, member Ras oncogene family, and epidermal growth factor receptor, and
wherein downregulation of expression of one or more of collagen type III α1, G-protein coupled receptor 26, Zip code binding protein 1, or fibroblast growth factor receptor 1 compared to expression in non-metastatic tumor cells, and/or upregulation of expression of one or more of Arp2/3 p16 subunit, tight junction protein 2, member Ras oncogene family or epidermal growth factor receptor compared to expression in non-metastatic tumor cells indicates that the profiled tumor cells are metastatic tumor cells and that the cancer is likely to metastasize.

2. The method of claim 1, wherein the tissue is mammary tissue.

3. The method of claim 1, wherein the porous matrix comprises matrigel.

4. The method of claim 1, wherein the microneedle or capillary is a microneedle.

5. The method of claim 1, wherein the binding partner is an antibody.

6. The method of claim 1, wherein the chemotactic factor is an epidermal growth factor.

7. The method of claim 1, wherein the binding partner is an antibody is specific for CD11b.

8. The method of claim 1, wherein the gene expression profile is determined using mRNA expression.

9. The method of claim 1, wherein the gene expression profile is determined using protein expression.

10. The method of claim 1, wherein the genes that are profiled include all of collagen type III α1, G-protein coupled receptor 26, Zip code binding protein 1, fibroblast growth factor receptor 1, Arp2/3 p16 subunit, tight junction protein 2, member Ras oncogene family, and epidermal growth factor receptor.

11. A method of identifying metastatic tumor cells from a tumor, the method comprising:
isolating motile tumor cells from the tumor;
obtaining a gene expression profile of the motile tumor cells, wherein the genes that are profiled include all of collagen type III α1, G-protein coupled receptor 26, Zip code binding protein 1, fibroblast growth factor receptor 1, Arp2/3 p16 subunit, tight junction protein 2, member Ras oncogene family, and epidermal growth factor receptor; and comparing the expression of collagen type III α1, G-protein coupled receptor 26, Zip code binding protein 1, fibroblast growth factor receptor 1, Arp2/3 p16 subunit, tight junction protein 2, member Ras oncogene family and epidermal growth factor receptor in the profiled tumor cells to their expression in non-metastatic tumor cells, wherein downregulation of expression of one or more of collagen type III α1, G-protein coupled receptor 26, Zip code binding protein 1, or fibroblast growth factor receptor 1 compared to expression in non-metastatic tumor cells, and/or upregulation of expression of one or more of Arp2/3 p16 subunit, tight junction protein 2, member Ras oncogene family or epidermal growth factor receptor compared to expression in non-metastatic tumor cells indicates that the profiled tumor cells are metastatic tumor cells, thereby identifying said profiled tumor cells as metastatic tumor cells.

12. The method of claim 11, wherein the metastatic tumor cells are breast tumor cells.

13. The method of claim 11, wherein the gene expression profile is determined using mRNA expression.

14. The method of claim 11, wherein the gene expression profile is determined using protein expression.

\* \* \* \* \*

UNITED STATES PATENT AND TRADEMARK OFFICE
CERTIFICATE OF CORRECTION

| | | |
|---|---|---|
| PATENT NO. | : 8,298,756 B2 | Page 1 of 1 |
| APPLICATION NO. | : 11/659514 | |
| DATED | : October 30, 2012 | |
| INVENTOR(S) | : Condeelis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this
Twenty-sixth Day of August, 2014

Michelle K. Lee
*Deputy Director of the United States Patent and Trademark Office*

SEQUENCE LISTING

<160> NUMBER OF SEQ ID NOS: 40

<210> SEQ ID NO 1
<211> LENGTH: 20
<212> TYPE: DNA
<213> ORGANISM: Artificial
<220> FEATURE:
<223> OTHER INFORMATION: Forward primer for Apoptosis Inhibitor 4

<400> SEQUENCE: 1
accttcaaga actggcccTT                                           20

<210> SEQ ID NO 2
<211> LENGTH: 20
<212> TYPE: DNA
<213> ORGANISM: Artificial
<220> FEATURE:
<223> OTHER INFORMATION: Reverse primer for Apoptosis Inhibitor 4

<400> SEQUENCE: 2
aaaacactgg gccaaatcag                                           20

<210> SEQ ID NO 3
<211> LENGTH: 20
<212> TYPE: DNA
<213> ORGANISM: Artificial
<220> FEATURE:
<223> OTHER INFORMATION: Forward primer for Breast Cancer Associated
      Protein 2

<400> SEQUENCE: 3
ttggacaacc cccaattaaa                                           20

<210> SEQ ID NO 4
<211> LENGTH: 20
<212> TYPE: DNA
<213> ORGANISM: Artificial
<220> FEATURE:
<223> OTHER INFORMATION: Reverse primer for Breast Cancer Associated
      Protein 2

```
<400> SEQUENCE: 4
ctggagtgct ttttgaaggc                                          20

<210> SEQ ID NO 5
<211> LENGTH: 20
<212> TYPE: DNA
<213> ORGANISM: Artificial
<220> FEATURE:
<223> OTHER INFORMATION: Forward primer for Defender Against Death 1

<400> SEQUENCE: 5
ttgctggatg cctatctcct                                          20

<210> SEQ ID NO 6
<211> LENGTH: 20
<212> TYPE: DNA
<213> ORGANISM: Artificial
<220> FEATURE:
<223> OTHER INFORMATION: Reverse primer for Defender Against Death 1

<400> SEQUENCE: 6
gcaaaccgct aagatgaagc                                          20

<210> SEQ ID NO 7
<211> LENGTH: 20
<212> TYPE: DNA
<213> ORGANISM: Artificial
<220> FEATURE:
<223> OTHER INFORMATION: Forward primer for Heat Shock Protein 60

<400> SEQUENCE: 7
acacaaatga agaggctggg                                          20

<210> SEQ ID NO 8
<211> LENGTH: 20
<212> TYPE: DNA
<213> ORGANISM: Artificial
<220> FEATURE:
<223> OTHER INFORMATION: Reverse primer for Heat Shock Protein 60

<400> SEQUENCE: 8
actggattag cccctttgct                                          20

<210> SEQ ID NO 9
<211> LENGTH: 20
<212> TYPE: DNA
<213> ORGANISM: Artificial
<220> FEATURE:
<223> OTHER INFORMATION: Forward primer for Integrin Beta 1

<400> SEQUENCE: 9
cagtgaacag caagggtgaa                                          20

<210> SEQ ID NO 10
<211> LENGTH: 20
<212> TYPE: DNA
<213> ORGANISM: Artificial
<220> FEATURE:
<223> OTHER INFORMATION: Reverse primer for Integrin Beta 1

<400> SEQUENCE: 10
taagaacaat tccggcaacc                                          20

<210> SEQ ID NO 11
<211> LENGTH: 20
```

```
<212> TYPE: DNA
<213> ORGANISM: Artificial
<220> FEATURE:
<223> OTHER INFORMATION: Forward primer for Macrophage Migration
      Inhibitory Factor 1

<400> SEQUENCE: 11
ttcatcgtga acaccaatgt                                              20

<210> SEQ ID NO 12
<211> LENGTH: 20
<212> TYPE: DNA
<213> ORGANISM: Artificial
<220> FEATURE:
<223> OTHER INFORMATION: Reverse primer for Macrophage Migration
      Inhibitory Factor 1

<400> SEQUENCE: 12
aaaagtcatg agctggtccg                                              20

<210> SEQ ID NO 13
<211> LENGTH: 20
<212> TYPE: DNA
<213> ORGANISM: Artificial
<220> FEATURE:
<223> OTHER INFORMATION: Forward primer for Ornithine Decarboxylase 1

<400> SEQUENCE: 13
catccaaagg caaagttggt                                              20

<210> SEQ ID NO 14
<211> LENGTH: 20
<212> TYPE: DNA
<213> ORGANISM: Artificial
<220> FEATURE:
<223> OTHER INFORMATION: Reverse primer for Ornithine Decarboxylase 1

<400> SEQUENCE: 14
agcctgctgg ttttcagtgt                                              20

<210> SEQ ID NO 15
<211> LENGTH: 20
<212> TYPE: DNA
<213> ORGANISM: Artificial
<220> FEATURE:
<223> OTHER INFORMATION: Forward primer for Beta-actin

<400> SEQUENCE: 15
gatctggcac cacaccttct                                              20

<210> SEQ ID NO 16
<211> LENGTH: 20
<212> TYPE: DNA
<213> ORGANISM: Artificial
<220> FEATURE:
<223> OTHER INFORMATION: Reverse primer for Beta-actin

<400> SEQUENCE: 16
ggggtgttga aggtctcaaa                                              20

<210> SEQ ID NO 17
<211> LENGTH: 20
<212> TYPE: DNA
<213> ORGANISM: Artificial
<220> FEATURE:
<223> OTHER INFORMATION: Forward primer for GAPDH

<400> SEQUENCE: 17
```
gaagggctca tgaccacagt					20

<210> SEQ ID NO 18
<211> LENGTH: 20
<212> TYPE: DNA
<213> ORGANISM: Artificial
<220> FEATURE:
<223> OTHER INFORMATION: Reverse primer for GAPDH

<400> SEQUENCE: 18
ggatgcaggg atgatgttct					20

<210> SEQ ID NO 19
<211> LENGTH: 20
<212> TYPE: DNA
<213> ORGANISM: Artificial
<220> FEATURE:
<223> OTHER INFORMATION: Foward primer for ZBP1

<400> SEQUENCE: 19
tcaagattgc tccaccagaa					20

<210> SEQ ID NO 20
<211> LENGTH: 20
<212> TYPE: DNA
<213> ORGANISM: Artificial
<220> FEATURE:
<223> OTHER INFORMATION: Reverse primer for ZBP1

<400> SEQUENCE: 20
cttccctgag ccttgaactg					20

<210> SEQ ID NO 21
<211> LENGTH: 20
<212> TYPE: DNA
<213> ORGANISM: Artificial
<220> FEATURE:
<223> OTHER INFORMATION: Forward primer for Arp2/3,p21

<400> SEQUENCE: 21
ttcaaggcca acgtcttctt					20

<210> SEQ ID NO 22
<211> LENGTH: 20
<212> TYPE: DNA
<213> ORGANISM: Artificial
<220> FEATURE:
<223> OTHER INFORMATION: Reverse primer for Arp2/3,p21

<400> SEQUENCE: 22
tctggagttg cacttttgga					20

<210> SEQ ID NO 23
<211> LENGTH: 20
<212> TYPE: DNA
<213> ORGANISM: Artificial
<220> FEATURE:
<223> OTHER INFORMATION: Forward primer Actin gamma

<400> SEQUENCE: 23
actgggacga catggagaag					20

<210> SEQ ID NO 24
<211> LENGTH: 20
<212> TYPE: DNA
<213> ORGANISM: Artificial

```
<220> FEATURE:
<223> OTHER INFORMATION: Reverse primer Actin gamma

<400> SEQUENCE: 24
tgttagcttt ggggttcagg                                          20

<210> SEQ ID NO 25
<211> LENGTH: 20
<212> TYPE: DNA
<213> ORGANISM: Artificial
<220> FEATURE:
<223> OTHER INFORMATION: Forward primer for LIMK 1

<400> SEQUENCE: 25
tcatcaagag catggacagc                                          20

<210> SEQ ID NO 26
<211> LENGTH: 20
<212> TYPE: DNA
<213> ORGANISM: Artificial
<220> FEATURE:
<223> OTHER INFORMATION: Reverse primer for LIMK 1

<400> SEQUENCE: 26
gaggtctcgg tggatgatgt                                          20

<210> SEQ ID NO 27
<211> LENGTH: 20
<212> TYPE: DNA
<213> ORGANISM: Artificial
<220> FEATURE:
<223> OTHER INFORMATION: Forward primer for Actn3

<400> SEQUENCE: 27
gcaggagcag aacatcatca                                          20

<210> SEQ ID NO 28
<211> LENGTH: 20
<212> TYPE: DNA
<213> ORGANISM: Artificial
<220> FEATURE:
<223> OTHER INFORMATION: Reverse primer for Actn3

<400> SEQUENCE: 28
catgctgtag accgtgtgct                                          20

<210> SEQ ID NO 29
<211> LENGTH: 20
<212> TYPE: DNA
<213> ORGANISM: Artificial
<220> FEATURE:
<223> OTHER INFORMATION: Forward primer for CFL1

<400> SEQUENCE: 29
gtcaagatgc tgccagacaa                                          20

<210> SEQ ID NO 30
<211> LENGTH: 20
<212> TYPE: DNA
<213> ORGANISM: Artificial
<220> FEATURE:
<223> OTHER INFORMATION: Reverse primer for CFL1

<400> SEQUENCE: 30
ggcccagaaa atgaatacca                                          20
```

<210> SEQ ID NO 31
<211> LENGTH: 20
<212> TYPE: DNA
<213> ORGANISM: Artificial
<220> FEATURE:
<223> OTHER INFORMATION: Forward primer for TMOD

<400> SEQUENCE: 31
cgagggttaa aggggaaaag                                         20

<210> SEQ ID NO 32
<211> LENGTH: 20
<212> TYPE: DNA
<213> ORGANISM: Artificial
<220> FEATURE:
<223> OTHER INFORMATION: Reverse primer for TMOD

<400> SEQUENCE: 32
gacaggcatc gttctcccta                                         20

<210> SEQ ID NO 33
<211> LENGTH: 20
<212> TYPE: DNA
<213> ORGANISM: Artificial
<220> FEATURE:
<223> OTHER INFORMATION: Forward primer for MNS1

<400> SEQUENCE: 33
ctgccgatct ctcatcctct                                         20

<210> SEQ ID NO 34
<211> LENGTH: 20
<212> TYPE: DNA
<213> ORGANISM: Artificial
<220> FEATURE:
<223> OTHER INFORMATION: Reverse primer for MNS1

<400> SEQUENCE: 34
gagcacaagc cactctgaca                                         20

<210> SEQ ID NO 35
<211> LENGTH: 20
<212> TYPE: DNA
<213> ORGANISM: Artificial
<220> FEATURE:
<223> OTHER INFORMATION: Forward primer for Cap 1

<400> SEQUENCE: 35
gaaagccacc agtttcaacc                                         20

<210> SEQ ID NO 36
<211> LENGTH: 20
<212> TYPE: DNA
<213> ORGANISM: Artificial
<220> FEATURE:
<223> OTHER INFORMATION: Reverse primer for Cap 1

<400> SEQUENCE: 36
cttgagcact ccaaccacct                                         20

<210> SEQ ID NO 37
<211> LENGTH: 21
<212> TYPE: DNA
<213> ORGANISM: Artificial
<220> FEATURE:
<223> OTHER INFORMATION: Forward primer for Rock 1

```
<400> SEQUENCE: 37
ttcaagccga ctaacggtat g                                             21

<210> SEQ ID NO 38
<211> LENGTH: 20
<212> TYPE: DNA
<213> ORGANISM: Artificial
<220> FEATURE:
<223> OTHER INFORMATION: Reverse primer for Rock 1

<400> SEQUENCE: 38
gctcgaggaa ttctggaaga                                               20

<210> SEQ ID NO 39
<211> LENGTH: 20
<212> TYPE: DNA
<213> ORGANISM: Artificial
<220> FEATURE:
<223> OTHER INFORMATION: Forward primer for Arp2/3,p16

<400> SEQUENCE: 39
gctaggctcg ctgaagaaga                                               20

<210> SEQ ID NO 40
<211> LENGTH: 20
<212> TYPE: DNA
<213> ORGANISM: Artificial
<220> FEATURE:
<223> OTHER INFORMATION: Reverse primer for Arp2/3,p16

<400> SEQUENCE: 40
tattcgtcca cgtccacctt                                               20
```